(12) United States Patent
Mori et al.

(10) Patent No.: US 8,057,990 B2
(45) Date of Patent: Nov. 15, 2011

(54) SCREENING METHOD

(75) Inventors: Masaaki Mori, Osaka (JP); Kimiko Kanehashi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 663 days.

(21) Appl. No.: 11/885,781

(22) PCT Filed: Mar. 7, 2006

(86) PCT No.: PCT/JP2006/304839
§ 371 (c)(1),
(2), (4) Date: Sep. 6, 2007

(87) PCT Pub. No.: WO2006/095897
PCT Pub. Date: Sep. 14, 2006

(65) Prior Publication Data
US 2008/0280938 A1    Nov. 13, 2008

(30) Foreign Application Priority Data
Mar. 8, 2005 (JP) .................................. 2005-064373

(51) Int. Cl.
G01N 33/53 (2006.01)
C07D 219/00 (2006.01)
C07D 219/08 (2006.01)
C07D 219/10 (2006.01)
C07K 14/00 (2006.01)

(52) U.S. Cl. ............. 435/4; 435/7.2; 435/7.21; 546/102; 546/104; 546/105; 530/350

(58) Field of Classification Search ........................ None
See application file for complete search history.

(56) References Cited

U.S. PATENT DOCUMENTS
2003/0105000 A1* 6/2003 Pero et al. ......................... 514/12
2007/0026457 A1 2/2007 Katano et al.

FOREIGN PATENT DOCUMENTS
WO        91/02529       3/1991
WO    WO 01/39780 A1    6/2001

OTHER PUBLICATIONS

Sigma-Aldrich (A79922 9-amino-1, 2, 3 ,4-tetrahydroacridine hydrochloride hydrate 2010).*
Bologa et al. (Nature Chemical Biology Apr. 2006 2:207-212).*
Bowie et al. (Science, 1990, 247:1306-1310).*
Skolnick et al. (Tibtech 18:34-39, 2000).*
Ibragimova and Eade (Biophysical Journal, Oct 1999, vol. 77, pp. 2191-2198).*
Burgess et al. (J of Cell Bio. 111:2129-2138, 1990).*
Lazar et al. (Molecular and Cellular Biology, 1988, 8:1247-1252).*
Scott et al. (Nature Genetics, 1999, 21:440-443).*
Hu, Ming-Kuan, Synthesis and in-vitro anticancer evaluation of bis-tacrine congeners; Journal of Pharmacy and Pharmacology; vol. 53, pp. 83-88, 2001.
Foreign Search Report dated Mar. 19, 2010, corresponding to 06 728 955.3.
European Search Report dated Jul. 14, 2008 issued in European Application No. 06 72 8955.
Kimura et al., "Orphan G Protein-coupled Receptor, GPR41, Induces Apoptosis via a p53/Bax Pathway during Ischemic Hypoxia and Reoxygenation", The Journal of Biological Chemistry, vol. 276, No. 28, Issue of Jul. 13, 2001, pp. 26453-26460.
Ott et al., "Tacrine Therapy is Associated with Reduced Mortality in Nursing Home Residents with Dementia", JAGS, vol. 50, Jan. 2002, pp. 35-40.
M.W. Fariss et al., Tetrahydroaminoacridine-induced Apoptosis in Rat Hepatocytes, Toxicology in Vitro, 1996, pp. 383-393, vol. 10.
Wenming Li et al., Novel Dimeric Acetylcholinesterase Inhibitor Bis(7)-tacrine, but Not Donepezil, Prevents Glutamate-induced Neuronal Apoptosis by Blocking N-Methyl-D-aspartate Receptors, The Journal of Biological Chemistry, 2005, pp. 18179 to 18188, vol. 280, No. 18.
Charles Carmeci et al., Identification of a Gene (GPR30) with Homology to the G-Protein-Coupled Receptor Superfamily Associated with Estrogen Receptor Expression in a Breast Cancer, Genomics, 1997, pp. 607 to 617, vol. 45.
Tytti M. Ahola et al., G Protein-Coupled Receptor 30 Is Critical for a Progestin-Induced Growth Inhibition in MCF-7 Breast Cancer Cells, Endocrinology, 2002, pp. 3376-3384, vol. 143, No. 9.
Tytti M. Ahola et al., Progestin and G Protein-Coupled Receptor 30 Inhibit Mitogen-Activated Protein Kinase Activity in MCF-7 Breast Cancer Cells, Endocrinology, 2002, pp. 4620-4626, vol. 143, No. 12.
Edward J. Filardo et al., Estrogen Action Via the G Protein-Coupled Receptor, GPR30: Stimulation of Adenylyl Cyclase and Camp-Mediated Attenuation of the Epidermal Growth Factor Receptor-to-MAPK Signaling Axix, Molecular Endocrinology, 2002, pp. 70-84, vol. 16, No. 1.

* cited by examiner

Primary Examiner — Peter J Reddig
(74) Attorney, Agent, or Firm — Sughrue Mion, PLLC

(57) ABSTRACT

The present invention provides a medicament for preventing/treating cancer, comprising a tacrine compound, or a compound promoting the binding between the tacrine compound and a protein comprising the same or substantially the same amino acid sequence as the amino acid sequence represented by SEQ ID NO: 1.

7 Claims, 5 Drawing Sheets

SCREENING METHOD

TECHNICAL FIELD

The present invention relates to a method and a kit for screening a pharmaceutical agent using a GPR30 receptor and a tacrine compound, a compound obtainable by the screening method or kit, and the like. More specifically, the present invention relates to a method, a kit and the like for screening a preventive/therapeutic agent for cancer, cardiac diseases, and the like.

BACKGROUND ART

G protein-coupled receptor (GPCR) is a seven-transmembrane receptor and has a function of transmitting signals from hormones, neurotransmitters, cytokines or other molecules to cell membranes. Human GPR30 (hGPR30) known as one GPCR (Owman, C. et al., Biochem. Biophys. Res. Commun., 228, 285-292, 1996) is reported as follows.

When human umbilical vein endothelial cells are exposed to shear stress, the expression amount of hGPR30 is increased (Takada et al., Biochem. Biophys. Res. Commun. 240, 734-741, 1997). The expression of rat GPR30 (also referred to as rGPR30 or GPR41) in myocardial cells is induced when the rat GPR30 is exposed to low oxygen stimulation and then returned to the usual medium (Kimura et al., J. Biol. Chem., 276, 26453-26460, 2001).

hGPR30 is expressed in breast cancer tissues, breast cancer derived cell lines, and placenta on which estrogen receptor (ER) is expressed (Carmeci, C. et al., Genomics, 45, 607-617, 1997). When breast cancer derived cell MCF7 is stimulated with progestin in the presence of estrogen, the expression amount of GPR30 is increased (Ahola, T. M. et al., Eur. J. Biochem., 269, 2485-2490, 2002). Sex hormone is known as adjusting many reproductive functions. For example, in the uterus, progesterone inhibits the proliferation of endometrial epithelial cells induced by estrogen. By contrast, the function of progesterone in mammary gland is not much clarified. Progestin inhibits the proliferation of breast cancer cells and normal mammary gland epithelial cells. It has been shown by an experiment using antisense RNA that the inhibition on proliferation of MCF7 cells by progestin is caused by an increase of the expression amount of GPR30, and thus the possibility that GPR30 is involved in suppressing the proliferation of breast cancer derived cells has been shown (Ahola, T. M. et al., Endocrinology, 143, 3376-3384, 2002). It has also been shown that the inhibition by progestin and GPR30 on proliferation of breast cancer derived cells is caused by the inhibition on activation of MAPK (mitogen-activated protein kinase) (Ahola, T. M. et al., Endocrinology, 143, 4620-4626, 2002). Activation of MAPK by estrogen mediated by GPR30 in breast cancer derived cells such as MCF7 or the like has also been reported (Filard, E. J. et al., Mol. Endocrinol., 14, 1469-1660, 2000). It has been suggested that this occurs because membrane binding EGF (epidermal growth factor) existing on the cell surface of the breast cancer derived cells such as MCF7 is solubilized by the activation of GPR30, and thus the EGF receptor is activated (Filard, E. J. et al., Mol. Endocrinol., 14, 1469-1660, 2000). By contrast, it has also been suggested that stimulation by estrogen increases the intracellular cAMP concentration mediated by GPR30, and thus Raf is suppressed by RKA (protein kinase A) activation to reduce the activation of MAPK (Filard, E. J. et al., Mol. Endocrinol., 16, 70-84, 2002). These facts indicate that GPR30 is a cell membrane receptor of estrogen, and a pharmacological analysis on this issue has recently been reported (Thomas, T. et al., Endocrinology, 146, 624-632, 2005).

Tacrine (1,2,3,4-tetrahydro-9-acridinamine) is an acetylcholine esterase inhibiting substance and is used as a therapeutic agent for Alzheimer's disease, but has not been reported as acting on an intranuclear receptor of estrogen.

DISCLOSURE OF THE INVENTION

A safe and excellent preventive/therapeutic agent for cancer and cardiac diseases is desired.

The present inventors, as a result of accumulating active studies for attaining the above object, found that stimulation by tacrine specifically increases the amount of calcium in CHO cells in which GPR30 is expressed, and that tacrine is a ligand of GPR30. GPR30 has been suggested to be a membrane binding receptor of estrogen, and is known as suppressing the activation of MAPK in breast cancer derived cells. Estrogen is known as exhibiting various physiological actions via intranuclear receptors, and a GPR30-specific ligand which does not act on the intranuclear receptors is required in order to clarify the actions of GPR30. Therefore, pharmaceutical agents effective for cancer or the like can be created using GPR30 and tacrine or a related compound. Based on such knowledge, the present inventors further accumulated studies and completed the present invention.

The present invention provides, for example,

[1] A method for screening a compound or a salt thereof that alters the binding property between (a) a protein comprising the same or substantially the same amino acid sequence as the amino acid sequence represented by SEQ ID NO: 1 or a salt thereof and (b) a tacrine compound, the method comprising using the protein, a partial peptide thereof or a salt thereof, and the tacrine compound;

[2] The screening method according to claim 1, wherein the tacrine compound is a compound represented by formula:

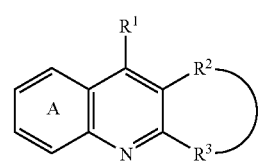

(I)

(in the formula, ring A represents an optionally substituted benzene;

R$^1$ represents an optionally substituted amino; and each of R$^2$ and R$^3$ independently represents an optionally substituted hydrocarbon group, an optionally substituted heterocyclic group, or acyl; or R$^2$ and R$^3$ may form an optionally substituted 3- to 10-membered homo- or heterocyclic group with a carbon atom mutually bound and adjacent thereto) or a salt thereof (hereinafter, the compound or a salt there will be occasionally be referred to simply as "Compound (I));

[3] The screening method according to [1], which comprises using (a) a protein comprising the same or substantially the same amino acid sequence as the amino acid sequence represented by SEQ ID NO: 1, a partial peptide thereof, or a salt thereof and (b) tacrine;

[4] The screening method according to [1], wherein the substantially the same amino acid sequence as the amino acid sequence represented by SEQ ID NO: 1 is the amino acid sequence represented by SEQ ID NO: 2, SEQ ID NO: 3 or SEQ ID NO: 4;

[5] The screening method according to [1], which comprises measuring and comparing a binding amount of the tacrine compound to the protein, a partial peptide thereof, or a salt thereof, (a) in the case where the tacrine compound is brought in contact with the protein comprising the same or substantially the same amino acid sequence as the amino acid sequence represented by SEQ ID NO: 1, a partial peptide thereof, or a salt thereof, and (b) in the case where the tacrine compound and a test compound are brought in contact with the protein, a partial peptide thereof, or a salt thereof;

[6] The screening method according to [1], which comprises measuring and comparing a binding amount of the tacrine compound to a cell, or a membrane fraction of the cell, containing the protein comprising the same or substantially the same amino acid sequence as the amino acid sequence represented by SEQ ID NO: 1, a partial peptide thereof, or a salt thereof, (a) in the case where the tacrine compound is brought in contact with the cell, or a membrane fraction of the cell, and (b) in the case where the tacrine compound and a test compound are brought in contact with the cell, or a membrane fraction of the cell;

[7] The screening method according to [6], wherein the protein comprising the same or substantially the same amino acid sequence as the amino acid sequence represented by SEQ ID NO: 1, a partial peptide thereof, or a salt thereof is a protein, a partial peptide thereof, or a salt thereof expressed on a cell membrane by culturing a transformant containing a DNA encoding the protein, a partial peptide thereof, or a salt thereof;

[8] The screening method according to any one of [5] through [7], wherein the tacrine compound is a labeled tacrine compound;

[9] The screening method according to [1], which comprises measuring and comparing a cell stimulating activity mediated by the protein comprising the same or substantially the same amino acid sequence as the amino acid sequence represented by SEQ ID NO: 1, a partial peptide thereof, or a salt thereof, (a) in the case where the tacrine compound is brought in contact with the protein, a partial peptide thereof, or a salt thereof, and (b) in the case where the tacrine compound and a test compound are brought in contact with the protein, a partial peptide thereof, or a salt thereof;

[10] The screening method according to [1], which comprises measuring and comparing a cell stimulating activity mediated by the protein comprising the same or substantially the same amino acid sequence as the amino acid sequence represented by SEQ ID NO: 1, a partial peptide thereof, or a salt thereof, (a) in the case where the tacrine compound is brought in contact with a cell, or a membrane fraction of the cell, containing the protein, a partial peptide thereof, or a salt thereof, and (b) in the case where the tacrine compound and a test compound are brought in contact with the cell, or a membrane fraction of the cell, containing the protein, a partial peptide thereof, or a salt thereof;

[11] The screening method according to [10], wherein the protein comprising the same or substantially the same amino acid sequence as the amino acid sequence represented by SEQ ID NO: 1, a partial peptide thereof, or a salt thereof is a protein, a partial peptide thereof, or a salt thereof expressed on a cell membrane by culturing a transformant containing a DNA encoding the protein, a partial peptide thereof, or a salt thereof;

[12] A kit for screening a compound or a salt thereof that alters the binding property between (a) a protein comprising the same or substantially the same amino acid sequence as the amino acid sequence represented by SEQ ID NO: 1 or a salt thereof and (b) a tacrine compound, the kit comprising the protein or a salt thereof, and the tacrine compound;

[12a] A compound, or a salt thereof, which can be obtained using the screening method according to [1] or the screening kit according to [12]; [12b] The compound, or a salt thereof, according to [12a], wherein the compound is a compound, or a salt thereof, which inhibits the binding between the protein comprising the same or substantially the same amino acid sequence as the amino acid sequence represented by SEQ ID NO: 1, a partial peptide thereof, or a salt thereof and the tacrine compound;

[12c] The compound, or a salt thereof, according to [12b], which is an agonist;

[12d] The compound, or a salt thereof, according to [12b], which is an antagonist;

[12e] A medicament, comprising a compound, or a salt thereof, which inhibits inhibiting the binding between the protein comprising the same or substantially the same amino acid sequence as the amino acid sequence represented by SEQ ID NO: 1, a partial peptide thereof, or a salt thereof and the tacrine compound;

[12f] A medicament for preventing/treating cancer, promoting cancer cell apoptosis, or (and) suppressing cancer cell proliferation, which comprises the compound or a salt thereof according to [12c];

[12g] A method for preventing/treating a cardiac disease or (and) myocardial cell apoptosis, which comprises the compound or a salt thereof according to [12d];

[13] A medicament for preventing/treating cancer, promoting cancer cell apoptosis, or (and) suppressing cancer cell proliferation, which comprises a tacrine compound;

[14] A method for preventing/treating cancer, promoting cancer cell apoptosis, or (and) suppressing cancer cell proliferation, which comprises promoting an activity of a tacrine compound;

[15] A method for preventing/treating cancer, promoting cancer cell apoptosis, or (and) suppressing cancer cell proliferation, which comprises administering an effective amount of a tacrine compound to a mammal;

[16] Use of a tacrine compound for the manufacture of a medicament for preventing/treating cancer, promoting cancer cell apoptosis, or suppressing cancer cell proliferation; and

[17] A method for preventing/treating a cardiac disease or (and) myocardial cell apoptosis, which comprises inhibiting an activity of a tacrine compound.

Hereinafter, the "protein comprising the same or substantially the same amino acid sequence as the amino acid sequence represented by SEQ ID NO: 1, a partial peptide thereof, or a salt thereof" will be occasionally referred to simply as the "receptor of the present invention" or the "protein of the present invention".

The present invention further provides, for example, (i) A method for screening a compound that alters the binding property between a tacrine compound and the receptor of the present invention, which comprises, in the presence of labeled GTPγS, measuring and comparing the activity to promote the binding of the GTPγS to a cell membrane fraction of the receptor of the present invention, in the case where the tacrine compound is brought in contact with the cell membrane fraction of the receptor of the present invention, and in the case where the tacrine compound and a test compound are brought in contact with the cell membrane fraction of the receptor of the present invention;

(ii) A method for screening a compound that alters the binding property between a tacrine compound and the receptor of the present invention, which comprises, in the presence of a substance for increasing an intracellular cAMP amount, measuring and comparing the activity to suppress the intracellular cAMP production of a cell expressing the receptor of the present invention, in the case where the tacrine compound is brought in contact with the cell expressing the receptor of the present invention, and in the case where the tacrine compound and a test compound are brought in contact with the cell expressing the receptor of the present invention;

(iii) A method for screening a compound that alters the binding property between a tacrine compound and the receptor of the present invention, which comprises, in the presence of a substance for increasing an intracellular cAMP amount, measuring and comparing an enzyme activity of a reporter gene protein, in the case where the tacrine compound is brought in contact with a cell expressing the receptor of the present invention to which a CRE-reporter gene vector has been transfected, and in the case where the tacrine compound and a test compound are brought in contact with the cell expressing the receptor of the present invention to which the CRE-reporter gene vector has been transfected;

(iv) A method for screening a compound that alters the binding property between a tacrine compound and the receptor of the present invention, which comprises measuring and comparing an enzyme activity of a reporter gene protein, in the case where the tacrine compound is brought in contact with a cell expressing the receptor of the present invention to which an SRE-reporter gene vector has been transfected, and in the case where the tacrine compound and a test compound are brought in contact with the cell expressing the receptor of the present invention to which the SRE-reporter gene vector has been transfected;

(v) A method for screening a compound that alters the binding property between a tacrine compound and the receptor of the present invention, which comprises measuring and comparing an arachidonic acid metabolite release activity, in the case where the tacrine compound is brought in contact with a cell expressing the receptor of the present invention containing labeled arachidonic acid, and in the case where the tacrine compound and a test compound are brought in contact with the cell expressing the receptor of the present invention containing the labeled arachidonic acid;

(vi) A method for screening a compound that alters the binding property between a tacrine compound and the receptor of the present invention, which comprises measuring and comparing an intracellular calcium concentration increase activity, in the case where the tacrine compound is brought in contact with a cell expressing the receptor of the present invention, and in the case where the tacrine compound and a test compound are brought in contact with the cell expressing the receptor of the present invention;

(vii) A method for screening a compound that alters the binding property between a tacrine compound and the receptor of the present invention, which comprises, in the presence of labeled inositol, measuring and comparing an inositol triphosphoric acid production activity, in the case where the tacrine compound is brought in contact with a cell expressing the receptor of the present invention, and in the case where the tacrine compound and a test compound are brought in contact with the cell expressing the receptor of the present invention;

(viii) A method for screening a compound that alters the binding property between a tacrine compound and the receptor of the present invention, which comprises measuring and comparing an enzyme activity of a reporter gene protein, in the case where the tacrine compound is brought in contact with a cell expressing the receptor of the present invention to which a TRE-reporter gene vector has been transfected, and in the case where the tacrine compound and a test compound are brought in contact with the cell expressing the receptor of the present invention to which the TRE-reporter gene vector has been transfected;

(ix) A method for screening a compound that alters the binding property between a tacrine compound and the receptor of the present invention, which comprises measuring and comparing cell proliferation, in the case where the tacrine compound is brought in contact with a cell expressing the receptor of the present invention, and in the case where the tacrine compound and a test compound are brought in contact with the cell expressing the receptor of the present invention;

(x) A method for screening a compound that alters the binding property between a tacrine compound and the receptor of the present invention, which comprises, in the presence of labeled rubidium, measuring and comparing a flow-out activity of labeled rubidium, in the case where the tacrine compound is brought in contact with a cell expressing the receptor of the present invention, and in the case where the tacrine compound and a test compound are brought in contact with the cell expressing the receptor of the present invention;

(xi) A method for screening a compound that alters the binding property between a tacrine compound and the receptor of the present invention, which comprises measuring and comparing an extracellular pH change, in the case where the tacrine compound is brought in contact with a cell expressing the receptor of the present invention, and in the case where the tacrine compound and a test compound are brought in contact with the cell expressing the receptor of the present invention;

(xii) A method for screening a compound that alters the binding property between a tacrine compound and the receptor of the present invention, which comprises culturing yeast expressing the receptor of the present invention to which a histidine synthesis gene has been transfected, bringing the tacrine compound, or the tacrine compound and a test compound, in contact therewith, and measuring and comparing the growth of the yeast; and (xiii) A method for screening a compound that alters the binding property between the tacrine compound and the receptor of the present invention, which comprises measuring and comparing a cell membrane potential change, in the case where the tacrine compound is brought in contact with a *Xenopus laevis* oocyte to which RNA of a gene for the receptor of the present invention has been transfected, and in the case where the tacrine compound and a test compound are brought in contact with the *Xenopus laevis* oocyte to which RNA of a gene for the receptor of the present invention has been transfected.

The tacrine compounds (e.g., Compound (I)), the compounds promoting the activities of the tacrine compounds or salts thereof, the compounds promoting the binding between the receptors of the present invention (e.g., GPR30, etc.) and the tacrine compounds, and the like are useful as, for example, preventive/therapeutic agents, cell apoptosis promoters, cell proliferation suppressors or the like for cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.).

The compounds inhibiting the activities of the tacrine compounds or salts thereof, and the like are useful as, for example, preventive/therapeutic agents for cardiac diseases (e.g., cardiomyopathy, cardiac infarction, heart failure, angina pectoris, etc.), preventive/therapeutic agents for myocardial cell apoptosis, or the like.

The receptors of the present invention (e.g., GPR30, etc.) and the tacrine compounds are useful for screening compounds or salts thereof having a preventive/therapeutic action, a cell apoptosis promoting action, and a cell proliferation suppressing action on cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.), a preventive/therapeutic action on cardiac diseases (e.g., cardiomyopathy, cardiac infarction, heart failure, angina pectoris, etc.), a preventive/therapeutic action on myocardial cell apoptosis, or the like.

BEST MODE FOR CARRYING OUT THE INVENTION

Figure 1:
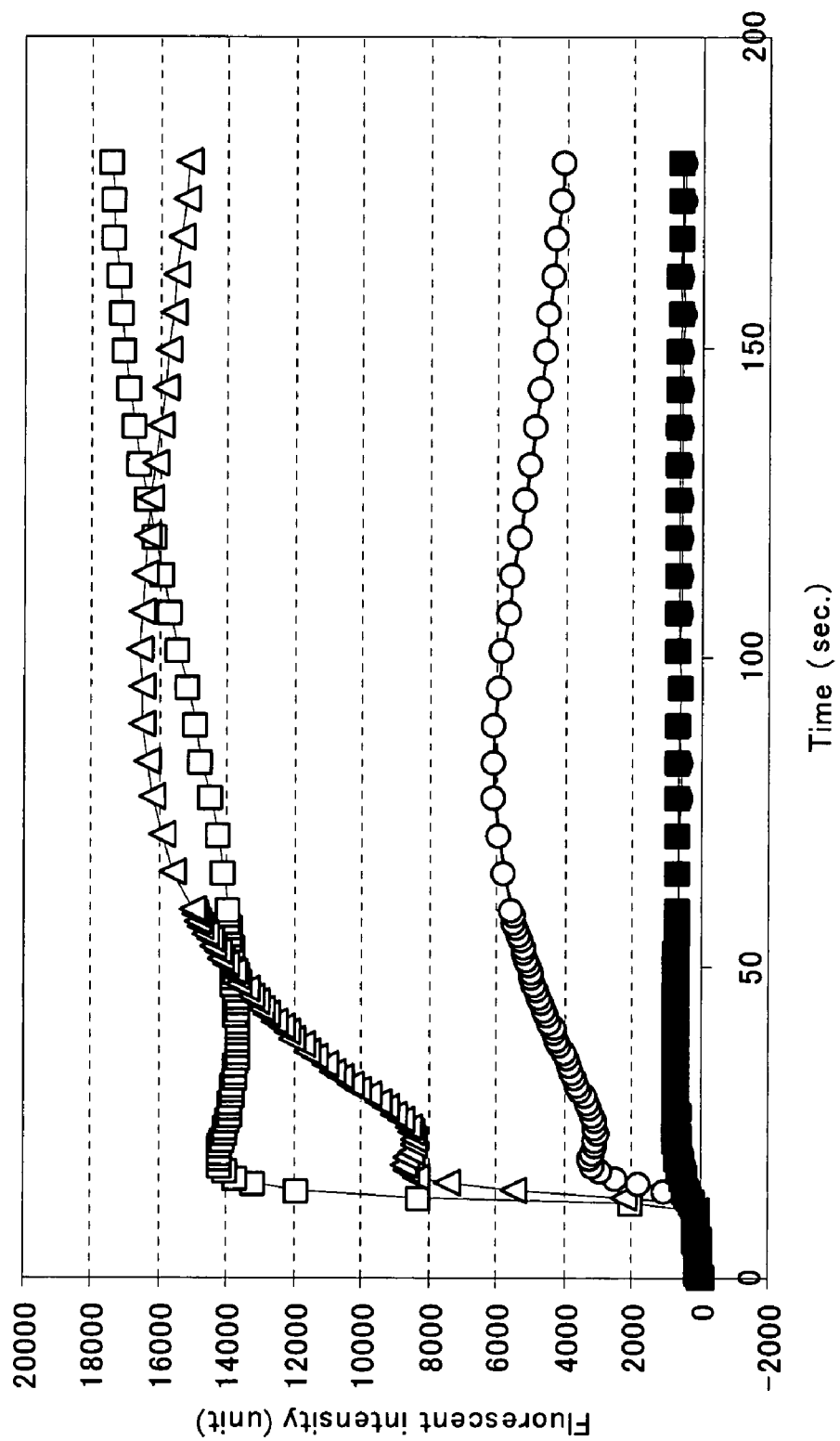
FIG. 1 shows the over-time change of fluorescent intensity of human GPR30 cells with respect to tacrine. In the figure, □ represents the result with 67 μM tacrine, Δ represents the result with 20 μM tacrine, ○ represents the result with 6.7 μM tacrine, ■ represents the result with 2 μM tacrine, and ● represents the result with 0.67 μM tacrine.
Figure 2:
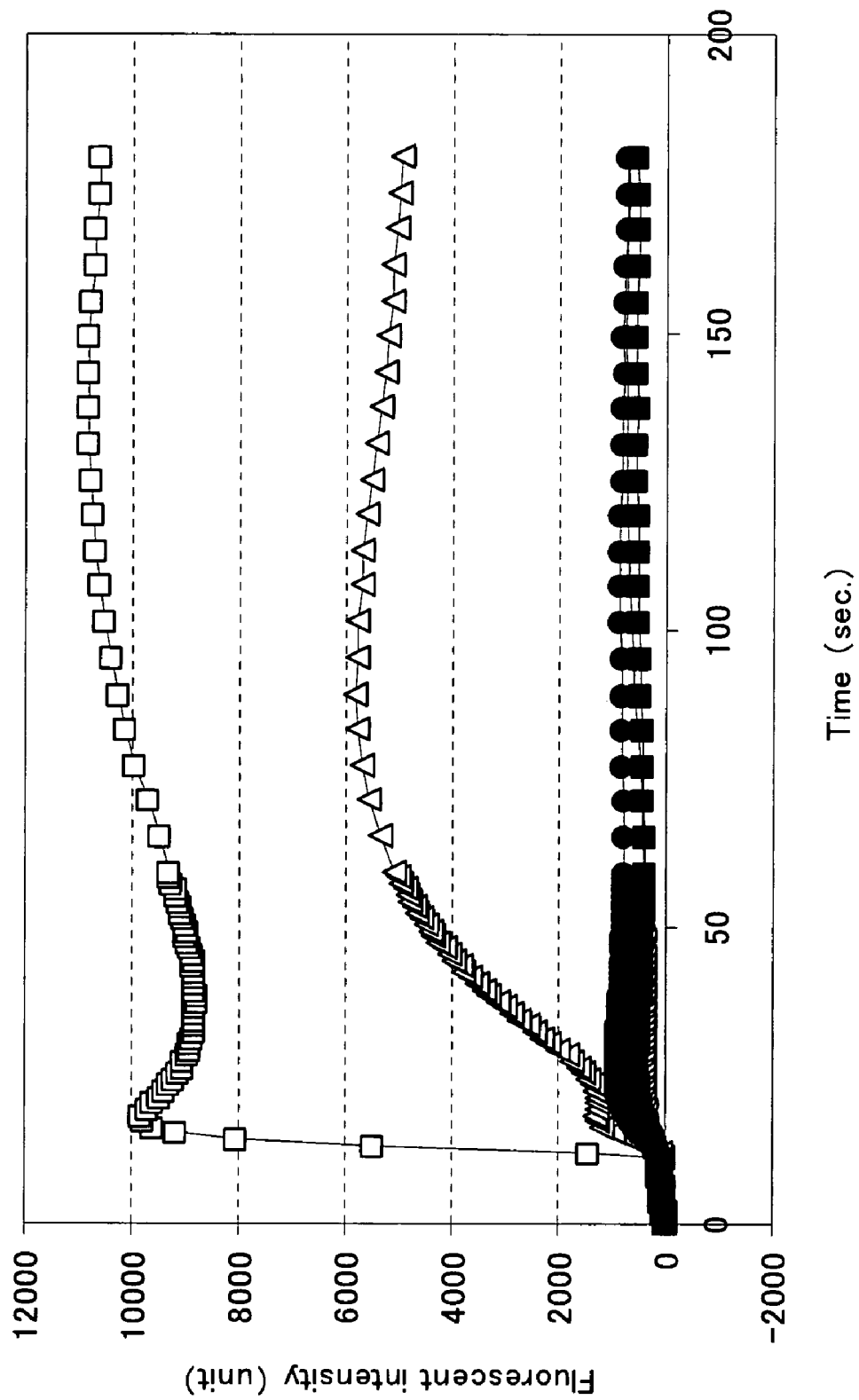
FIG. 2 shows the over-time change of fluorescent intensity of rat GPR30 cells with respect to tacrine. In the figure, □ represents the result with 67 μM tacrine, Δ represents the result with 20 μM tacrine, ○ represents the result with 6.7 μM tacrine, ■ represents the result with 2 μM tacrine, and ● represents the result with 0.67 μM tacrine.
Figure 3:
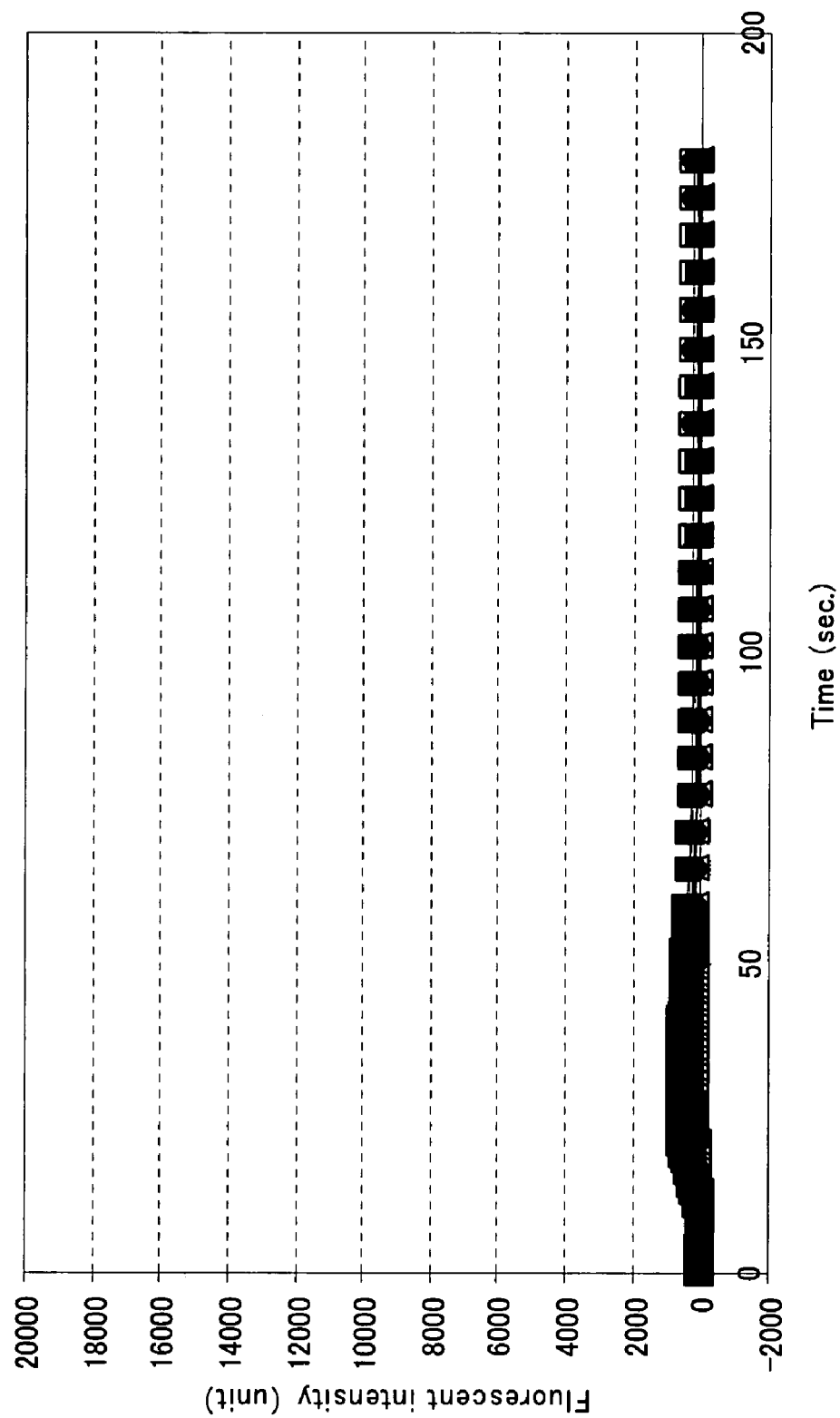
FIG. 3 shows the over-time change of fluorescent intensity of CHO cell lines which do not express GPR30, with respect to tacrine. In the figure, □ represents the result with 67 μM tacrine, Δ represents the result with 20 μM tacrine, ○ represents the result with 6.7 μM tacrine, ■ represents the result with 2 μM tacrine, and ● represents the result with 0.67 μM tacrine.
Figure 4:
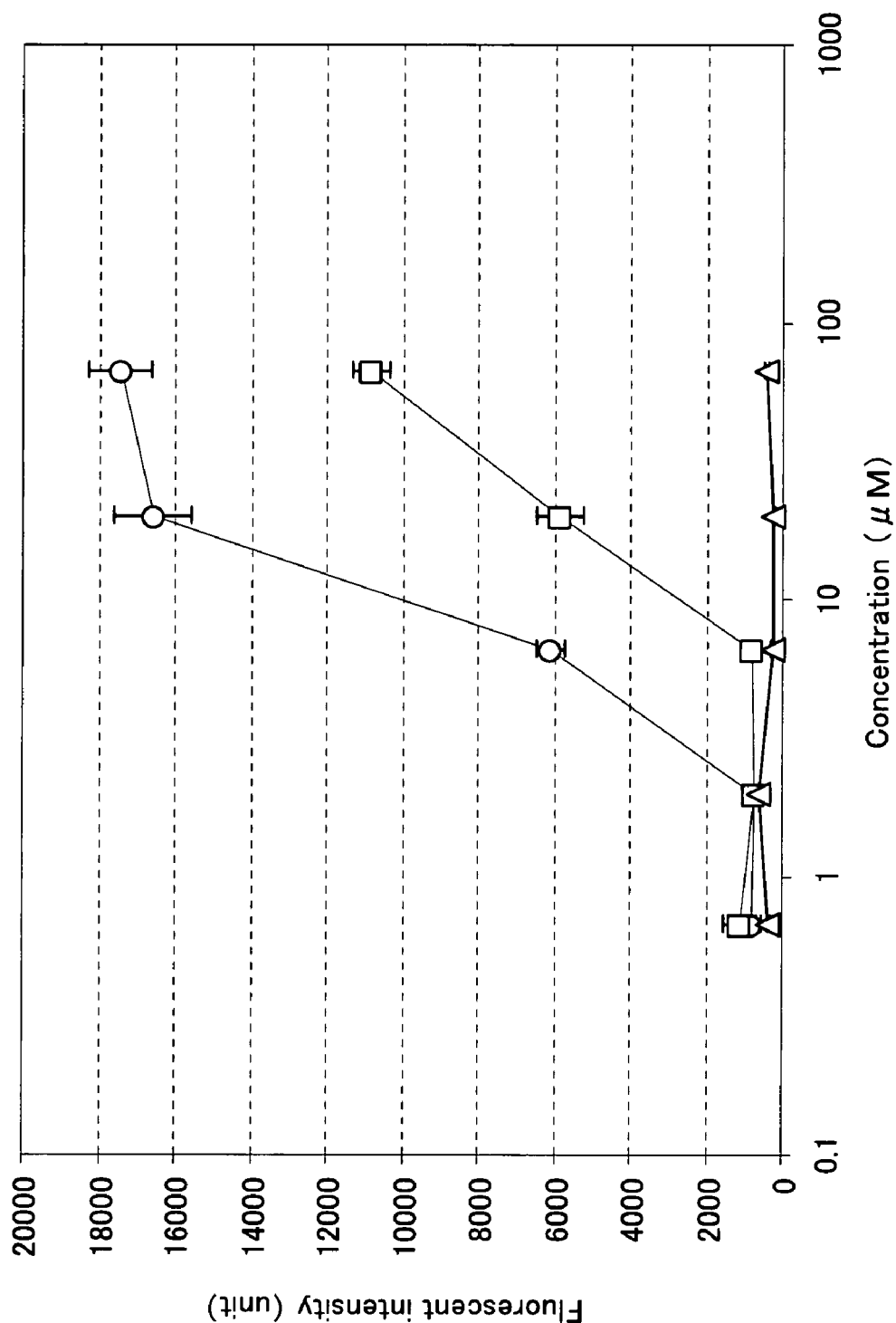
FIG. 4 shows the maximum value of the fluorescent intensity in FLIPR of human GPR30 cells, rat GPR30 cells, and CHO cells which do not express GPR30, with respect to tacrine of various concentrations. In the figure, ○ represents the result with the human GPR30 cells, □ represents the result with the rat GPR30 cells, and Δ represents the result with CHO cells which do not express GPR30.

The protein comprising the same or substantially the same amino acid sequence as the amino acid sequence represented by SEQ ID NO: 1 may be any protein derived from any cell of human and warm-blooded animals (e.g., guinea pig, rat, mouse, chicken, rabbit, swine, sheep, bovine, monkey, etc.); i.e., any cell of the human and these animals (e.g., retina cells, hepatocyte, splenocyte, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); any tissue where such a cell is present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine, small intestine), blood vessel, heart, thymus, spleen, submandibular gland, peripheral blood, prostate, testicle, ovary, placenta, uterus, bone, joint, skeletal muscle, etc.); any blood cell-type cell or a cultured cell thereof (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); or any synthetic protein.

The amino acid sequence which has substantially the same amino acid sequence as that represented by SEQ ID NO: 1 may be an amino acid sequence having at least about 70% homology, preferably at least about 80% homology, and more preferably at least about 90% homology, to the amino acid sequence represented by SEQ ID NO: 1, or the like.

Homology of the amino acid sequences can be measured under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

Preferably, the protein comprising substantially the same amino acid sequence as the amino acid sequence represented by SEQ ID NO: 1 is, for example, a protein comprising substantially the same amino acid sequence as the amino acid sequence represented by SEQ ID NO: 1 and having activities substantially equivalent to those of the amino acid sequence represented by SEQ ID NO: 1, or the like. Substantially the same amino acid sequence as the amino acid sequence represented by SEQ ID NO: 1 may be, for example, an amino acid sequence represented by SEQ ID NO: 2, an amino acid sequence represented by SEQ ID NO: 3, an amino acid sequence represented by SEQ ID NO: 4, or the like.

As the substantially equivalent activities, there are, for example, ligand binding activities, signal transduction actions, and the like. The term "substantially equivalent" is used to mean that the nature of the activities is equivalent. Thus, the ligand binding activities, signal transduction actions or the like are preferably equivalent (e.g., about 0.01 to about 100 times, preferably about 0.5 to about 20 times, and more preferably 0.5 to about 2 times), but differences in the level of these activities or in the quantitative factors such as the molecular weight of the protein may be present and allowable.

The activities such as ligand binding activities, the signal transduction actions and the like can be determined in accordance with any known method or a method conformed thereto, for example, by the ligand determination methods or the screening methods that will be later described.

As the receptor of the present invention, a protein comprising any of the following amino acid sequences can be used: (i) amino acid sequences wherein 1, or 2 or more, amino acids (for example, approximately 1 to 100 amino acids, preferably approximately 1 to 50 amino acids, preferably approximately 1 to 30 amino acids, more preferably approximately 1 to 10 amino acids, and still more preferably several (1 to 5) amino acids) are deleted from the amino acid sequence represented by SEQ ID NO: 1, SEQ ID NO: 2, SEQ ID NO: 3 or SEQ ID NO: 4; (ii) amino acid sequences wherein 1, or 2 or more, amino acids (for example, approximately 1 to 100 amino acids, preferably approximately 1 to 50 amino acids, preferably approximately 1 to 30 amino acids, more preferably approximately 1 to 10 amino acids, and still more preferably several (1 to 5) amino acids) are added to the amino acid sequence represented by SEQ ID NO: 1, SEQ ID NO: 2, SEQ ID NO: 3 or SEQ ID NO: 4;
(iii) amino acid sequences wherein 1, or 2 or more, amino acids (for example, approximately 1 to 100 amino acids, preferably approximately 1 to 50 amino acids, preferably approximately 1 to 30 amino acids, more preferably approximately 1 to 10 amino acids, and still more preferably several (1 to 5) amino acids) in the amino acid sequence represented by SEQ ID NO: 1, SEQ ID NO: 2, SEQ ID NO: 3 or SEQ ID NO: 4 are substituted with other amino acids; (iv) amino acid sequences wherein 1, or 2 or more, amino acids (for example, approximately 1 to 100 amino acids, preferably approximately 1 to 50 amino acids, preferably approximately 1 to 30 amino acids, more preferably approximately 1 to 10 amino acids, and still more preferably several (1 to 5) amino acids) are inserted to the amino acid sequence represented by SEQ ID NO: 1, SEQ ID NO: 2, SEQ ID NO: 3 or SEQ ID NO: 4 are substituted by other amino acids; (v) any combination of these amino acid sequences described above; and the like.

Specific examples of the receptor of the present invention include proteins comprising the amino acid sequence represented by SEQ ID NO: 1 (human GPR30), proteins comprising the amino acid sequence represented by SEQ ID NO: 2 (rat GPR30), proteins comprising the amino acid sequence represented by SEQ ID NO: 3 (mouse GPR30), proteins comprising the amino acid sequence represented by SEQ ID NO: 3 (human GPR30), and the like.

A partial peptide of the receptor of the present invention (hereinafter, occasionally referred to as the "partial peptide of the present invention") may be any partial peptide which can be used for the methods for screening the pharmaceutical agents or the like described later. For example, among protein molecules according to the present invention, those located in a site exposed to the outside of a cell membrane and having substantially the same ligand binding activities as those of the receptor can be used.

The partial peptide of the proteins having the amino acid sequence represented by SEQ ID NO: 1, SEQ ID NO: 2, SEQ ID NO: 3 or SEQ ID NO: 4 is a peptide containing parts analyzed to be extracellular domains (hydrophilic domains) in the hydrophobic plotting analysis. A peptide containing a hydrophobic domain in part can be used as well. In addition, the peptide may contain each domain individually or a plurality of domains together.

The partial peptide of the present invention preferably includes at least 20 amino acids, preferably at least 50 amino acid, and more preferably at least 100 amino acids out of each of the amino acid sequences included in the proteins of the present invention.

Herein, the term "substantially equivalent activities" has the same meaning as described above. The "substantially equivalent activities" can be measured by the same manner as described above.

The partial peptide of the present invention may contain (i) an amino acid sequence, wherein 1, or 2 or more, amino acids (preferably approximately 1 to 10 amino acids, and more preferably several (1 to 5) amino acids) are deleted from any of the above-described amino acid sequences; (ii) an amino acid sequence wherein 1, or 2 or more, amino acids (preferably approximately 1 to 20 amino acids, more preferably approximately 1 to 10 amino acids, and still more preferably several (1 to 5) amino acids) are added to any of the above-described amino acid sequences; or
(iii) an amino acid sequence wherein 1, or 2 or more, amino acids (preferably approximately 1 to 10 amino acids, more preferably several, and still more preferably approximately 1 to 5 amino acids) in any of the above-described amino acid sequences are substituted by other amino acids.

Specific examples of the partial peptide include a peptide containing amino acids of position 59 to position 102, amino acids of position 167 to position 198, amino acids of position 203 to position 224, or amino acids of position 315 to position 338 of the amino acid sequence represented by SEQ ID NO: 1, SEQ ID NO: 2, SEQ ID NO: 3, or SEQ ID NO: 4; and the like.

The receptor of the present invention and the partial peptide of the present invention may be represented in accordance with the conventional way of describing peptides as having the N-terminus (amino terminus) at the left end and the C-terminus (carboxyl terminus) at the right end. The C-terminus may be a carboxy (—COOH), a carboxylate (—COO⁻), an amide (—CONH$_2$), or an ester (—COOR).

Examples of R in the ester group represented include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group (e.g., benzyl, phenethyl, etc.) or an α-naphthyl-$C_{1-2}$-alkyl group (e.g., α-naphthylmethyl, etc.); and the like. In addition, pivaloyloxymethyl or the like, which is used widely as an ester for oral administration, may also be used.

Where the receptor of the present invention or the partial peptide of the present invention contains a carboxy (or a carboxylate) at a position other than the C-terminus, a receptor or a partial peptide having an amidated or esterified carboxy is also encompassed within the scope of the receptor of the present invention or the partial peptide of the present invention. In this case, the ester group may be the same as that in the C-terminus described above.

Furthermore, examples of the receptor of the present invention or the partial peptide of the present invention include variants of the above proteins, wherein an amino group of an amino acid residue at the N-terminal (e.g., methionine residue) is protected with a protecting group (e.g., a $C_{1-6}$ acyl group such as a $C_{1-6}$ alkanoyl group (e.g., formyl group, acetyl group, etc.)); variants wherein the N-terminal glutamyl group, which results from being cleaved in vivo, is pyroglutaminated; variants wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group (e.g., formyl group, acetyl group, etc.)); coupled proteins such as glycoproteins bound to sugar chains; and the like.

As the salt of the receptor of the present invention or the partial peptide of the present invention, preferred are physiologically acceptable acid addition salts (e.g., inorganic acids, organic acids) or bases (e.g., alkaline metal salts). Physiologically acceptable acid addition salts are especially preferable. Examples of such salts include, for example, salts with inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like.

The tacrine compound may be any tacrine or a related compound thereto which specifically binds to the receptor of the present invention. Examples of such a tacrine compound include those having a dissociation constant of 10 μM or less, preferably not greater than 2 μM, more preferably not greater than 1 μM, particularly preferably not greater than 200 nM, and most preferably not greater than 100 nM, in binding to the receptor of the present invention.

The tacrine compound is, for example, Compound (I) or the like.

In Compound (I), examples of the "substituent" in the "optionally substituted benzene ring" represented by ring A include a halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{2-6}$ alkenyl, carboxy-$C_{2-6}$ alkenyl (e.g., 2-carboxyethenyl, 2-carboxy-2-methylethenyl, etc.), optionally halogenated $C_{2-6}$ alkynyl, optionally halogenated or optionally condensed $C_{3-8}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, etc.), optionally halogenated $C_{1-8}$ alkoxy, $C_{1-6}$ alkoxy-carbonyl-$C_{1-6}$ alkoxy (e.g., ethoxycarbonylmethyloxy, etc.), $C_{3-8}$ cycloalkyl-oxy (e.g., cyclopropyloxy, cyclopentyloxy, cyclohexyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, optionally halogenated $C_{1-6}$ alkylthio, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, hydroxyamino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, ethylmethylamino, etc.), di-$C_{6-14}$ arylamino (e.g., diphenylamino, etc.), nitro, nitrile, formyl, carboxy, $C_{1-6}$ alkyl-carbonyl (e.g., acetyl, propionyl, etc.), $C_{3-8}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic carbonyl (e.g., nicotinoyl, isonicotinoyl, thenoyl, furoyl, morpholinocarbonyl, thiomorpholinocarbonyl, piperazine-1-ylcarbonyl, pyrrolidine-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), $C_{1-6}$ alkoxy-carbamoyl (e.g., methoxycarbamoyl, ethoxycarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), sulfo, $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthoylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, naphthylcarbamoyloxy, etc.), 5- or 6-membered heterocyclic carbonyloxy (e.g., nicotinoyloxy, isonicotinoyloxy, etc.), 5- to 7-membered saturated cyclic amino (e.g., pyrrolidine-1-yl, piperidino, piperazine-1-yl, morpholino, thiomorpholino, tetrahydroazepin-1-yl, homopiperazine-1-yl, etc.), a 5- to 10-membered aromatic heterocyclic group (e.g., 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), a 3- to 10-membered non-aromatic heterocyclic group (e.g., 1-azetidinyl, 2-azetidinyl, 3-azetidinyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, 2-piperidyl, 3-piperidyl, 4-piperidyl, 1-piperazinyl, 2-piperazinyl, morpholino, thiomorpholino, 2-oxiranyl, 2-oxetanyl, 3-oxetanyl, 2-tetrahydrofuranyl, 4-tetrahydropyranyl, etc.), oxo, etc.

Ring A may contain 1 to 4, preferably 1 to 2 of the substituents described above at any substitutable positions. When there are two or more substituents, the substituents may be the same or different.

Examples of the "optionally halogenated $C_{1-6}$ alkyl" described above include alkyl (e.g., $C_{1-6}$ alkyl such as methyl, ethyl, propyl, isopropyl, butyl, isobutyl, sec-butyl, tert-butyl, pentyl, hexyl, etc.), which may optionally contain, e.g., 1 to 5, preferably 1 to 3 halogen atoms (e.g., fluorine, chlorine, bromine, iodine, etc.), and the like. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

Examples of the "optionally halogenated $C_{2-6}$ alkenyl" described above include a $C_{2-6}$ alkenyl (e.g., vinyl, propenyl, isopropenyl, 2-buten-1-yl, 4-penten-1-yl, 5-hexen-1-yl, etc.), which may optionally contain, e.g., 1 to 5, preferably 1 to 3 halogen atoms (e.g., fluorine, chlorine, bromine, iodine, etc.), and the like.

Examples of the "optionally halogenated $C_{2-6}$ alkynyl" described above include $C_{2-6}$ alkynyl (e.g., propargyl, 2-butyn-1-yl, 4-pentyn-1-yl, 5-hexyn-1-yl, etc.), which may optionally contain, e.g., 1 to 5, preferably 1 to 3 halogen atoms (e.g., fluorine, chlorine, bromine, iodine, etc.), and the like.

Examples of the "optionally halogenated $C_{3-8}$ cycloalkyl" in the "optionally halogenated or optionally condensed $C_{3-8}$ cycloalkyl" described above include $C_{3-6}$ cycloalkyl (e.g., cyclopropyl, cyclobutyl, cyclopentyl, cyclohexyl, etc.), which may optionally contain, e.g., 1 to 5, preferably 1 to 3 halogen atoms (e.g., fluorine, chlorine, bromine, iodine, etc.), and the like. Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, and the like.

Examples of the "condensed $C_{3-8}$ cycloalkyl" in the "optionally halogenated or optionally condensed $C_{3-8}$ cycloalkyl" described above include 8- to 14-membered bicyclic or tricyclic $C_{3-8}$ cycloalkyl (e.g., 1-adamantyl, 2-adamantyl, decalin-1-yl, tetralin-1-yl, 9-fluorenyl, 1-indanyl, 1,2,3,4-tetrahydro-1-naphthyl, etc.), and the like. The "condensed $C_{3-8}$ cycloalkyl" may optionally be halogenated.

Examples of the "optionally halogenated $C_{1-8}$ alkoxy" described above include $C_{1-8}$ alkoxy (e.g., methoxy, ethoxy, propoxy, isopropoxy, butoxy, isobutoxy, sec-butoxy, pentyloxy, hexyloxy, etc.), which may optionally contain, e.g., 1 to 5, preferably 1 to 3 halogen atoms (e.g., fluorine, chlorine, bromine, iodine, etc.), and the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

Examples of the "optionally halogenated $C_{1-6}$ alkylthio" described above include $C_{1-6}$ alkylthio (e.g., methylthio, ethylthio, propylthio, isopropylthio, butylthio, sec-butylthio, tert-butylthio, etc.), which may optionally contain, e.g., 1 to 5, preferably 1 to 3 halogen atoms (e.g., fluorine, chlorine, bromine, iodine, etc.), and the like. Specific examples include methylthio, difluoromethylthio, trifluoromethylthio, ethylthio, propylthio, isopropylthio, butylthio, 4,4,4-trifluorobutylthio, pentylthio, hexylthio, and the like.

Examples of the "substituent" in the "optionally substituted amino" represented by $R^1$ includes an optionally substituted hydrocarbon group, an optionally substituted heterocyclic group, acyl, and the like. The "amino" may contain 1 or 2 "substituents".

Examples of the "hydrocarbon group" in the "optionally substituted hydrocarbon group" described above include a chain or cyclic hydrocarbon group (e.g., alkyl, alkenyl, alkynyl, cycloalkyl, cycloalkenyl, aryl, aralkyl, a polycyclic hydrocarbon group, etc.), and the like. Among them, a chain or cyclic hydrocarbon group having 1 to 19 carbon atoms and the like are preferred.

Examples of the "alkyl" described above include $C_{1-6}$ alkyl (e.g., methyl, ethyl, propyl, isopropyl, butyl, isobutyl, sec-butyl, tert-butyl, pentyl, neopentyl, hexyl, etc.), and the like.

Examples of the "alkenyl" described above include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.), and the like.

Examples of the "alkynyl" described above include $C_{2-6}$ alkynyl (e.g., ethynyl, propargyl, 1-butynyl, 2-butynyl, 3-butynyl, 1-hexynyl, etc.), and the like.

Examples of the "cycloalkyl" described above include $C_{3-6}$ cycloalkyl (e.g., cyclopropyl, cyclobutyl, cyclopentyl, cyclohexyl, etc.), and the like.

Examples of the "cycloalkenyl" described above include $C_{5-6}$ cycloalkenyl (e.g., 1-cyclopentenyl, 3-cyclopentenyl, 4-cyclopentenyl, 1-cyclohexenyl, 3-cyclohexenyl, 4-cyclohexenyl, etc.), and the like.

Examples of the "aryl" described above include $C_{6-14}$ aryl (e.g., phenyl, 1-naphthyl, 2-naphthyl, 2-biphenylyl, 3-biphenylyl, 4-biphenylyl, 2-anthryl, 3-indenyl, etc.), and the like.

Examples of the "aralkyl" described above include $C_{7-19}$ aralkyl (e.g., benzyl, phenethyl, diphenylmethyl, trityl, 1-naphthylmethyl, 2-naphthylmethyl, 2,2-diphenylethyl, 3-phenylpropyl, 4-phenylbutyl, 5-phenylpenthyl, 9-fluorenyl, etc.), and the like.

Examples of the "polycyclic hydrocarbon group" described above include a bi- to tetracyclic non-aromatic hydrocarbon group (e.g., 1-adamantyl, 2-adamantyl, decalin-1-yl, tetralin-1-yl, indan-1-yl, androstan-3-yl, 5-androsten-3-yl, etc.), and the like.

Examples of the "substituent" in the "optionally substituted hydrocarbon group" described above may be, for example, the same as the examples of the "substituent" in the "optionally substituted benzene ring" represented by ring A described above. The "hydrocarbon group" may contain e.g., 1 to 5, preferably 1 to 3 of the substituents described above at any substitutable positions. When there are two or more substituents, the substituents may be the same or different.

Examples of the "heterocyclic group" in the "optionally substituted heterocyclic group" described above include a monovalent group obtained by removing one optional hydrogen atom from a 5- to 14-membered (monocyclic, bicyclic or tricyclic) heterocyclic ring having, besides carbon atoms, 1 or 2 kind(s) of 1 to 4 hetero atom(s) selected from nitrogen atom, sulfur atom and oxygen atom, preferably (i) a 5- to 14-membered (preferably 5- to 10-membered) aromatic heterocyclic ring having the hetero atom(s) selected as above besides carbon atoms, (ii) a 3- to 14-membered non-aromatic heterocyclic ring having the hetero atom(s) selected as above besides carbon atoms, or (iii) a 7- to 10-membered heterocyclic bridged ring having the hetero atom(s) selected as above besides carbon atoms, and the like.

Examples of the "5- to 14-membered (preferably 5- to 10-membered) aromatic heterocyclic ring" described above include aromatic heterocyclic rings such as thiophene, benzo[b]thiophene, benzo[b]furan, benzimidazole, benzoxazole, benzothiazole, benzisothiazole, 1-H benzotriazole, naphtho[2,3-b]thiophene, furan, pyrrole, imidazole, pyrazole, oxazole, 1,2,3-triazole, 1,2,4-triazole, tetrazole, 1,3,4-thiadiazole, 1,3,4-oxadiazole, pyridine, pyrazine, pyrimidine, pyridazine, indole, isoindole, 1H-indazole, purine, 4H-quinolizine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isoxazole, furazan, phenoxazine, and the like; a ring formed by condensing any of these rings (preferably a monocyclic ring) with one or a plurality of (preferably 1 or 2) aromatic rings (e.g., benzene ring, pyridine ring, imidazole ring, etc.); and the like.

Examples of the "3- to 14-membered non-aromatic heterocyclic ring" described above include oxirane, oxetane, tetrahydrofuran, dihydrofuran, pyran, dioxolane, dioxane, azetidine, pyrrolidine, imidazoline, pyrazolidine, pyrazoline, piperidine, piperazine, morpholine, thiomorpholine, thiazolidine, oxazolidine, oxadiazoline, thiadiazoline, triazoline, 1,4-diazepane, 1,4-oxazepane, 1,4-thiazepane, the reduced forms or partially reduced forms of any of the aromatic heterocyclic rings described above (e.g., 1,2,3,4-tetrahydroquinoline, 1,2,3,4-tetrahydroisoquinoline, indoline, etc.), and the like.

Examples of the "7- to 10-membered heterocyclic bridged ring" described above include quinuclidine, 7-azabicyclo[2.2.1]heptane, and the like.

The "heterocyclic group" is preferably a 5- to 14-membered (preferably 5- to 10-membered) (monocyclic or bicyclic) heterocyclic group having, besides carbon atoms, 1 or 2 kind(s) of preferably 1 to 4 hetero atom(s) selected from nitrogen atom, sulfur atom and oxygen atom. Specific examples include aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 1-pyrrolyl, 3-pyrrolyl, 1-imidazolyl, 2-imidazolyl, 3-pyridazinyl, 2-thiazolyl, 2-oxazolyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; non-aromatic heterocyclic groups such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.; and the like.

Examples of the "substituent" in the "optionally substituted heterocyclic group" described above may be, for example, the same as the examples of the "substituent" in the "optionally substituted benzene ring" represented by ring A described above. The "heterocyclic group" may contain e.g., 1 to 5, preferably 1 to 3 of the substituents described above at any substitutable positions. When there are two or more substituents, the substituents may be the same or different.

Examples of the "acyl" described above include groups represented by formula —(C=O)—OR$^4$, —(C=O)—R$^5$, —(C=O)—NR$^5$R$^6$, —(C=S)—NR$^5$R$^6$, —SO—R$^4$, —SO$_2$—R$^4$ or —SO$_2$—NR$^5$R$^6$ (in the formula, R$^4$ represents an optionally substituted hydrocarbon group or an optionally substituted heterocyclic group; R$^5$ represents a hydrogen atom, an optionally substituted hydrocarbon group or an optionally substituted heterocyclic group; R$^6$ represents a hydrogen atom, an optionally substituted hydrocarbon group or an optionally substituted heterocyclic group; and NR$^5$R$^6$ may be a cyclic amino); and the like.

Examples of the "optionally substituted hydrocarbon group" represented by R$^4$, R$^5$ or R$^6$ include the above-described examples of the "optionally substituted hydrocarbon group" listed as an example of the "substituent" of the "optionally substituted amino" represented by R$^1$, and the like.

Examples of the "optionally substituted heterocyclic group" represented by R$^4$, R$^5$ or R$^6$ include the above-described examples of the "optionally substituted heterocyclic group" listed as an example of the "substituent" of the "optionally substituted amino" represented by R$^1$, and the like.

Examples of the "cyclic amino" represented by NR$^5$R$^6$ include a 5- to 7-membered saturated cyclic amino, which may contain, besides one nitrogen atom and carbon atoms, 1 or 2 kind(s) of preferably 1 to 4 hetero atom(s) selected from nitrogen atom, sulfur atom and oxygen atom. Specific examples include pyrrolidine-1-yl, piperidino, piperazine-1-yl, morpholino, thiomorpholino, tetrahydroazepin-1-yl, homopiperazine-1-yl, and the like.

Examples of the "optionally substituted hydrocarbon group" represented by R$^2$ or R$^3$ include the above-described examples of the "optionally substituted hydrocarbon group" listed as an example of the "substituent" of the "optionally substituted amino" represented by R$^1$, and the like.

Examples of the "optionally substituted heterocyclic group" represented by R$^2$ or R$^3$ include the above-described examples of the "optionally substituted heterocyclic group" listed as an example of the "substituent" of the "optionally substituted amino" represented by R$^1$, and the like.

Examples of the "acyl" represented by R$^2$ or R$^3$ include groups represented by formula —(C=O)—OR$^4$, —(C=O)—R$^5$, —(C=O)—NR$^5$R$^6$, —(C=S)—NR$^5$R$^6$, —SO—R$^4$, —SO$_2$—R$^4$ or —SO$_2$—NR$^5$R$^6$ (in the formula, each symbol has the same significance as described above), and the like.

Examples of the "3- to 10-membered homocyclic group" in the "optionally substituted 3- to 10-membered homo- or heterocyclic group" formed by R$^2$ and R$^3$ with a carbon atom mutually bound and adjacent thereto include a 3- to 10-membered unsaturated hydrocarbon, a 3- to 10-membered saturated hydrocarbon, and the like.

Examples of the "3- to 10-membered unsaturated hydrocarbon" include $C_{3-10}$ cycloalkane (e.g., cyclopropane, cyclobutane, cyclopentane, cyclohexane, cycloheptane, cyclooctane, cyclononane, cyclodecane, etc.), $C_{5-7}$ cycloalkene (e.g., cyclopentene, cyclopentadiene, cyclohexene, 1,3-cyclohexadiene, 1,4-cyclohexadiene, cycloheptene, 1,3-cycloheptadiene, etc.), and the like.

Examples of the 3- to 10-membered saturated hydrocarbon include benzene, naphthalene, and the like.

Examples of the "3- to 10-membered heterocyclic group" in the "optionally substituted 3- to 10-membered homo- or heterocyclic group" formed by R$^2$ and R$^3$ with a carbon atom mutually bound and adjacent thereto include a 5- to 10-membered (monocyclic or bicyclic) heterocyclic ring having, besides carbon atoms, 1 or 2 kind(s) of 1 to 4 hetero atom(s) selected from nitrogen atom, sulfur atom and oxygen atom, preferably (i) a 5- to 10-membered aromatic heterocyclic ring having the hetero atom(s) selected as above besides carbon atoms, (ii) a 3- to 10-membered non-aromatic heterocyclic ring having the hetero atom(s) selected as above besides carbon atoms, or (iii) a 7- to 10-membered heterocyclic bridged ring having the hetero atom(s) selected as above besides carbon atoms, and the like.

Examples of the "5- to 10-membered aromatic heterocyclic ring" described above include aromatic heterocyclic rings such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthylidine, quinoxaline, quinazoline, cinnoline, carbazole, β-carboline, phenanthridine, acridine, phenazine, thiazole, isothiazole, oxazole, 1,2,3-triazole, 1,2,4-triazole, tetrazole, 1,3,4-thiadiazole, 1,3,4-oxadiazole, 1H-benzotriazole, phenothiazine, isoxazole, furazan, phenoxazine, and the like; a ring formed by condensing any of these rings (preferably a monocyclic ring) with one or a plurality of (preferably 1 or 2) aromatic rings (e.g., benzene ring, etc.); and the like.

Examples of the "3- to 10-membered non-aromatic heterocyclic ring" described above include oxirane, oxetane, tetrahydrofuran, dihydrofuran, pyran, dioxolane, dioxane, azetidine, pyrrolidine, imidazoline, pyrazolidine, pyrazoline, piperidine, piperazine, morpholine, thiomorpholine, thiazolidine, oxazolidine, oxadiazoline, thiadiazoline, triazoline, 1,4-diazepane, 1,4-oxazepane, 1,4-thiazepane, the reduced forms or partially reduced forms of any of the aromatic heterocyclic rings described above (e.g., 1,2,3,4-tetrahydroquinoline, 1,2,3,4-tetrahydroisoquinoline, indoline, etc.), and the like.

Examples of the "7- to 10-membered heterocyclic bridged ring" described above include quinuclidine, 7-azabicyclo[2.2.1]heptane, and the like.

Examples of the "heterocyclic group" described above include a 5- to 10-membered (monocyclic or bicyclic) heterocyclic ring having, besides carbon atoms, 1 or 2 kind(s) of preferably 1 to 4 hetero atom(s) selected from nitrogen atom, sulfur atom and oxygen atom, and the like. More preferably, examples of the "heterocyclic group" include a 5- or 6-membered heterocyclic ring having, besides carbon atoms, 1 to 3 hetero atom(s) selected from nitrogen atom, sulfur atom and oxygen atom (e.g., thiophene, furan, pyrrole, imidazole, pyrazole, pyridine, pyrazine, pyrimidine, pyridazine, etc.), and the like.

Examples of the "substituent" in the "optionally substituted 3- to 10-membered homo- or heterocyclic group" formed by $R^2$ and $R^3$ with a carbon atom mutually bound and adjacent thereto may be, for example, substantially the same as the examples of the "substituent" in the "optionally substituted benzene ring" represented by ring A described above. The "3- to 10-membered homo- or heterocyclic group" may contain 1 to 5, preferably 1 to 3 of the substituents described above at any substitutable positions. When there are two or more substituents, the substituents may be the same or different.

Ring A is preferably an unsubstituted benzene ring.

$R^1$ is preferably an amino.

$R^2$ and $R^3$ preferably form a $C_{5-7}$ cycloalkene (preferably, cyclohexene, etc.) with a carbon atom mutually bound and adjacent thereto.

Preferable specific examples of Compound (I) include tacrine and the like.

Examples of salts of the compounds represented by formula (I) include metal salts, ammonium salts, salts with organic bases, salts with inorganic acids, salts with organic acids, salts with basic or acidic amino acids, and the like. Preferable examples of the metal salts include alkali metal salts such as sodium salts, potassium salts, etc.; alkaline earth metal salts such as calcium salts, magnesium salts, barium salts, etc.; aluminum salts; and the like. Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferable examples of the salts with inorganic acids include salts with hydrochloric acid, hydrobromic acid, nitric acid, sulfuric acid, phosphoric acid, etc. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferable examples of the salts with basic amino acids include salts with arginine, lysine, ornithine, etc. Preferable examples of the salts with acidic amino acids include salts with aspartic acid, glutamic acid, etc.

Of these salts, pharmaceutically acceptable salts are preferred. Where the compounds have, for example, acidic functional groups, examples the pharmaceutically acceptable salts include inorganic salts such as alkali metal salts (e.g., sodium salts, potassium salts, etc.), alkaline earth metal salts (e.g., calcium salts, magnesium salts, barium salts, etc.), and the like; ammonium salts; etc. Where the compounds have basic functional groups, examples of the pharmaceutically acceptable salts include salts with inorganic acids such as hydrobromic acid, nitric acid, sulfuric acid, phosphoric acid, etc.; and salts with organic acids such as acetic acid, phthalic acid, fumaric acid, oxalic acid, tartaric acid, maleic acid, citric acid, succinic acid, methanesulfonic acid, p-toluenesulfonic acid, etc.

Labeled forms of Compound (I) can be used for screening of the present invention as a tacrine compound.

Preferable examples of labeling substrates include radioisotopes (e.g., [$^{125}$I], [$^{131}$I], [$^{3}$H], [$^{14}$C], [$^{32}$P], [$^{33}$P], [$^{35}$S], etc.), fluorescent substances (e.g., cyanine fluorescence dyes (e.g., Cy2, Cy3, Cy5, Cy5.5, Cy7 (manufactured by Amersham Biosciences, Inc.) etc.), fluorescamine, fluorescein isothiocyanate, NBD (7-nitrobenz-2-oxa-1,3-diazol), etc.), enzymes (e.g., β-galactosidase, β-glucosidase, alkaline phosphatase, peroxidase, malate dehydrogenase, etc.), luminescent substances (e.g., luminol, luminol derivatives, luciferin, lucigenin, etc.), biotin, lanthanide element, etc. Among them, radioisotopes [$^{3}$H], [$^{14}$C] and [$^{125}$I] are preferred.

The receptor of the present invention and the partial peptide of the present invention may be produced by any known polypeptide purification method from cells or tissues of human or warm-blooded animals described above, or produced by culturing a transformant obtained by transformation using a DNA encoding polypeptide. Such a receptor or partial peptide may also be produced by a peptide synthesis method, for example, by a method described in Genomics, 56, 12-21, 1999; Biochem. Biophys. Acta. 1446, 57-70, 1999; etc.) or a method conformed thereto.

Such a receptor or partial peptide may be produced from human or mammalian tissues or cells as follows. Human or mammalian tissues or cells are homogenized, and then extracted with an acid or the like. The extracted liquid is purified by a combination of chromatography techniques such as reverse phase chromatography, ion exchange chromatography, and the like to isolate the receptor or the partial peptide.

For synthesizing the receptor or partial peptide of the present invention, or a salt thereof, commercially available resins for polypeptide synthesis may be usually used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc aminoethyl)phenoxy resin, etc. Using any of these resins, amino acids, in which α-amino groups and functional groups on the side chains are appropriately protected, are condensed on the resin in the order of the sequence of the objective polypeptide in accordance with any of various condensation methods known in the art. At the end of the reaction, the polypeptide is excised from the resin and at the same time, the protecting groups are removed. Then, intramolecular disulfide bond-forming reaction is caused in a highly diluted solution to obtain the objective polypeptide, receptor, partial peptide, or an amide thereof.

For condensation of the protected amino acids described above, any of a variety of activation reagents usable for polypeptide synthesis may be used. Carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) may be added directly to the resin, or the protected amino acids may be previously activated in the form of symmetric acid anhydrides, HOBt esters or HOOBt esters, followed by addition of the activated protected amino acids to the resin.

Solvents suitable for use to activate the protected amino acids or condense the protected amino acids with the resin may be appropriately selected from solvents known to be usable for polypeptide condensation reactions. Examples of such solvents include acid amides such as N,N-dimethylformamide, N,N-dimethylacetamide, N-methylpyrrolidone, etc.; halogenated hydrocarbons such as methylene chloride, chloroform, etc.; alcohol such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; appropriate mixtures of any of these solvents; and the like. The reaction temperature is appropriately selected from the range known to be applicable to polypeptide binding reactions and is usually selected from the range of approximately −20° C. to 50° C. The activated amino acid derivatives are generally used in an excess of 1.5 to 4 times. The condensation is examined by a test using the ninhydrin reaction. When the condensation is found to be insufficient as a result of the test, the condensation can be completed by repeating the condensation reaction without removal of the protecting groups. When the condensation is still insufficient even after repeating the reaction, unreacted amino acids can be acetylated with acetic anhydride or acetylimidazole, so that the future reactions will not be influenced.

Examples of the protecting group used to protect the amino groups in the starting materials include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, for example, alkyl esterification (e.g., esterification in the form of linear, branched or cyclic alkyl esters of methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester), phenacyl esterification, benzyloxycarbonyl hydrazidation, t-butoxycarbonyl hydrazidation, trityl hydrazidation, or the like.

A hydroxyl group of serine can be protected through, for example, esterification or etherification. Examples of groups appropriately used for esterification include a lower ($C_{1-6}$) alkanoyl group such as acetyl group, etc., an aroyl group such as benzoyl group, etc., and a group derived from carbonic acid such as benzyloxycarbonyl group, ethoxycarbonyl group, etc. Examples of groups appropriately used for etherification include benzyl group, tetrahydropyranyl group, t-butyl group, etc.

Examples of groups used to protect a phenolic hydroxyl group of tyrosine include Bzl, $Cl_2$-Bzl, 2-nitrobenzyl, Br—Z, t-butyl, etc.

Examples of groups used to protect an imidazole moiety of histidine include Tos, 4-methoxy-2,3,6-trimethylbenzenesulfonyl, DNP, benzyloxymethyl, Bum, Boc, Trt, Fmoc, etc.

Examples of the activated form of the carboxyl group in the starting materials include the corresponding acid anhydride, azides, activated esters (esters with alcohols (e.g., pentachlorophenol, 2,4,5-trichlorophenol, 2,4-dinitrophenol, cyanomethyl alcohol, paranitrophenol, HONB, N-hydroxysuccinimide, N-hydroxyphthalimide, HOBt)), etc. Examples of the activated form of the amino acids in the starting materials include the corresponding phosphoric amides.

Examples of a method which can be used for eliminating (splitting off) the protecting group include catalytic reduction under hydrogen gas flow in the presence of a catalyst such as Pd-black, Pd-carbon, etc.; acid treatment with anhydrous hydrogen fluoride, methanesulfonic acid, trifluoromethanesulfonic acid or trifluoroacetic acid, or a mixture solution thereof; base treatment with diisopropylethylamine, triethylamine, piperidine, piperazine, etc.; reduction with sodium in liquid ammonia; and the like. The elimination of the protecting group by the acid treatment described above is carried out generally at a temperature of approximately −20 to 40° C. In the acid treatment, it is effective to add a cation scavenger such as anisole, phenol, thioanisole, metacresol, paracresol, dimethylsulfide, 1,4-butanedithiol, 1,2-ethanedithiol, etc. Furthermore, 2,4-dinitrophenyl group known as the protecting group for the imidazole of histidine is removed by thiophenol treatment. Formyl group used as the protecting group of the indole of tryptophan is eliminated by deprotection caused by the acid treatment in the presence of 1,2-ethanedithiol, 1,4-butanedithiol, etc. as well as by alkali treatment with a dilute sodium hydroxide solution, dilute ammonia, etc.

Protection of the functional groups that should not be involved in the reaction of the starting materials, protecting groups usable for such protection, elimination of the protecting groups, activation of the functional groups involved in the reaction, or the like may be appropriately selected from known groups or known means.

According to another exemplary method, the receptor or partial peptide of the present invention is obtained as follows. An α-carboxyl group of the carboxy terminal amino acid is first protected by amidation, and then the peptide (polypeptide) chain is extended from the amino group side to a desired length. Thereafter, a polypeptide obtained by eliminating only the protecting group of the N-terminal α-amino group in the peptide chain, and a polypeptide obtained by eliminating only the protecting group of the C-terminal carboxyl group, are produced. The two polypeptides are condensed in a mixture of the solvents described above. The details of the condensation reaction are substantially the same as described above. After the protected polypeptide obtained by the condensation is purified, all the protecting groups are eliminated by the above-described method to give a desired crude polypeptide. This crude polypeptide is purified by any of various known purification means, and the major fraction is lyophilized. Thus, an amidated form of a desired receptor or a partial peptide thereof is obtained.

An esterified form of the receptor or the partial peptide of the present invention, or a salt thereof may be obtained as follows, for example. An α-carboxyl group of the carboxy terminal amino acid is condensed with a desired alcohol to prepare the amino acid ester. After this, an esterified form of a desired receptor or a partial peptide thereof can be obtained by substantially the same procedure as for the amidated form of the desired receptor or a partial peptide thereof.

The receptor or the partial peptide of the present invention can be produced by any known method for peptide synthesis. The partial peptide of the receptor can be produced by cleaving the receptor with an appropriate peptidase. The method for peptide synthesis may be, for example, either solid phase synthesis or liquid phase synthesis. That is, the partial peptide or amino acids that can construct the receptor or the partial peptide of the present invention is condensed with the remaining part. Where the product contains protecting groups, these protecting groups are eliminated to give a desired peptide. Publicly known methods for condensation and elimination of the protecting groups are described in (i)-(v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii), Nobuo Izumiya, et al.: Peptide Gosei-no-Kiso to Jikken (Basics and experiments of peptide synthesis), published by Maruzen Co., Ltd. (1975)

(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)

(v) Haruaki Yajima, ed.: Zoku Iyakuhin no Kaihatsu (Development of Pharmaceuticals, Sequel), Vol. 14, Peptide Synthesis, published by Hirokawa Shoten After the reaction, the product can be purified by a combination of usual purification methods such as solvent extraction, distillation, column chromatography, liquid chromatography, recrystallization and the like to isolate the receptor or the partial peptide of the present invention. When the receptor or the partial peptide obtained by any of the above methods is in a free form, the receptor or the peptide can be converted into an appropriate salt by a known method or a method conformed thereto. Conversely, when obtained in a salt form, the receptor or the peptide can be converted into a free form by a known method or a method conformed thereto.

The polynucleotide encoding the receptor or the partial peptide of the present invention may be any polynucleotide which has the nucleotide sequence encoding the receptor or the partial peptide of the present invention described above. A DNA is preferable, and such a DNA may be any of genomic DNA, genomic DNA library, cDNA derived from the cells and tissues described above, cDNA library derived from the cells and tissues described above, and synthetic DNA.

The vector to be used for the library may be any of bacteriophage, plasmid, cosmid, phagemid and the like. The vector may also be directly amplified by reverse transcriptase polymerase chain reaction (hereinafter, abbreviated as "RT-PCR") using total RNA- or mRNA fraction prepared from the cells and tissues described above.

The DNA encoding the receptor of the present invention may be, for example, any DNA containing a nucleotide sequence represented by SEQ ID NO: 5, SEQ ID NO: 6, SEQ ID NO: 7 or SEQ ID NO: 8; any DNA containing a nucleotide sequence hybridizable to the nucleotide sequence represented by SEQ ID NO: 5, SEQ ID NO: 6, SEQ ID NO: 7 or SEQ ID NO: 8 under high stringent conditions and encoding a receptor which has activities substantially equivalent to those of the protein comprising the amino acid sequence represented by SEQ ID NO: 1, SEQ ID NO: 2, SEQ ID NO: 3 or SEQ ID NO: 4; or the like.

The DNA hybridizable to the nucleotide sequence represented by SEQ ID NO: 5, SEQ ID NO: 6, SEQ ID NO: 7 or SEQ ID NO: 8 under highly stringent conditions may be, for example, a DNA containing a nucleotide sequence having at least about 70% homology, preferably at least about 80% homology, more preferably at least about 90% homology, and still more preferably at least about 95% homology, to the nucleotide sequence represented by SEQ ID NO: 5, SEQ ID NO: 6, SEQ ID NO: 7 or SEQ ID NO: 8.

The hybridization can be carried out by any known method or a method conformed thereto, for example, a method described in Molecular Cloning, 2nd (J. Sambrook et al., Cold Spring Harbor Lab. Press, 1989). The hybridization may also be performed using a commercially available library in accordance with the protocol described in the attached instructions. Preferably, the hybridization may be carried out under highly stringent conditions.

The "highly stringent conditions" used herein refers to, for example, the conditions of a sodium concentration at about 19 to about 40 mM, preferably about 19 to about 20 mM at a temperature of about 50 to about 70° C., preferably about 60 to about 65° C. In particular, the conditions of a sodium concentration of about 19 mM at a temperature of about 65° C. are most preferred.

More specifically, a usable DNA encoding a receptor containing the amino acid sequence represented by SEQ ID NO: 1 may be a DNA containing the nucleotide sequence represented by SEQ ID NO: 5 or the like; a usable DNA encoding a receptor containing the amino acid sequence represented by SEQ ID NO: 2 may be a DNA containing the nucleotide sequence represented by SEQ ID NO: 6 or the like; a usable DNA encoding a receptor containing the amino acid sequence represented by SEQ ID NO: 3 may be a DNA containing the nucleotide sequence represented by SEQ ID NO: 7 or the like; and a usable DNA encoding a receptor containing the amino acid sequence represented by SEQ ID NO: 4 may be a DNA containing the nucleotide sequence represented by SEQ ID NO: 8 or the like.

The DNA encoding the partial peptide of the present invention may be any DNA which contains a nucleotide sequence encoding a partial peptide of the receptor of the present invention. Such a DNA may be any of genomic DNA, genomic DNA library, cDNA derived from the cells and tissues described above, cDNA library derived from the cells and tissues described above, and synthetic DNA. Specifically, such a DNA may be, for example, any DNA containing a partial nucleotide sequence of the DNA having the nucleotide sequence represented by SEQ ID NO: 5, SEQ ID NO: 6, SEQ ID NO: 7 or SEQ ID NO: 8; any DNA having a partial nucleotide sequence of the DNA which has a nucleotide sequence hybridizable to the nucleotide sequence represented by SEQ ID NO: 5, SEQ ID NO: 6, SEQ ID NO: 7 or SEQ ID NO: 8 under high stringent conditions and which encodes a receptor having activities substantially equivalent to those of the protein containing the amino acid sequence represented by SEQ ID NO: 1, SEQ ID NO: 2, SEQ ID NO: 3 or SEQ ID NO: 4; or the like.

The "DNA hybridizable to the nucleotide sequence represented by SEQ ID NO: 5, SEQ ID NO: 6, SEQ ID NO: 7 or SEQ ID NO: 8" has the same significance as described above.

The hybridization methods and highly stringent conditions may be substantially the same as described above.

A polynucleotide (e.g., DNA) encoding the receptor or the partial peptide of the present invention may be labeled with any known method. Examples of the labeling agent include radioisotopes, fluorescent substances (e.g., fluorescein, etc.), luminescent substances, enzymes, biotin, lanthanide element, etc.

The DNA that completely encodes the receptor or the partial peptide of the present invention may be cloned as follows. The DNA may be amplified by any known PCR method using a synthetic DNA primer containing a partial nucleotide sequence of the receptor or the partial peptide of the present invention. Alternatively, the DNA inserted into an appropriate vector may be selected by hybridization with a labeled DNA fragment or a labeled synthetic DNA that encodes a part or the entirety of the region of the receptor or the partial peptide of the present invention. The hybridization can be carried out, for example, in accordance with a method described in Molecular Cloning, 2nd, (J. Sambrook et al., Cold Spring Harbor Lab. Press, 1989). The hybridization may also be performed using a commercially available library in accordance with the protocol described in the attached instructions.

Conversion of the nucleotide sequence of the DNA can be effected by a known method such as the ODA-LA PCR method, the Gapped duplex method, the Kunkel method, etc. or a method conformed thereto, using a known kit, for example, Mutan™-superExpress Km (Takara Shuzo Co., Ltd.), Mutan™-K (Takara Shuzo Co., Ltd.), etc.

The cloned DNA encoding the receptor can be used as it is, or if desired, after digestion with a restriction enzyme or after addition of a linker thereto, depending upon the purpose. The DNA may contain ATG as a translation initiation codon at the 5' terminus thereof and may further contain TAA, TGA or TAG as a translation termination codon at the 3' terminus thereof. These translation initiation and termination codons may also be added by using an appropriate synthetic DNA adapter.

An expression vector for the receptor or the partial peptide of the present invention can be produced by, for example, (a) excising a desired DNA fragment from the DNA encoding the receptor or the partial peptide of the present invention, and then (b) ligating the DNA fragment with an appropriate expression vector downstream with respect to the promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMN, pRc/RSV, pcDNAI/Neo, etc.

The promoter used in the present invention may be any promoter which matches well with a host to be used for gene expression. In the case where animal cells are used as the host, examples of the promoter include SRα promoter, SV40 promoter, HIV*LTR promoter, CMV promoter, HSV-TK promoter, etc.

Among them, CMV (cytomegalovirus) promoter, SRα promoter and the like are preferably used. Where the host is bacteria belonging to the genus *Escherichia*, preferable examples of the promoter include trp promoter, lac promoter, recA promoter, XPL promoter, lpp promoter, T7 promoter, etc. Where the host is bacteria belonging to the genus *Bacillus*, preferable examples of the promoter include SPO1 promoter, SPO2 promoter, penP promoter, etc. Where the host is yeast, preferable examples of the promoter include PHO5 promoter, PGK promoter, GAP promoter, ADH promoter, etc. Where the host is insect cells, preferable examples of the promoter include polyhedrin prompter, P10 promoter, etc.

In addition to the foregoing examples, substances containing an enhancer, a splicing signal, a polyA addition signal, a selection marker, any SV40 replication origin (hereinafter, occasionally abbreviated as "SV40ori"), etc. may be used as the expression vector. Examples of the selection marker include dihydrofolate reductase (hereinafter, occasionally abbreviated as "dhfr") gene [methotrexate (MTX) resistance], ampicillin resistant gene (hereinafter, occasionally abbreviated as "Amp$^r$"), neomycin resistant gene (hereinafter, occasionally abbreviated as "Neo$^r$", G418 resistance), etc. In particular, when dhfr gene is used as the selection marker in dhfr gene deficient Chinese hamster cells, the objective gene may be selected on a thymidine-free media.

When necessary, a signal sequence that matches with the host is added to the N-terminus of the receptor of the present invention. Where the host is bacteria belonging to the genus *Escherichia*, PhoA signal sequence, OmpA signal sequence, etc. are usable as the signal sequence. Where the host is bacteria belonging to the genus *Bacillus*, α-amylase signal sequence, subtilisin signal sequence, etc. are usable as the signal sequence. Where the host is yeast, MFα signal sequence, SUC2 signal sequence, etc. are usable as the signal sequence. Where the host is animal cells, insulin signal sequence, α-interferon signal sequence, antibody molecule signal sequence, etc. are usable as the signal sequence.

Using the vector containing the DNA encoding the receptor or the partial peptide of the present invention thus constructed, a transformant can be produced.

Examples of the host include bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)), JM103 (Nucleic Acids Research, 9, 309 (1981)], JA221 [Journal of Molecular Biology, 120, 517 (1978)], HB101 [Journal of Molecular Biology, 41, 459 (1969)), C600 (Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of the yeast include *Saccharomyces cereviseae* AH22, AH22R$^-$, NA87-11A, DKD-5D, 20B-12, *Schizosaccharomyces pombe* NCYC 1913, NCYC2036, *Pichia pastoris* KM71, etc.

Examples of the insect cells are as follows. For the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc. are usable. For the virus BmNPV, *Bombyx mori* N cells (BmN cells), etc. are usable. Examples of the Sf cell include Sf9 cells (ATCC CRL1711), Sf21 cells (Vaughn, J. L. et al., In Vivo, 13, 213-217 (1977)), etc.

As the insect, for example, a larva of *Bombyx mori*, and the like are usable [Maeda, et al., Nature, 315, 592 (1985)].

Examples of the animal cells include monkey cells COS-7 (COS7), Vero, Chinese hamster cells CHO (hereinafter, abbreviated as "CHO cells"), dhfr gene deficient Chinese hamster cells CHO (hereinafter, abbreviated as "CHO (dhfr$^-$) cells"), mouse L cells, mouse AtT-20, mouse myeloma cells, rat GH3, human FL cells, etc.

The bacteria of the genus *Escherichia* can be transformed in accordance with, for example, a method described in Proc. Natl. Acad. Sci. U.S.A., 69, 2110 (1972), Gene, 17, 107 (1982), etc.

The bacteria of the genus *Bacillus* can be transformed in accordance with, for example, a method described in Molecular & General Genetics, 168, 111 (1979), etc.

Yeast can be transformed in accordance with, for example, a method described in Methods in Enzymology, 194, 182-187 (1991), Proc. Natl. Acad. Sci. U.S.A., 75, 1929 (1978), etc.

Insect cells or insects can be transformed in accordance with, for example, a method described in Bio/Technology, 6, 47-55 (1988), etc.

Animal cells can be transformed in accordance with, for example, a method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, a transformant transformed with an expression vector containing the DNA encoding the receptor or the partial peptide of the present invention can be obtained.

For culturing a transformant having bacteria belonging to the genus *Escherichia* or the genus *Bacillus* as the host, a liquid medium is appropriately usable. The liquid medium is supplemented with materials required for growth of the transformant such as carbon sources, nitrogen sources, inorganic materials, and the like. Examples of the carbon sources include glucose, dextrin, soluble starch, sucrose, etc.

Examples of the nitrogen sources include inorganic or organic materials such as ammonium salts, nitrates, corn steep liquor, peptone, casein, meat extract, soybean cake, potato extract, etc. Examples of the inorganic materials include calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferable example of the medium for incubation of the bacteria belonging to the genus *Escherichia* is M9 medium supplemented with glucose and Casamino acid (Miller, Journal of Experiments in Molecular Genetics, 431-433, Cold Spring Harbor Laboratory, New York, 1972). When necessary, a chemical such as 3β-indolylacrylic acid or the like may be added to the medium to make the promoter act efficiently.

Where the host is bacteria belonging to the genus *Escherichia*, the transformant is usually cultivated at about 15 to about 43° C. for about 3 to about 24 hours. When necessary, the culture may be aerated or agitated.

Where the host is bacteria belonging to the genus *Bacillus*, the transformant is usually cultivated at about 30 to about 40° C. for about 6 to about 24 hours. When necessary, the culture may be aerated or agitated.

Where the host is yeast, the transformant is cultivated in, for example, Burkholder's minimal medium [Bostian, K. L. et al., Proc. Natl. Acad. Sci. U.S.A., 77, 4505 (1980)] or SD medium supplemented with 0.5% Casamino acid [Bitter, G. A. et al., Proc. Natl. Acad. Sci. U.S.A., 81, 5330 (1984)]. Preferably, pH of the medium is adjusted to about 5 to about 8. The transformant is usually cultivated at about 20° C. to about 35° C. for about 24 to about 72 hours. When necessary, the culture may be aerated or agitated.

Where the host is insect cells or insects, the transformant is cultivated in, for example, Grace's Insect Medium (Grace, T. C. C., Nature, 195, 788 (1962)) to appropriately supplemented with an additive such as immobilized 10% bovine serum or the like. Preferably, pH of the medium is adjusted to about 6.2 to about 6.4. The transformant is usually cultivated at about 27° C. for about 3 to 5 days. When necessary, the culture may be aerated or agitated.

Where the host is animal cells, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours. When necessary, the culture may be aerated or agitated.

As described above, the receptor or the partial peptide of the present invention can be produced into the cell, on the cell membrane, or out of the cell of the transformant.

The receptor or the partial peptide of the present invention can be separated by purification of any of the cultures described above by the following procedure.

The receptor or partial peptide of the present invention can be extracted from the culture or cells as follows. After cultivation, the transformants or cells are collected by a known method and suspended in an appropriate buffer solution. The transformants or cells are then disrupted by ultrasonication, treatment with lysozyme and/or freeze-thaw cycling, followed by centrifugation, filtration, etc. Thus, a crude extract of polypeptide is obtained. The buffer solution may contain a protein modifier such as urea, guanidine hydrochloride or the like, or a surfactant such as Triton X-100™, or the like. When the polypeptide is secreted in the culture fluid, after the completion of the cultivation, the supernatant can be separated and collected from the transformants or cells by a known method.

The receptor or the partial peptide contained in the culture supernatant or the extract thus obtained can be purified by appropriately combining known separation and purification methods. Examples of such known separation and purification methods include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

In the case where the receptor or the partial peptide thus obtained is in a free form, the receptor or the partial peptide can be converted into a salt by any known method or a method conformed thereto. By contrast, when the receptor or the partial peptide is in the form of a salt, the receptor or the partial peptide can be converted into a free form or a different salt by any known method or a method conformed thereto.

The receptor or the partial peptide produced by a recombinant can be treated, prior to or after the purification, with an appropriate protein modifying enzyme so that the receptor or the partial peptide can be arbitrarily modified or partially deprived of the polypeptide. Examples of the protein-modifying enzyme include trypsin, chymotrypsin, arginyl endopeptidase, protein kinase, glycosidase, and the like.

A commercially available tacrine compound (e.g., compound (I)) may be used as it is, or a tacrine compound may be produced or extracted by any known method or a method conformed thereto.

An antibody to the protein comprising the same or substantially the same amino acid sequence as the amino acid sequence represented by SEQ ID NO: 1, a partial peptide thereof, or a salt thereof (hereinafter, occasionally referred to as the "antibody of the present invention") may be either a polyclonal antibody or a monoclonal antibody which is capable of recognizing an antibody to the receptor of the present invention. Examples of the antibody to the receptor of the present invention include an antibody for inactivating signal transduction of the receptor, an antibody for activating signal transduction of the receptor, and the like.

The antibody to the receptor of the present invention can be produced in accordance with any known antibody or antiserum production method using the receptor of the present invention as an antigen.

A polynucleotide (e.g., DNA) containing a nucleotide sequence, or a part thereof, complementary or substantially complementary to a polynucleotide (e.g., DNA) encoding the protein comprising the same or substantially the same amino acid sequence as the amino acid sequence represented by SEQ ID NO: 1, a partial peptide thereof, or a salt thereof may be any polynucleotide (antisense polynucleotide) which contains a nucleotide sequence, or a part thereof, complementary or substantially complementary to the encoding polynucleotide and has an action of suppressing the expression of the encoding polynucleotide.

Specifically, such a polynucleotide is, for example, an antisense DNA containing a nucleotide sequence, or a part thereof, which is complementary or substantially complementary to the polynucleotide (e.g., DNA) encoding the receptor of the present invention (hereinafter, a DNA such as the encoding polynucleotide will be occasionally referred to simply as the "DNA of the present invention"; and the antisense DNA explained here will be occasionally referred to simply as the "antisense DNA"). Such a polynucleotide may be any antisense DNA which contains a nucleotide sequence, or a part thereof, complementary or substantially complementary to the DNA of the present invention and has an action of suppressing the expression of the DNA of the present invention.

The nucleotide sequence complementary or substantially complementary to the DNA of the present invention may be, for example, a nucleotide sequence having at least about 70% homology, preferably at least about 80% homology, more preferably at least about 90% homology, and most preferably at least about 95% homology, to the entire nucleotide sequence or a partial nucleotide sequence complementary to the DNA of the present invention (i.e., the comlementary strand to the DNA of the present invention). Especially preferable is an antisense DNA having at least about 70% homology, preferably at least about 80% homology, more preferably at least about 90% homology, and most preferably at least about 95% homology, to the comlementary strand to the nucleotide sequence of the part encoding the N-terminus of the receptor of the present invention (e.g., the nucleotide sequence in the vicinity of the starting codon, etc.), among the entire nucleotide sequence of the comlementary strand to the DNA of the present invention. Such an antisense DNA can be produced using any known DNA synthesis apparatus or the like.

Specifically, such an antisense DNA may be, for example, an antisense polynucleotide containing a nucleotide sequence, or a part thereof, complementary or substantially complementary to the nucleotide sequence of the DNA containing a nucleotide sequence represented by SEQ ID NO: 5, SEQ ID NO: 6, SEQ ID NO: 7, or SEQ ID NO: 8; an antisense polynucleotide containing a nucleotide sequence, or a part thereof, complementary or substantially complementary to the nucleotide sequence of the DNA containing a nucleotide sequence represented by SEQ ID NO: 5, SEQ ID NO: 6, SEQ ID NO: 7, or SEQ ID NO: 8; or the like. Preferably, such an antisense DNA may be, for example, an antisense polynucleotide containing a nucleotide sequence, or a part thereof, complementary to the nucleotide sequence of the DNA containing a nucleotide sequence represented by SEQ ID NO: 5, SEQ ID NO: 6, SEQ ID NO: 7, or SEQ ID NO: 8; an antisense polynucleotide containing a nucleotide sequence, or a part thereof, complementary to the nucleotide sequence of the DNA containing a nucleotide sequence represented by SEQ ID NO: 5, SEQ ID NO: 6, SEQ ID NO: 7, or SEQ ID NO: 8; or the like.

The antisense polynucleotide usually contains about 10 to about 40, preferably about 15 to about 30 bases.

In order to prevent degradation caused by a hydrolase such as nuclease or the like, the phosphoric acid residue (phosphate) of each of nucleotides included in the antisense DNA may be substituted with, for example, a chemically modified phosphate such as phosphorothioate, methyl phosphonate, phosphorodithionate or the like. Such an antisense polynucleotide can be produced by any known DNA synthesis apparatus or the like.

Hereinafter, uses of the receptor of the present invention, the tacrine compound and the like will be described.

[1] Screening of a Compound which is a Pharmaceutical Agent Candidate for Diseases When the receptor of the present invention is exposed to shear stress, the expression amount thereof in the human umbilical vein endothelial cells is increased (Biochem. Biophys. Res. Commun. 240, 734-741, 1997). When the receptor of the present invention is exposed to low oxygen stimulation in the rat myocardial cells and then returned to the usual medium, the expression thereof is induced (J. Biol. Chem., 276, 26453-26460, 2001). The receptor of the present invention is derived from breast cancer derived cell line. Owing to the receptor expression increase, or receptor activation by a ligand, the activation of MAP kinase in the cells is suppressed to induce apoptosis (Endocrinology, 143, 3376-3384, 2002; Mol. Endocrinol., 16, 70-84, 2002).

Using the receptor of the present invention or using a ligand receptor assay system using the expression system of the recombinant receptor of the present invention, a compound (e.g., peptide, protein, antibody, non-peptide compound, synthetic compound, fermentation product, cell extract, plant extract, animal tissue extract, plasma, etc.) or a salt thereof that alters the binding property between the receptor of the present invention and a tacrine compound can be screened efficiently.

Examples of the compound and a salt thereof include (i) compounds having cell stimulating activities (agonist) (e.g., activities that promote arachidonic acid release, acetylcholine release, intracellular $Ca^{2+}$ release, intracellular cAMP production, intracellular cAMP production suppression, intracellular cGMP production, inositol phosphate production, cell membrane potential change, phosphorylation of intracellular proteins, c-fos activation, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), etc.) mediated by the receptor of the present invention, (ii) compounds having no such cell stimulating activities (antagonist), (iii) compound promoting the binding between the receptor of the present invention and the tacrine compound, (iv) compounds inhibiting the binding between the receptor of the present invention and the tacrine compound, and the like.

Specifically, comparison is made between (i) in the case where the tacrine compound is brought in contact with the receptor of the present invention and (ii) in the case where the tacrine compound and a test compound are brought in contact with the receptor of the present invention. The comparison is made by, for example, measuring the binding amount of the tacrine compound to the receptor of the present invention, the cell stimulating activities, or the like.

Specific examples of the screening method of the present invention include:

(a) A method for screening a compound or a salt thereof that alters the binding property between a tacrine compound and the receptor of the present invention, which comprises measuring and comparing a binding amount of the tacrine compound to the receptor of the present invention, (i) in the case where the tacrine compound is brought in contact with the receptor of the present invention, and (ii) in the case where the tacrine compound and a test compound are brought in contact with the receptor of the present invention;

(b) A method for screening a compound or a salt thereof that alters the binding property between a tacrine compound and the receptor of the present invention, which comprises measuring and comparing a binding amount of the tacrine compound to a cell, or a membrane fraction of the cell, containing the receptor of the present invention, (i) in the case where the tacrine compound is brought in contact with the cell, or a membrane fraction of the cell, and (ii) in the case where the tacrine compound and a test compound are brought in contact with a cell, or a membrane fraction of the cell;

(c) The screening method according to (b), wherein the receptor of the present invention is expressed on the cell membrane by culturing a transformant containing a DNA encoding the receptor of the present invention;

(d) A receptor binding assay system such as a screening method according to any of (a) to (c), wherein the tacrine compound is a labeled tacrine compound;

(e) A method for screening a compound or a salt thereof that alters the binding property between a tacrine compound and the receptor of the present invention, which comprises measuring and comparing a cell stimulating activity mediated by the receptor of the present invention, (i) in the case where the tacrine compound is brought in contact with the receptor of the present invention, and (ii) in the case where the tacrine compound and a test compound are brought in contact with the receptor of the present invention;

(f) A method for screening a compound or a salt thereof that alters the binding property between a tacrine compound and the receptor of the present invention, which comprises measuring and comparing a cell stimulating activity mediated by the receptor of the present invention, (a) in the case where the tacrine compound is brought in contact with a cell, or a membrane fraction of the cell, containing the receptor of the present invention, and (b) in the case where the tacrine compound and a test compound are brought in contact with the cell, or a membrane fraction of the cell, containing the receptor of the present invention; and (g) A cell stimulating assay system such as a screening method according to (f), wherein the receptor of the present invention is expressed on the cell membrane by culturing a transformant containing a DNA encoding the receptor of the present invention.

Hereinafter, the screening method according to the present invention will be described specifically.

As the receptor of the present invention, a membrane fraction of organs of human or warm-blooded animals is preferable usable. Since it is especially difficult to obtain human-derived organs, the receptor of the present invention expressed in abundance by use of a recombinant is suitable.

The receptor of the present invention can be produced by any of the above-described receptor production methods.

According to the screening method of the present invention, where a cell or a membrane fraction of the cell containing the receptor of the present invention is used, such a cell or membrane fraction of the cell may be prepared by a method described later.

Where a cell containing the receptor of the present invention is used, the cell may be immobilized with glutaraldehyde, formalin, or the like. The immobilization may be carried out by any known method.

The cell containing the receptor of the present invention refers to a host cell in which the receptor is expressed. Examples of such a host cell include *Escherichia coli, Bacillus subtilis*, yeast, insect cells, animal cells, etc. The production methods of such a host cell are the same as described above.

The membrane fraction of the cell refers to a fraction abundant in cell membrane obtained by any known method after cell disruption. Examples of the cell disruption method include cell squashing using a Potter-Elvehjem homogenizer, disruption using a Waring blender or Polytron (manufactured by Kinematica Inc.), disruption by ultrasonication, disruption by cell spraying through thin nozzles under an increasing pressure using, for example, a French press, and the like. Cell membrane fractionation is effected mainly by a fractionation method using a centrifugal force, such as centrifugation for fractionation, density gradient centrifugation or the like. For example, a cell disruption fluid is centrifuged at a low speed (500 rpm to 3,000 rpm) for a short period of time (normally, about 1 to about 10 minutes), and the resulting supernatant is then centrifuged at a higher speed (15,000 rpm to 30,000 rpm) normally for 30 minutes to 2 hours. The precipitate thus obtained is used as the membrane fraction. The membrane fraction is rich in the expressed receptor of the present invention and membrane components such as cell-derived phospholipids, membrane proteins, etc.

The amount of the receptor of the present invention in a cell, or a membrane fraction of the cell, containing the receptor of the present invention is preferably $10^3$ to $10^8$ molecules per cell, and more preferably $10^5$ to $10^7$ molecules per cell. As the expression amount increases, the ligand binding activity per unit of membrane fraction (specific activity) increases, so that not only a highly sensitive screening system can be constructed but also large quantities of samples can be measured with the same lot.

In order to perform the screening method such as the receptor binding assay system, the cell stimulating assay system or the like described above, the receptor fraction of the present invention and a tacrine compound (e.g., a labeled tacrine compound, etc.) are used, for example. Preferred as the receptor fraction of the present invention is a naturally occurring receptor fraction, a recombinant receptor fraction of the present invention having activities equivalent to the naturally occurring receptor fraction, or the like. Herein, the term "equivalent activities" refers to equivalent ligand binding activities and the like. Examples of the labeled tacrine compound include compounds labeled with radioisotopes (e.g., [$^{125}$I], [$^{131}$I], [$^3$H], [$^{14}$C], [$^{32}$P], [$^{33}$P], [$^{35}$S], etc.), fluorescent substances (e.g., cyanine fluorescence dyes (e.g., Cy2, Cy3, Cy5, Cy5.5, Cy7 (manufactured by Amersham Biosciences, Inc.), fluorescamine, fluorescein isothiocyanate, NBD (7-nitrobenz-2-oxa-1,3-diazol), etc.), enzymes (e.g., β-galactosidase, β-glucosidase, alkaline phosphatase, peroxidase, malate dehydrogenase, etc.), luminescent substances (e.g., luminol, luminol derivatives, luciferin, lucigenin, etc.), biotin, lanthanide element, etc.

More specifically, the compound that alters the binding property of the tacrine compound to receptor of the present invention is screened as follows. Cells, or a membrane fraction of the cells, containing the receptor of the present invention cells are suspended in a buffer appropriate for screening. Thus, a standard receptor is prepared. Any buffer which does not inhibit the binding of the tacrine compound and the receptor is usable; for example, a phosphate buffer or a Tris-hydrochloric acid buffer having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Furthermore, for the purpose of suppressing the degradation of the receptor caused by a protease, a protease inhibitor such as PMSF, leupeptin, E-64 (manufactured by Peptide Institute, Inc.), pepstatin, or the like may also be added. A given amount (5,000 cpm to 500,000 cpm) of a labeled tacrine compound is added to 0.01 ml to 10 ml of a solution of the receptor, in which $10^{-10}$ M to $10^{-7}$ M of a test compound is coexistent. In order to determine the amount of non-specific binding (NSB), a reaction tube charged with an unlabeled tacrine compound in a largely excess amount is also prepared. The reaction is carried out at approximately 0° C. to 50° C., preferably 4° C. to 37° C. for 20 minutes to 24 hours, preferably 30 minutes to 3 hours. After completion of the reaction, the reaction mixture is filtered through glass fiber paper filter or the like and washed with an appropriate amount of the same buffer. Then, the residual radioactivity on the glass fiber paper filter is measured by means of a liquid scintillation counter or γ-counter. The amount of non-specific binding (NSB) is subtracted from the count (Bo) where no antagonizing substance is present and the resulting count (Bo-NSB) is set as 100%. Under this setting, a test compound realizing the specific binding amount (B-NSB) of, for example, 50% or less may be selected as a compound for decreasing the binding property between the tacrine compound and the receptor of the present invention.

In addition, a surface plasmon sensor technology can be used to screen a compound bindable to the receptor of the present invention.

Specifically, a test compound bindable to the receptor of the present invention is selected as follows. The receptor of the present invention is immobilized on a surface of the sensor chip of Biacore 3000 (Biacore), and then a test compound dissolved in phosphate buffered saline (PBS) or the like is flown on the surface of the chip. A change of the surface plasmon at this point is measured. For example, a test compound realizing the change value of 5 resonance unit or greater in the measurement is selected as a substance bindable to the receptor of the present invention.

In order to carry out any of the screening methods of the cell stimulating assay system described above, the following activities mediated by the receptor of the present invention may be measured by any known method or using a commercially available measuring kit: cell stimulating activities (e.g., activities that promote or suppress arachidonic acid release, acetylcholine release, intracellular $Ca^{2+}$ release, intracellular cAMP production, intracellular cAMP production suppression, intracellular cGMP production, inositol phosphoric acid production, cell membrane potential change, phosphorylation of intracellular proteins, c-fos activation, pH reduction, GTPγS binding activity, activation of cAMP-dependent protein kinase, activation of cGMP-dependent protein kinase, activation of phospholipid-dependent protein kinase, activation of mitogen-activated protein kinase (MAP kinase), or the like; intracellular transfer activity of the receptor, etc.). Specifically, such activities can be measured as follows. First, the cells containing the receptor of the present invention are cultured in a multi-well plate or the like. Prior to screening, the medium is replaced with a fresh medium or with an appropriate buffer non-toxic to the cells, followed by incubation for a given period of time in the presence of a test compound or the like. Subsequently, the cells are extracted or the supernatant is recovered, and the resulting product is quantified in accordance with an appropriate method. Where it is difficult to detect the production of a cell stimulating activity indicator (e.g., arachidonic acid, etc.) due to a degrading enzyme contained in the cells, an inhibitor against such as a degrading enzyme may be added prior to the assay. The activities such as the cAMP production suppression activity and the like can be detected as an action suppressing the production of the cells, the baseline production of which has been increased by forskolin or the like.

For performing the screening through the measurement of the cell stimulating activities, cells in which an appropriate receptor of the present invention is expressed are needed. As such cells, the cell line in which the receptor of the present invention is expressed as described above or the like is preferable.

Examples of the test compound include peptide, protein, antibody, non-peptide compound, synthetic compound, fermentation product, cell extract, plant extract, animal tissue extract, plasma, etc.

The screening methods of the cell stimulating assay system will be described more specifically in sections (1) through (13) below.

(1) When a cell expressing a receptor is stimulated by a receptor agonist, the G protein in the cell is activated to cause GTP to bind thereto. This phenomenon is observed also in a membrane fraction of the receptor expression cell. Usually, the GTP is hydrolyzed to change to GDP. However, in the case where the reaction solution contains GTPγS, GTPγS is bound to the G protein like the GTP but is not hydrolyzed and kept bound to the cell membrane containing the G protein. Labeled GTPγS remaining in the cell membrane can be measured to measure the receptor expression cell stimulating activities of the receptor agonist.

This reaction can be used to measure the stimulating activity of a tacrine compound to a cell expressing the receptor of the present invention, and thus screening for a compound that alters the binding property between the tacrine compound and the receptor of the present invention can be performed.

This method is performed using a membrane fraction containing the receptor of the present invention. In this method, a substance which exhibits the activity to promote the binding of the GTPγS to the membrane fraction of the receptor of the present invention is the agonist.

Specifically, screening for a compound that alters the binding property between the tacrine compound and the receptor of the present invention is performed in the presence of labeled GTPγS, by measuring and comparing the activity to promote the binding of the GTPγS to the membrane fraction of the receptor of the present invention, in the case where the tacrine compound is brought in contact with the membrane fraction of the receptor of the present invention, and in the case where the tacrine compound and a test compound are brought in contact with the membrane fraction of the receptor of the present invention.

In this method, a test compound suppressing the activity caused by the tacrine compound to promote the binding of the GTPγS to the membrane fraction of the receptor of the present invention can be selected as an antagonist candidate compound.

Alternatively, screening for an agonist may be performed by bringing only a test compound in contact with the membrane fraction of the receptor of the present invention and measuring the activity to promote the binding of the GTPγS to the membrane fraction of the receptor of the present invention.

One specific example of such a screening method will be described below.

A cell membrane fraction containing the receptor of the present invention prepared in accordance with a known method is diluted with a membrane diluting buffer (50 mM Tris, 5 mM $MgCl_2$, 150 mM NaCl, 1 μM GDP, 0.1% BSA: pH7.4). The diluting ratio varies depending on the expression amount of the receptor. The resultant substance is divided into units of 0.2 ml and put to Falcon2053 by a unit of 0.2 ml. Then, a tacrine compound, or a tacrine compound and a test compound, are added thereto. Further, [$^{35}$G]GTPγS is added thereto to give a final concentration of 200 pM. The resultant substance is kept at 25° C. for 1 hour. After 1.5 ml of an ice-cooled wash buffer (50 mM Tris, 5 mM $MgCl_2$, 150 mM NaCl, 0.1% BSA, 0.05% CHAPS; pH7.4) is added thereto, the resultant substance is filtered with a glass fiber paper filter GF/F. The resultant substance is kept at 65° C. for 30 minutes and dried, and the radioactivity of the [$^{35}$G]GTPγS bound to the membrane fraction remaining on the paper filter is measured by a liquid scintillation counter. Where the radioactivity of the experimental zone to which only the tacrine compound is added is set to 100% and the radioactivity of the experimental zone to which the tacrine compound and the test compound are added is set to 0%, the influence of the test compound on the activity caused by the tacrine compound to promote the binding of the GTPγS is calculated. A test compound realizing the activity to promote the binding of the GTPγS of, for example, 50% or less can be selected as an antagonist candidate compound.

(2) A cell expressing the receptor of the present invention, when stimulated by a tacrine compound, suppresses the intracellular cAMP production. This reaction can be used to measure the stimulating activity of a tacrine compound to the cell expressing the receptor of the present invention, and thus screening for a compound that alters the binding property between the tacrine compound and the receptor of the present invention can be performed.

Specifically, screening for a compound that alters the binding property between the tacrine compound and the receptor of the present invention is performed in the presence of a substance for increasing the intracellular cAMP amount, by measuring and comparing the activity to suppress the intracellular cAMP production of the cell expressing the receptor of the present invention, in the case where the tacrine compound is brought in contact with the cell expressing the receptor of the present invention, and in the case where the tacrine compound and a test compound are brought in contact with the cell expressing the receptor of the present invention.

Examples of the substance for increasing the intracellular cAMP amount include forskolin, calcitonin, and the like.

The intracellular cAMP production amount of the cell expressing the receptor of the present invention may be measured by an RIA system using an anti-cAMP antibody obtained by immunizing mouse, rat, rabbit, goat, bovine or the like and [$^{125}$I] labeled cAMP (both commercially available) or by an EIA system combining an anti-cAMP antibody and labeled cAMP. Alternatively, the cAMP production amount may be quantified by SPA (Scintillation Proximity Assay) using beads containing a scintillant obtained by fixing an anti-cAMP antibody with an antibody to protein A or IgG of the animal used for producing the anti-cAMP antibody or the like and also using [$^{125}$I] labeled cAMP. Still alternatively, the cAMP production amount may be quantified by a competition method cAMP detection kit (PerkinElmer) that applies AlphaScreen (PerkinElmer), which is a chemical-amplification luminescence proximity homogeneous assay system.

In this method, a test compound inhibiting the activity caused by the tacrine compound to suppress the cAMP production in the cell expressing the receptor of the present invention can be selected as an antagonist candidate compound.

Alternatively, screening for a compound exhibiting an agonist activity may be performed by bringing only a test compound in contact with the cell expressing the receptor of the present invention and measuring the activity to suppress the cAMP production.

One specific example of such a screening method will be described below.

Cells expressing the receptor of the present invention (e.g., animal cells such as CHO cells, etc.) are planted to a 24-well plate at a ratio of 5×10$^4$ cells/well and cultured for 48 hours. The cells are washed with a Hanks buffer (pH7.4) containing 0.2 mM 3-isobutyl-methylxanthine, 0.05% BSA and 20 mM HEPES (hereinafter, referred to simply as the "reaction buffer"). Then, 0.5 ml of the reaction buffer is added thereto, and the resultant substance is kept warm for 30 minutes in an incubator. The reaction buffer is removed, and 0.25 ml of the reaction buffer is newly added to the cells. Then, 0.25 ml of the reaction buffer containing 2 µM forskolin containing 20 µM tacrine compound, or 20 µM tacrine compound and a test compound, is added to the cells to allow reaction at 37° C. for 24 minutes. 100 µl of 20% perchloric acid is added and the reaction is stopped. The cells are put on ice for 1 hour to extract intracellular cAMP. The cAMP amount in the extract is measured using a cAMP EIA kit (Amersham Pharmacia Biotech). Where the cAMP amount produced by forskolin stimulation is set to 100% and the cAMP amount resulting from the suppression by the addition of 20 µM tacrine compound is set to 0%, the influence of the test compound on the activity caused by the tacrine compound to suppress cAMP production is calculated. A test compound inhibiting the activity caused by the tacrine compound and realizing the cAMP production activity of, for example, 50% or higher can be selected as an antagonist candidate compound.

In the case where the cell expressing the receptor of the present invention exhibits the property of increasing the intracellular cAMP amount when stimulated by a tacrine compound, screening for a compound that alters the binding property between the tacrine compound and the receptor of the present invention can be performed by measuring and comparing the intracellular cAMP production promotion activity of the cell expressing the receptor of the present invention, in the case where the tacrine compound is brought in contact with the cell expressing the receptor of the present invention, and in the case where the tacrine compound and a test compound are brought in contact with the cell expressing the receptor of the present invention.

In this method, a test compound inhibiting the activity of the tacrine compound to promote the cAMP production in the cell expressing the receptor of the present invention can be selected as an antagonist candidate compound.

Alternatively, screening for a compound exhibiting an agonist activity may be performed by bringing only a test compound in contact with the cell expressing the receptor of the present invention and measuring the activity to promote the cAMP production.

The activity to promote the cAMP production is measured as follows. The cAMP is produced by adding a tacrine compound, or the tacrine compound and a test compound, to the cell expressing the receptor of the present invention (e.g., animal cells such as CHO cells, etc.) as described above but without adding forskolin. The obtained cAMP is quantified by the above-described method.

(3) Screening for a compound that alters the binding property between a tacrine compound and a receptor of the present invention can be performed by measuring the stimulating activity of the tacrine compound to the cell expressing the receptor of the present invention using a CRE-reporter gene vector.

DNA containing a CRE (cAMP response element) is inserted at an upstream position of the reporter gene of a vector to obtain a CRE-reporter gene vector. In the cell expressing the receptor of the present invention having the CRE-reporter gene vector, the stimulation accompanying an increase of the cAMP amount induces the expression of the reporter gene mediated by the CRE and the production of a gene product (protein) of the reporter gene following the receptor gene expression. Namely, a change of the cAMP amount in the cell to which the CRE-reporter gene vector has been transfected can be detected by measuring the enzyme activity of the reporter gene protein.

Specifically, screening for a compound that alters the binding property between the tacrine compound and the receptor of the present invention is performed in the presence of a substance for increasing the intracellular cAMP amount, by measuring and comparing the enzyme activity of the reporter gene protein, in the case where the tacrine compound is brought in contact with the cell expressing the receptor of the present invention to which the CRE-reporter gene vector has been transfected, and in the case where the tacrine compound and a test compound are brought in contact with the cell expressing the receptor of the present invention to which the CRE-reporter gene vector has been transfected.

Examples of the substance for increasing the intracellular cAMP amount include forskolin, calcitonin, and the like.

Examples of the vector include PicaGene basic vector, PicaGene enhancer vector (Toyo Ink Mfg. Co., Ltd.), and the like. DNA containing CRE is inserted at, for example, a multi-cloning site at an upstream position of a reporter gene of such a vector, e.g., a luciferase gene to obtain a CRE-reporter gene vector.

In this method, a test compound recovering the enzyme activity of the reporter gene protein suppressed by the tacrine compound can be selected as an antagonist candidate compound.

Alternatively, screening for an agonist may be performed by bringing only a test compound in contact with the cell expressing the receptor of the present invention and measuring the suppression, similar to that caused by the tacrine compound, on the luminescence amount increased by forskolin stimulation.

A specific example of such a screening method will be described below. In the following example, luciferase is used as a reporter gene.

Cells expressing the receptor of the present invention to which a CRE-reporter gene (luciferase) has been transfected are planted to a 24-well plate at a ratio of $5 \times 10^3$ cells/well and cultured for 48 hours. The cells are washed with a Hanks buffer (pH7.4) containing 0.2 mM 3-isobutyl-methylxanthine, 0.05% BSA and 20 mM HEPES (hereinafter, referred to simply as the "reaction buffer"). Then, 0.5 ml of the reaction buffer is added thereto, and the resultant substance is kept warm for 30 minutes in an incubator. The reaction buffer is removed, and 0.25 ml of the reaction buffer is newly added to the cells. Then, 0.25 ml of the reaction buffer containing 2 µM forskolin having 100 µM tacrine compound, or 100 µM tacrine compound and a test compound, is added to the cells to allow reaction at 37° C. for 24 minutes. The cells are lysed in a cell lysing agent for PicaGene (Toyo Ink Mfg. Co., Ltd.) and a luminescent substrate (Toyo Ink Mfg. Co., Ltd.) is added to the solution. Light emission by luciferase is measured by a luminometer, a liquid scintillation counter, or a top counter. The luminescence amount by luciferase is measured and compared in the case where only the tacrine compound is added and in the case where 100 µM tacrine compound and the test compound are added.

The tacrine compound suppresses the increase of the luminescence amount caused by luciferase based on forskolin stimulation. A compound recovering the luminescence amount can be selected as an antagonist candidate compound.

Examples of the reporter gene include genes such as alkaline phosphatase, chloramphenicol acetyltransferase, β-galactosidase, and the like. The enzyme activity of such a reporter gene protein is measured in accordance with a known method or using a commercially available measuring kit. The activity of alkaline phosphatase is measured using, for example, Lumi-Phos 530 manufactured by Wako Pure Chemical Industries, Ltd.; the activity of chloramphenicol acetyltransferase is measured using, for example, FAST CAT chloramphenicol Acetyltransferase Assay Kit manufactured by Wako Pure Chemical Industries, Ltd.; and the activity β-galactosidase is measured using, for example, Aurora Gal-XE manufactured by Wako Pure Chemical Industries, Ltd.

(4) Screening for a compound that alters the binding property between a tacrine compound and a receptor of the present invention can be performed by measuring the stimulating activity of the tacrine compound to the cell expressing the receptor of the present invention using an SRE-reporter gene vector.

DNA containing an SRE (serum response element) is inserted at an upstream position of the reporter gene of a vector to obtain an SRE-reporter gene vector. In the cell expressing the receptor of the present invention having the SRE-reporter gene vector transfected thereto, the activation of a proliferation signal such as MAP kinase activation or the like by serum stimulation induces the expression of the reporter gene mediated by the SRE and the production of a gene product (protein) of the reporter gene following the reporter gene expression. Namely, the proliferation signal activation in the cell to which the SRE-reporter gene vector has been transfected can be detected by measuring the enzyme activity of the reporter gene protein.

Specifically, screening for a compound that alters the binding property between the tacrine compound and the receptor of the present invention is performed by measuring and comparing the enzyme activity of the reporter gene protein, in the case where the tacrine compound is brought in contact with the cell expressing the receptor of the present invention to which the SRE-reporter gene vector has been transfected, and in the case where the tacrine compound and a test compound are brought in contact with the cell expressing the receptor of the present invention to which the SRE-reporter gene vector has been transfected.

Examples of the vector include PicaGene basic vector, PicaGene enhancer vector (Toyo Ink Mfg. Co., Ltd.), and the like. DNA containing SRE is inserted at, for example, a multi-cloning site at an upstream position of a reporter gene of such a vector, e.g., a luciferase gene to obtain an SRE-reporter gene vector.

In this method, a test compound suppressing the enzyme activation of the reporter gene protein caused by the tacrine can be selected as an antagonist candidate compound.

Alternatively, screening for an agonist may be performed by bringing only a test compound in contact with the cell expressing the receptor of the present invention and measuring the increase, similar to that caused the tacrine compound, of the luminescence amount.

A specific example of such a screening method will be described below. In the following example, luciferase is used as a reporter gene.

Cells expressing the receptor of the present invention to which an SRE-reporter gene (luciferase) has been transfected are planted to a 24-well plate at a ratio of $5 \times 10^3$ cells/well and cultured for 48 hours. The cells are washed with a Hanks buffer (pH7.4) containing 0.05% BSA and 20 mM HEPES (hereinafter, referred to simply as the "reaction buffer"). Then, 0.5 ml of the reaction buffer is added thereto, and the resultant substance is kept warm for 30 minutes in an incubator. The reaction buffer is removed, and 0.25 ml of the reaction buffer is newly added to the cells. Then, 0.25 ml of the reaction buffer containing 100 µM tacrine compound, or 100 µM tacrine compound and a test compound, is added to the cells to allow reaction at 37° C. for 24 minutes. The cells are lysed in a cell lysing agent for PicaGene (Toyo Ink Mfg. Co., Ltd.) and a luminescent substrate (Toyo Ink Mfg. Co., Ltd.) is added to the solution. Light emission by luciferase is measured by a luminometer, a liquid scintillation counter, or a top counter. The luminescence amount by luciferase is measured and compared in the case where only the tacrine compound is added and in the case where 100 µM tacrine compound and the test compound are added.

The tacrine compound increases the luminescence amount caused by luciferase. A compound suppressing the increase can be selected as an antagonist candidate compound.

Examples of the reporter gene include genes such as alkaline phosphatase, chloramphenicol acetyltransferase, β-galactosidase, and the like. The enzyme activity of such a reporter gene protein is measured in accordance with a known method or using a commercially available measuring kit. The activity of alkaline phosphatase is measured using, for example, Lumi-Phos 530 manufactured by Wako Pure Chemical Industries, Ltd.; the activity of chloramphenicol acetyltransferase is measured using, for example, FAST CAT chloramphenicol Acetyltransferase Assay Kit manufactured by Wako Pure Chemical Industries, Ltd.; and the activity of β-galactosidase is measured using, for example, Aurora Gal-XE manufactured by Wako Pure Chemical Industries, Ltd.

(5) A cell expressing the receptor of the present invention, when stimulated by a tacrine compound, releases an arachidonic acid metabolite outside the cell. This reaction can be used to measure the stimulating activity of the tacrine compound to the cell expressing the receptor of the present invention, and thus screening for a compound that alters the binding property between the tacrine compound and the receptor of the present invention can be performed.

Labeled arachidonic acid is incorporated into the cell expressing the receptor of the present invention in advance. Thus, the arachidonic acid metabolite release activity can be measured by measuring the labeled arachidonic acid metabolite which is released outside the cell.

Specifically, screening for a compound that alters the binding property between the tacrine compound and the receptor of the present invention is performed by measuring and comparing the arachidonic acid metabolite release activity, in the case where the tacrine compound is brought in contact with the cell expressing the receptor of the present invention containing the labeled arachidonic acid, and in the case where the tacrine compound and a test compound are brought in contact with the cell expressing the receptor of the present invention containing the labeled arachidonic acid.

In this method, a test compound inhibiting the arachidonic acid metabolite release activity caused by the tacrine compound can be selected as an antagonist candidate compound.

Alternatively, screening for a compound exhibiting an agonist activity may be performed by bringing only a test compound in contact with the cell expressing the receptor of the present invention and measuring the arachidonic acid metabolite release activity of the cell by a known method.

One specific example of such a screening method will be described below.

Cells expressing the receptor of the present invention are planted to a 24-well plate at a ratio of $5 \times 10^4$ cells/well and cultured for 24 hours. [$^3$H] arachidonic acid is added so as to be 0.25 μCi/well. 16 hour later, the cells are washed with a Hanks buffer (pH7.4) containing 0.05% BSA and 20 mM HEPES (hereinafter, referred to simply as the "reaction buffer"). Then, 500 μl of the reaction buffer containing a tacrine compound having a final concentration of 20 μM, or the tacrine compound having a final concentration of 20 μM and a test compound is added to each well. The resultant substance is incubated at 37° C. for 60 minutes, and 400 μl of the reaction solution is added to a scintillator. The amount of the [$^3$H] arachidonic acid metabolite freed in the reaction solution is measured by the scintillator.

Where the amount of the free [$^3$H] arachidonic acid metabolite when only 500 μl of the reaction buffer (with neither the tacrine compound nor the test compound) is added is set to 0% and the amount of the free [$^3$H] arachidonic acid metabolite when the reaction buffer containing 20 μM tacrine compound (with no test compound) is added is set to 100%, the amount of the free [$^3$H] arachidonic acid metabolite when the test compound is added is calculated.

A test compound realizing the arachidonic acid release activity of, for example, 50% or less can be selected as an antagonist candidate compound.

(6) A cell expressing the receptor of the present invention, when stimulated by a tacrine compound, increases the intracellular Ca concentration. This reaction can be used to measure the stimulating activity of the tacrine compound to the cell expressing the receptor of the present invention, and thus screening for a compound that alters the binding property between the tacrine compound and the receptor of the present invention can be performed.

Specifically, screening for a compound that alters the binding property between the tacrine compound and the receptor of the present invention is performed by measuring and comparing the intracellular calcium concentration increase activity, in the case where the tacrine compound is brought in contact with the cell expressing the receptor of the present invention, and in the case where the tacrine compound and a test compound are brought in contact with the cell expressing the receptor of the present invention. The intracellular calcium concentration increase activity is measured by a known method.

In this method, a test compound suppressing the increase of the intracellular calcium concentration caused by the tacrine compound can be selected as an antagonist candidate compound.

Alternatively, screening for an agonist may be performed by bringing only a test compound in contact with the cell expressing the receptor of the present invention and measuring the increase of the fluorescent intensity.

One specific example of such a screening method will be described below.

Cells expressing the receptor of the present invention are planted to a sterile cover glass for microscope. 2 days later, the culture fluid is replaced with HBSS obtained by suspending 4 mM Fura-2 AM (Dojindo Laboratories), and the cells are kept at room temperature for 2 hours and 30 minutes. The cover glass is washed with HBSS, and set on a cuvette. A tacrine compound, or the tacrine compound and a test compound, are added thereto, and the increase of the fluorescent intensity ratio at 505 nm is measured at an exciting wavelength of 340 nm and 380 nm by a fluorometer and compared.

FLIPR (Molecular Devices) may be used. Fluo-3 AM (Dojindo Laboratories) is added to a suspension of the cells expressing the receptor of the present invention and incorporated into the cells. Then, centrifugation is performed several times to remove the supernatant, and the cells are planted to a 96-well plate. The cells are set in an FLIPR device. In the same manner as in the case of Fura-2, a tacrine compound, or the tacrine compound and a test compound, are added. The increase of the fluorescent intensity ratio is measured and compared.

Alternatively, screening for a compound that alters the binding property between the tacrine compound and the receptor of the present invention may be performed as follows. A gene of a protein which emits light when the intracellular Ca ion concentration is increased (e.g., aequorin, etc.) is co-expressed in the cell expressing the receptor of the present invention. The screening is performed utilizing the phenomenon that the protein (e.g., aequorin, etc.) emits light by being a Ca-binding type when the intracellular Ca ion concentration is increased.

Cells expressing the receptor of the present invention, in which a gene of a protein which emits light when the intracellular Ca ion concentration is increased co-expressed, are planted to a 96-well plate, and a tacrine compound, or the tacrine compound and a test compound, are added thereto in substantially the same manner as described above. The increase of the fluorescent intensity ratio is measured and compared.

A test compound suppressing the increase of the fluorescent intensity caused by the tacrine compound can be selected as an antagonist candidate compound.

(7) When a receptor agonist is added to a cell expressing a receptor, the intracellular inositol triphosphoric acid concentration is increased. Using the intracellular inositol triphosphoric acid production activity caused by a tacrine compound in the cell expressing the receptor of the present invention, screening for a compound that alters the binding property between the tacrine compound and the receptor of the present invention can be performed.

Specifically, screening for a compound that alters the binding property between the tacrine compound and the receptor of the present invention is performed in the presence of labeled inositol, by measuring and comparing the inositol triphosphoric acid production activity, in the case where the tacrine compound is brought in contact with the cell expressing the receptor of the present invention, and in the case where the tacrine compound and a test compound are brought in contact with the cell expressing the receptor of the present invention. The inositol triphosphoric acid production activity is measured by a known method.

In this method, a test compound suppressing the inositol triphosphoric acid production activity can be selected as an antagonist candidate compound.

Alternatively, screening for an agonist may be performed by bringing only a test compound in contact with the cell expressing the receptor of the present invention and measuring the increase of the inositol triphosphoric acid production activity.

One specific example of such a screening method will be described below.

Cells expressing the receptor of the present invention are planted to a 24-well plate and cultured for 1 day. Then, the cells are cultured for 1 day in a medium supplemented with [myo-[2-$^3$H]inositol (2.5 μCi/well), and the cells are washed well with an inositol-free medium having radioactivity. A tacrine compound, or the tacrine compound and a test compound, are added thereto, 10% perchloric acid is added, and the reaction is stopped. The mixture is neutralized with a solution of 1.5 M potassium hydroxide and 60 mM HEPES, and passed through a column filled with 0.5 ml of AGI×8 resin (Bio-Rad). The column is then washed with 5 mM sodium tetraborate ($Na_2B_4O_7$) and 60 mM ammonium formate. The radioactivity eluted with 1 M ammonium formate and 0.1 M formic acid is measured by a liquid scintillation counter. Where the radioactivity when no tacrine compound is added is set to 0% and the radioactivity when the tacrine compound is added is set to 100%, the influence of the test compound on the binding between the tacrine compound and the receptor of the present invention is calculated.

A test compound realizing the inositol triphosphoric acid production activity of, for example, 50% or less can be selected as an antagonist candidate compound.

(8) Screening for a compound that alters the binding property between a tacrine compound and the receptor of the present invention can be performed by measuring the stimulating activity of the tacrine compound to the cell expressing the receptor of the present invention using a TRE-reporter gene vector.

DNA containing a TRE (TPA response element) is inserted at an upstream position of the reporter gene of a vector to obtain a TRE-reporter gene vector. In the cell expressing the receptor of the present invention having the TRE-reporter gene vector, the stimulation accompanying an increase of the intracellular calcium concentration induces the expression of the reporter gene mediated by the TRE and the production of a gene product (protein) of the reporter gene following the expression of the reporter gene. Namely, a change of the calcium amount in the cell to which the TRE-reporter gene vector has been transfected can be detected by measuring the enzyme activity of the reporter gene protein.

Specifically, screening for a compound that alters the binding property between the tacrine compound and the receptor of the present invention is performed by measuring and comparing the enzyme activity of the reporter gene protein, in the case where the tacrine compound is brought in contact with the cell expressing the receptor of the present invention to which the TRE-reporter gene vector has been transfected, and in the case where the tacrine compound and a test compound are brought in contact with the cell expressing the receptor of the present invention to which the TRE-reporter gene vector has been transfected.

Examples of the vector include PicaGene basic vector, PicaGene enhancer vector (Toyo Ink Mfg. Co., Ltd.), and the like. DNA containing TRE is inserted at, for example, a multi-cloning site at an upstream position of a reporter gene of such a vector, e.g., a luciferase gene to obtain a TRE-reporter gene vector.

In this method, a test compound suppressing the enzyme activity of the reporter gene protein caused by the tacrine compound can be selected as an antagonist candidate compound.

Alternatively, screening for an agonist may be performed by bringing only a test compound in contact with the cell expressing the receptor of the present invention to which the TRE-reporter gene vector has been transfected and measuring the increase, similar to that caused by the tacrine compound, of the luminescence amount.

A specific example of such a screening method will be described below. In the following example, luciferase is used as a reporter gene.

Cells expressing the receptor of the present invention to which a TRE-reporter gene (luciferase) has been transfected are planted to a 24-well plate at a ratio of $5 \times 10^3$ cells/well and cultured for 48 hours. The cells are washed with a Hanks buffer (pH7.4) containing 0.05% BSA and 20 mM HEPES (hereinafter, referred to simply as the "reaction buffer"). Then, 100 μM tacrine compound, or 100 μM tacrine compound and a test compound, are added thereto to allow reaction at 37° C. for 60 minutes. The cells are lysed in a cell lysing agent for PicaGene (Toyo Ink Mfg. Co., Ltd.) and a luminescent substrate (Toyo Ink Mfg. Co., Ltd.) is added to the solution. Light emission by luciferase is measured by a luminometer, a liquid scintillation counter, or a top counter. The luminescence amount by luciferase is measured and compared in the case where only the tacrine compound is added and in the case where 100 μM tacrine compound and the test compound are added.

The increase of the intracellular calcium amount caused by the tacrine compound increases the luminescence amount caused by luciferase. A compound suppressing the increase can be selected as an antagonist candidate compound.

Examples of the reporter gene include genes such as alkaline phosphatase, chloramphenicol acetyltransferase, β-galactosidase, and the like. The enzyme activity of such a reporter gene protein is measured in accordance with a known method or using a commercially available measuring kit. The activity of alkaline phosphatase is measured using, for example, Lumi-Phos 530 manufactured by Wako Pure Chemical Industries, Ltd.; the activity of chloramphenicol acetyltransferase is measured using, for example, FAST CAT chloramphenicol Acetyltransferase Assay Kit manufactured by Wako Pure Chemical Industries, Ltd.; and the activity of β-galactosidase is measured using, for example, Aurora Gal-XE manufactured by Wako Pure Chemical Industries, Ltd.

(9) A cell expressing the receptor of the present invention, when stimulated by a tacrine compound, activates MAP kinase and is proliferated. This reaction can be used to measure the stimulating activity of the tacrine compound to the cell expressing the receptor of the present invention, and thus screening for a compound that alters the binding property between the tacrine compound and the receptor of the present invention can be performed.

Specifically, screening for a compound that alters the binding property between the tacrine compound and the receptor of the present invention is performed by measuring and comparing the cell proliferation, in the case where the tacrine compound is brought in contact with the cell expressing the receptor of the present invention, and in the case where the tacrine compound and a test compound are brought in contact with the cell expressing the receptor of the present invention.

The proliferation of the cell expressing the receptor of the present invention may be measured by measuring, for example, MAP kinase activity, thymidine incorporation activity, ATP amount, number of cells, or the like.

Specifically, the MAP kinase activity is measured for comparison as follows. A tacrine compound, or the tacrine compound and a test compound, are added to the cell expressing the receptor of the present invention, and an MAP kinase fraction is obtained from the cell solution by immunoprecipitation using an anti-MAP kinase antibody. Then, the MAP kinase activity is measured by a known method, for example, using MAP Kinase Assay Kit and $\gamma$-$[^{32}P]$-ATP.

The thymidine incorporation activity is measured for comparison as follows. Cells expressing the receptor of the present invention are planted to a 24-well plate and cultured. A tacrine compound, or the tacrine compound and a test compound, are added thereto, and thymidine labeled with radioactivity (e.g., [methyl-$^3$H]-thymidine, etc.) is added thereto. The cells are lysed, and the radioactivity of the thymidine incorporated into the cells is counted by a liquid scintillation counter. Thus, the thymidine incorporation activity is measured.

The ATP amount is measured for comparison as follows. Cells expressing the receptor of the present invention are planted to a 96-well plate and cultured. A tacrine compound, or the tacrine compound and a test compound, are added thereto. The ATP amount in the cells is measured using, for example, CellTiter-Glo (Promega).

The number of cells is measured for comparison as follows. Cells expressing the receptor of the present invention are planted to a 24-well plate and cultured. A tacrine compound, or the tacrine compound and a test compound, are added thereto, and MTT (3-(4,5-dimethyl-2-thiazolyl)-2,5-diphenyl-2H-tetrazolium bromide) is added thereto. MTT is changed as a result of being incorporated into the cells and becomes MTT formazan. After the cells are lysed in an aqueous solution of isopropanol acidified with hydrochloric acid, and MTT formazan is measured by absorption at 570 nm and compared.

In this method, a test compound suppressing the proliferation of the cell expressing the receptor of the present invention can be selected as an antagonist candidate compound.

Alternatively, screening for an agonist may be performed by bringing only a test compound in contact with the cell expressing the receptor of the present invention and measuring the cell proliferation activity, similar to the cell proliferation activity caused by the tacrine compound.

One specific example of such a screening method, in which the thymidine incorporation activity is utilized, will be described below.

Cells expressing the receptor of the present invention are planted to a 24-well plate at a ratio of 5000 cells/well and cultured for 1 day. The cells are cultured in a serum-free medium to be starved. A tacrine compound, or the tacrine compound and a test compound, are added to the cells, and the cells are cultured for 24 hours. [methyl-$^3$H]-thymidine is added at a ratio of 0.015 MBq per well, and the cells are cultured for 6 hours. The cells are washed with PBS, methanol is added thereto, and the cells are left for 10 minutes. Then, 5% trichloroacetic acid is added and the cells are left for 15 minutes. The immobilized cells are washed with distilled water 4 times. The cells are lysed with a 0.3 N solution of sodium hydroxide, and the radioactivity in the solution is measured by a liquid scintillation counter.

A test compound suppressing the increase of the radioactivity when the tacrine compound is added can be selected as an antagonist candidate compound.

(10) A cell expressing the receptor of the present invention, when stimulated by a tacrine compound, activates the potassium channel and releases K ions outside the cell. This reaction can be used to measure the stimulating activity of the tacrine compound to the cell expressing the receptor of the present invention, and thus screening for a compound that alters the binding property between the tacrine compound and the receptor of the present invention can be performed.

Rb ions (rubidium ions), which is a congener of K ions, flow out of the cell through the potassium channel without being distinguished from the K ions. Using this, the stimulating activity of a tacrine compound to the cell expressing the receptor of the present invention is measured by incorporating Rb ($[^{86}Rb]$), which is a radioisotope, into the cell expressing the receptor of the present invention, and measuring the flow of $^{86}Rb$ (flow-out activity) flowing out by the stimulation caused by the tacrine compound.

Specifically, screening for a compound that alters the binding property between the tacrine compound and the receptor of the present invention is performed in the presence of $^{86}Rb$, by measuring and comparing the $^{86}Rb$ flow-out activity, in the case where the tacrine compound is brought in contact with the cell expressing the receptor of the present invention, and in the case where the tacrine compound and a test compound are brought in contact with the cell expressing the receptor of the present invention.

In this method, a test compound suppressing the increase of the $^{86}Rb$ flow-out activity caused by the tacrine compound can be selected as an antagonist candidate compound.

Alternatively, screening for an agonist may be performed by bringing only a test compound in contact with the cell expressing the receptor of the present invention and measuring the increase of the $^{86}Rb$ flow-out activity, similar to that caused by the tacrine compound, One specific example of such a screening method will be described below.

Cells expressing the receptor of the present invention are planted to a 24-well plate and cultured for 2 days. Then, the cells are kept warm for 2 hours in a medium containing 1 mCi/ml of $^{86}$RbCl. The cells are washed well with the medium to completely remove the $^{86}$RbCl in the outer solution. A tacrine compound, or the tacrine compound and a test compound, are added to the cells. 30 minutes later, the outer solution is recovered, and the radioactivity is measured by a γ counter and compared.

A test compound suppressing the increase of the $^{86}$Rb flow-out activity occurring as a result of the stimulation by the tacrine compound can be selected as an antagonist candidate compound.

(11) A cell expressing the receptor of the present invention reacts with a tacrine compound to change the extracellular pH. This reaction can be used to measure the stimulating activity of the tacrine compound to the cell expressing the receptor of the present invention, and thus screening for a compound that alters the binding property between the tacrine compound and the receptor of the present invention can be performed.

Specifically, screening for a compound that alters the binding property between the tacrine compound and the receptor of the present invention is performed by measuring and comparing an extracellular pH change, in the case where the tacrine compound is brought in contact with the cell expressing the receptor of the present invention, and in the case where the tacrine compound and a test compound are brought in contact with the cell expressing the receptor of the present invention.

The extracellular pH change is measured by, for example, Cytosensor device (Molecular Devices).

In this method, a test compound suppressing the extracellular pH change caused by the tacrine compound can be selected as an antagonist candidate compound.

Alternatively, screening for an agonist may be performed by bringing only a test compound in contact with the cell expressing the receptor of the present invention and measuring the extracellular pH change, similar to that caused by the tacrine compound.

One specific example of such a screening method will be described below.

Cells expressing the receptor of the present invention are cultured overnight in a capsule for Cytosensor device, and set in a chamber of the device. For 2 hours until the extracellular pH is stabilized, a RPMI1640 medium (Molecular Devices) containing 0.1% BSA is refluxed. After the pH is stabilized, a medium containing a tacrine compound, or the tacrine compound and a test compound, is refluxed on the cells. The pH change of the medium caused by the refluxing is measured and compared.

A test compound suppressing the extracellular pH change caused by the tacrine compound can be selected as an antagonist candidate compound.

(12) A haploid α-mating type (MATα) sex pheromone receptor Ste2 of yeast (*Saccharomyces cerevisiae*) is coupled to G protein Gpa1, and activates MAP kinase in response to sex pheromone α-mating factor. This is followed by activation of Far1 (cell-cycle arrest) and transcription activity factor Ste12. Ste12 induces the expression of various proteins (e.g., FUS1 involved in coupling). By contrast, controlling element Sst2 acts to suppress the above process. In this system, the following attempts have been made on a system of measuring reaction between a receptor agonist and a receptor: yeast having a receptor gene transfected thereto is created, and a signal transduction system in the yeast cells is activated by the stimulation provided by the receptor agonist; and the resultant proliferation or the like is used as an index (Trends in Biotechnology, 15, 487-494, 1997). Using the system of the yeast having a receptor gene transfected thereto, screening for a compound that alters the binding property between a tacrine compound and the receptor of the present invention can be performed.

One specific example of such a screening method will be described below.

Genes encoding Ste2 of MATα yeast and Gpa1 are removed, and a gene of the receptor of the present invention and a gene encoding Gpa1-Gai2 fused protein are transfected. A gene encoding Far1 is removed so as not to cause cell-cycle arrest, and the gene encoding Sst2 is removed to improve the response sensitivity to the tacrine compound. FUS1-HIS3 gene obtained by binding FUS1 and histidine biosynthesis gene HIS3 bound is transfected. This genetic recombination operation can be performed in accordance with, for example, a method described in Molecular and Cellular Biology, 15, 6188-6195, 1995 but by replacing the somatostatin receptor type 2 (SSTR2) gene with the receptor of the present invention.

The transformed yeast thus constructed is highly reactive to the tacrine compound. As a result, MAP kinase is activated and histidine biosynthesis enzyme is synthesized. The histidine biosynthesis enzyme can be grown in a histidine-deficient medium.

Thus, screening for a compound that alters the binding property between the tacrine compound and the receptor of the present invention can be performed as follows. The above-described yeast expressing the receptor of the present invention (MATα yeast obtained by removing genes encoding Ste2 and Gpa1, introducing a gene of the receptor of the present invention and a gene encoding Gpa1-Gai2 fused protein, removing genes encoding Far1 and Sst2, and introducing FUS1-HIS3 gene) is cultured in a histidine-deficient medium. A tacrine compound, or the tacrine compound and a test compound, are brought in contact with the yeast, and the growth of the yeast is measured and compared.

In this method, a test compound suppressing the growth of the yeast can be selected as an antagonist candidate compound.

Alternatively, screening for an agonist may be performed by bringing only a test compound in contact with the yeast expressing the receptor of the present invention and measuring the growth of the yeast, similar to that caused by the tacrine compound.

One specific example of such a screening method will be described below.

Yeast expressing the receptor of the present invention is cultured overnight in a completely synthesized liquid medium, and the resultant yeast is added to a lysed agar medium deprived of histidine to provide a concentration of $2 \times 10^4$ cells/ml. The yeast is then planted to a 9×9 cm square laboratory dish. After the agar is solidified, a sterile paper filter immersed with a tacrine compound, or the tacrine compound and a test compound, is put on the surface of the agar, and the yeast is cultured at 30° C. for 3 days. The influence of the test compound is found by comparing the growth of the yeast around the paper filter in the case where the paper filter is immersed with only the tacrine compound, and in the case where the paper filter is immersed with the tacrine compound and the test compound. Alternatively, the following may be performed. A tacrine compound is added to the agar medium deprived of histidine, and yeast is cultured in the medium with a sterile paper immersed only with the test compound being put thereon. Thus, it may be observed that the growth of the yeast on the surface of the dish is influenced by the area around the paper filter.

A test compound suppressing the growth of the yeast can be selected as an antagonist candidate compound.

(13) When RNA of a gene for the receptor of the present invention is injected to *Xenopus laevis* oocyte and the oocyte is stimulated by a tacrine compound, the intracellular calcium concentration is increased to generate a calcium-activated chloride current. This can be regarded as a change of the membrane potential (this is also true when the K ion concentration gradient is changed). The above-described reaction caused by the tacrine compound in the *Xenopus laevis* oocyte having the receptor of the present invention transfected thereto can be used to measure the stimulating activity of the tacrine compound to the cell expressing the receptor of the present invention, and thus screening for a compound that alters the binding property between the tacrine compound and the receptor of the present invention can be performed.

Specifically, screening for a compound that alters the binding property between the tacrine compound and the receptor of the present invention is performed by measuring and comparing a cell membrane potential change, in the case where the tacrine compound is brought in contact with the *Xenopus laevis* oocyte having RNA of the gene for the receptor of the present invention transfected thereto, and in the case where the tacrine compound and a test compound are brought in contact with the *Xenopus laevis* oocyte having RNA of the gene for the receptor the present invention transfected thereto.

In this method, a test compound suppressing the cell membrane potential change can be selected as an antagonist candidate compound.

Alternatively, screening for an agonist may be performed by bringing only a test compound in contact with the *Xenopus laevis* oocyte having RNA of the gene for the receptor the present invention transfected thereto and measuring the cell membrane potential change, similar to that caused by the tacrine compound.

One specific example of such a screening method will be described below.

An oocyte lump taken from female *Xenopus laevis* immobilized by ice-cooling is treated with collagenaze (0.5 mg/ml) dissolved in MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH7.4) at 19° C. for 1 to 6 hour(s) at 150 rpm until the oocyte lump is loosened. The oocyte is washed 3 times by replacing the outer solution with MBS solution, and polyA addition cRNA (50 ng/50 nl) of a gene for the receptor of the present invention is micro-injected to the oocyte using a micromanipulator.

mRNA of a gene for the receptor of the present invention may be prepared from tissues or cells, or transcribed in vitro from plasmid. mRNA of the gene for the receptor of the present invention is cultured at 20° C. for 3 days in MBS solution, and put in a pit of a voltage clamp device in which a ringer solution is flowing. A microscopic glass electrode for fixing the potential and a microscopic glass electrode for measuring the potential are pierced into the oocyte while the negative electrode is put outside the oocyte. When the potential is stabilized, the ringer solution containing a tacrine compound, or the tacrine compound and a test compound, is flown to record the potential change. The influence of the test compound is found by comparing the cell membrane potential change in the *Xenopus laevis* oocyte to which RNA of the gene for the receptor of the present invention has been transfected, in the case where the ringer solution contains only the tacrine compound, and in the case where the ringer solution contains the tacrine compound and the test compound.

A test compound suppressing the cell membrane potential change can be selected as an antagonist candidate compound.

In the above system, when the change amount of the potential is increased, the potential can be measured more easily. Therefore, polyA addition RNA of a gene for the receptor of various types of G protein gene may be transfected. Instead of the membrane potential change, the luminescence amount may be measured by co-injecting polyA addition RNA of a gene for the protein which emits light in the presence of calcium (e.g., aequorin, etc.).

A kit for screening a compound or a salt thereof that alters the binding property between a tacrine compound and the receptor of the present invention contains the receptor of the present invention, a cell or a membrane fraction of the cell containing the receptor of the present invention, and the tacrine compound.

Examples of the screening kit of the present invention include the following.

1. Reagent for Screening (i) Measuring Buffer and Wash Buffer

Hanks' balanced salt solution (manufactured by Invitrogen) is supplemented with 0.05% bovine serum albumin (manufactured by Sigma, Inc.)

The solution may be sterilized by filtration through a 0.45 μm filter and stored at 4° C., or may be prepared at use.

(ii) Standard Receptor of the Present Invention

CHO cells in which the receptor of the present invention has been expressed are passaged in a 12-well plate at a density of $5 \times 10^5$ cells/well and cultured at 37° C. under 5% $CO_2$ and 95% air for 2 days.

(iii) Labeled Ligand

A tacrine compound labeled with a radioisotope such as [$^3$H], [$^{125}$I], [$^{14}$C], [$^{32}$P], [$^{33}$P], [$^{35}$S] or the like is dissolved in an appropriate solvent or buffer, stored at 4° C. or −20° C., and diluted to 1 μM with the measuring buffer upon use.

(iv) Standard Ligand Solution

A tacrine compound is dissolved in PBS containing 0.1% bovine serum albumin (manufactured by Sigma, Inc.) so as to have a concentration of 1 mM, and stored at −20° C.

2. Measuring Method (i) The CHO cells, which have been cultured in the 12-well culture plate with the receptor of the present invention being expressed, are washed twice with 1 ml of the measuring buffer, and 490 μl of the measuring buffer is added to each well.

(ii) After adding 5 μl of a $10^{-3}$ to $10^{-10}$ M test compound solution thereto, 5 μl of the labeled tacrine compound is added thereto to allow reaction at room temperature for 1 hour. In order to determine the amount of non-specific binding, 5 μl of $10^{-3}$ M tacrine compound is added in place of the test compound.

(iii) The reaction solution is removed, and the wells are washed 3 times with 1 ml of the wash buffer. The labeled tacrine compound bound to the cells is dissolved in 0.2 N NaOH-1% SDS, and mixed with 4 ml of liquid scintillator A (manufactured by Wako Pure Chemical Industries, Ltd.)

(iv) The radioactivity is measured using a liquid scintillation counter (manufactured by Beckman Co.), and the percent maximum binding (PMB) is calculated by the equation below.

$$PMB=[(B-NSB)/(B_0-NSB)]\times 100$$

| | |
|---|---|
| PMB | Percent maximum binding |
| B | Value obtained in the presence of a test compound |
| NSB | Non-specific binding |
| $B_0$ | Maximum binding |

A compound or a salt thereof which can be obtained by the screening method or the screening kit according to the present invention can alter the binding property between a tacrine compound and the receptor of the present invention, or can promote or inhibit the activities of the receptor of the present invention. Specifically, such a compound is (i) a compound or a salt thereof having cell stimulating activities mediated by the receptor of the present invention (agonist for the receptor of the present invention), (ii) a compound or a salt thereof having no such activities (antagonist to the receptor of the present invention), (iii) a compound promoting the binding between the receptor of the present invention and the tacrine compound, (iv) a compound inhibiting the binding between the receptor of the present invention and the tacrine compound, or the like. Such a compound is, for example, selected from peptide, protein, non-peptide compound, synthetic compound, fermentation product, cell extract, plant extract, animal tissue extract, plasma, etc. Such a compound may be novel or known.

Examples of the salt of such a compound may be substantially the same as the examples of the salt of the receptor of the present invention described above.

Whether a compound is an agonist for, or an antagonist to, the receptor of the present invention may be evaluated in accordance with, for example, the method (i) or (ii) below.
(i) Binding assay shown by the screening method (a) to (c) described above is performed to obtain a compound that alters the binding property (especially inhibits the binding) between the tacrine compound and the receptor of the present invention. Then, it is determined by measurement if the compound has the above-described cell stimulating activities described above mediated by the receptor of the present invention. A compound or a salt thereof which has the cell stimulating activities is an agonist for the receptor of the present invention (agonist), whereas a compound or a salt thereof having no such activities is an antagonist to the receptor of the present invention (antagonist).
(ii)(a) A test compound is brought in contact with a cell containing the receptor of the present invention, and the cell stimulating activities mediated by the receptor of the present invention are measured. A compound or a salt thereof having the cell stimulating activities is an agonist for the receptor of the present invention.
(b) The cell stimulating activities mediated by the receptor of the present invention are measured and compared between the case where the tacrine compound is brought in contact with a cell containing the receptor of the present invention and the case where the tacrine compound and a test compound are brought in contact with a cell containing the receptor of the present invention. A compound or a salt thereof which can decrease the cell stimulating activities caused by a compound activating the receptor of the present invention is an antagonist to the receptor of the present invention.

As described above, the receptor of the present invention is expressed in breast cancer derived cell line. The expression progress or ligand-induced activation of the receptor suppresses the activation of MAP kinase in the cells, and thus apoptosis is induced (Endocrinology, 143, 3376-3384, 2002; Mol. Endocrinol., 16, 70-84, 2002).

Accordingly, the agonist for the receptor of the present invention and a tacrine compound are useful as a safe and low toxicity pharmaceutical agent, for example, a preventive/therapeutic agent, a cell apoptosis promoter, a cell proliferation inhibitor or the like for cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.).

The antagonist to the receptor according to the present invention can suppress the physiological actions of the receptor of the present invention (e.g., myocardial apoptosis after ischemic reperfusion, etc.), and therefore is useful as a safe and low toxicity agent, for example, as a preventive/therapeutic agents for heart diseases (e.g., cardiomyopathy, cardiac infarction, heart failure, angina pectoris, etc.), a preventive/therapeutic agent for myocardial cell apoptosis, or the like.

A compound promoting the binding between the receptor of the present invention and a tacrine compound is useful as a safe and low toxicity pharmaceutical agent, for example, a preventive/therapeutic agent, a cell apoptosis promoter, a cell proliferation inhibitor or the like for cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.).

A compound inhibiting the binding between the receptor of the present invention and a tacrine compound is useful as a safe and low toxicity pharmaceutical agent, for example, as a preventive/therapeutic agent for heart diseases (e.g., cardiomyopathy, cardiac infarction, heart failure, angina pectoris, etc.), a preventive/therapeutic agent for apoptosis of myocardial cells, or the like.

A compound or a salt thereof which can be obtained by the screening method or the screening kit according to the present invention is selected from, for example, peptide, protein, non-peptide compound, synthetic compound, fermentation product, cell extract, plant extract, animal tissue extract, plasma, and the like; and is a compound altering the binding property between the receptor of the present invention and a tacrine compound, a compound promoting or inhibiting the activities or functions of the receptor of the present invention, a compound promoting or inhibiting the expression (increasing or decreasing the expression amount) of the gene of the receptor of the present invention, or the like.

Examples of the salt of such a compound may be substantially the same as the examples of the salt of the receptor of the present invention described above.

Any of such compounds or a salt thereof can be used as any of the above-described pharmaceutical agents (as any of the preventive/therapeutic agents) in accordance with a usual procedure.

Any of such compounds or a salt thereof can be used, for example, orally in the form of tablets which may be sugar coated if necessary, capsules, elixirs, microcapsules etc., or parenterally in the form of injectable preparations such as sterile solutions, suspensions and the like in water or with other pharmaceutically acceptable liquids. These oral or parenteral preparations can be produced by mixing any of the above-described compounds or a salt thereof with a physiologically acceptable carrier, a flavoring agent, an excipient, a vehicle, an antiseptic agent, a stabilizer, a binder, etc. in a generally accepted unit dosage form as being required for the pharmaceutical preparations. The amount of the active components in the preparations is controlled such that each active component is obtained in an appropriate dose within a given range.

Examples of additives miscible with tablets, capsules, etc. include a binder such as gelatin, corn starch, tragacanth, gum Arabic, etc.; an excipient such as crystalline cellulose, etc.; a swelling agent such as corn starch, gelatin and alginic acid, etc.; a lubricant such as magnesium stearate, etc.; a sweetening agent such as sucrose, lactose and saccharin, etc.; a flavoring agent such as peppermint, akamono oil, cherry, etc.; and the like. In the case where the unit dosage is in the form of capsules, liquid carriers such as oils and fats may further be used together with the additives described above. A sterile composition for injection may be formulated by a conventional procedure used to produce pharmaceutical compositions, e.g., by dissolving or suspending the active ingredients in a vehicle such as water for injection or a naturally occurring vegetable oil such as sesame oil, coconut oil, etc. to prepare the pharmaceutical composition.

Examples of an aqueous medium for injection include physiological saline, an isotonic solution containing glucose and other auxiliary agents (e.g., D-sorbitol, D-mannitol, sodium chloride, etc.), and the like. Such an aqueous medium for injection may be used in combination with an appropriate dissolution aid such as an alcohol (e.g., ethanol, etc.), a polyalcohol (e.g., propyleneglycol, polyethyleneglycol. etc.), a nonionic surfactant (e.g., polysorbate 80™, HCO-50, etc.) or the like. Examples of an oily medium for injection include sesame oil, soybean oil, and the like. Such an oily medium may be used in combination with a dissolution aid such as benzyl benzoate, benzyl alcohol, or the like. Any of the above-described compounds or a salt thereof may be combined with a buffering agent (e.g., phosphate buffer, sodium acetate buffer, etc.), a soothing agent (e.g., benzalkonium chloride, procaine hydrochloride, etc.), a stabilizer (e.g., human serum albumin, polyethyleneglycol, etc.), a preservative (e.g., benzylalcohol, phenol, etc.), an antioxidant, or the like. The prepared injection liquid is usually put into an appropriate ampule or the like.

The pharmaceutical preparations thus obtained are safe and low in toxicity, and therefore can be administered to, for example, human or warm blooded animals (e.g., mouse, rat, rabbit, sheep, swine, bovine, horse, chicken, cat, dog, monkey, chimpanzee, etc.).

The dose of the compound or a salt thereof varies depending on the action thereof, target disease, administration target, symptom, administration route or the like.

For example, a daily dose of the compound for a patient with breast cancer (body weight: 60 kg) is about 0.1 to about 100 mg, preferably about 1.0 to about 50 mg, and more preferably about 1.0 to about 20 mg by oral administration. In the case of parenteral administration, for example, administration in the form of injection, it is advantageous to administer the compound to a patient with breast cancer (body weight: 60 kg) by intravenous injection in a daily dose of about 0.01 to about 30 mg, preferably about 0.1 to about 20 mg, and more preferably about 0.1 to about 10 mg. For other animal species, a corresponding dose as converted based on 60 kg of the body weight can be administered.

The above-listed pharmaceutical agents maybe co-used with other drugs, for example, an alkylating agent (e.g., cyclophosphamide, busulfan, merphalan, etc.), an antimetabolism agent (e.g., cytarabine, 6-mercaptopurine, methotrexate, 5-fluorouracil, etc.), an anticancer antibiotic (e.g., daunorubicin, doxorubicin, pirarubicin, mitoxantron, idarubicin, mitomycin, adriamycin, etc.), a plant derived anticancer agent (e.g., vincristine, vindesine, taxol, etoposide, etc.), an enzyme preparation (e.g., L-asparaginase, etc.), an adrenocortical hormone agent (e.g., prednisolone, prednisone, dexamethasone, cortisone acetate, etc.), an estrogen drug (e.g., estradiol, ethinyl estradiol, fosfestrol, chlorotrianisene, etc.), an anti-estrogen drug (e.g., epithiostanol, mepitiostane, tamoxifen, clomifene, etc.), a progesterone drug (e.g., hydroxyprogesterone caproate, dydrogesterone, medroxyprogesterone, norethisterone, norethindrone, etc.), an LHRH derivative (e.g., leuprorelin acetate, etc.), cisplatin, carboplatin, transretinoic acid, interferon α, imatinib, or the like. Owing to the co-use, the dose of such a pharmaceutical agent and (or) drug can be reduced without reducing the anticancer effect required for the prevention and (or) therapy. Therefore, the side effects (e.g., disorder of normal cells, etc.) of the pharmaceutical agent and (or) drug can be alleviated without reducing the preventive and (or) therapeutic effect. There is no limitation on the administration period, and these pharmaceutical agents or drugs can be administrated to the target at the same time or some time apart. The dose of administration may be appropriately selected based on the clinically used dose. The ratio of the above-described compound and the co-used drug may be appropriately selected in accordance with the administration target, administration route, disease, symptom, compound/drug combination, or the like.

[2] Cancer Preventive/Therapeutic Agents Containing a Tacrine Compound

A tacrine compound is a ligand of the receptor of the present invention, which is expressed by breast cancer derived cell line. The expression progress or ligand-induced activation of the receptor suppresses the activation of MAP kinase in the cells, and thus apoptosis is induced.

Accordingly, a tacrine compound is useful as a safe and low toxicity pharmaceutical agent, for example, a preventive/therapeutic agent, a cell apoptosis promoter, a cell proliferation inhibitor or the like for cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.).

A tacrine compound can be used as any of the above-described pharmaceutical agents (as any of the preventive/therapeutic agents) in accordance with a usual procedure.

Any of such compounds can be used, for example, orally in the form of tablets which may be sugar coated if necessary, capsules, elixirs, microcapsules etc., or parenterally in the form of injectable preparations such as sterile solutions, suspensions and the like in water or with other pharmaceutically acceptable liquids. These oral or parenteral preparations can be produced by mixing any of the above-described compounds or a salt thereof with a physiologically acceptable carrier, a flavoring agent, an excipient, a vehicle, an antiseptic agent, a stabilizer, a binder, etc. in a generally accepted unit dosage form as required for the pharmaceutical preparations. The amount of the active components in the preparations is controlled such that each active component is obtained in an appropriate dose within a given range.

Examples of additives miscible with tablets, capsules, etc. include a binder such as gelatin, corn starch, tragacanth, gum Arabic, etc.; an excipient such as crystalline cellulose, etc.; a swelling agent such as corn starch, gelatin and alginic acid, etc.; a lubricant such as magnesium stearate, etc.; a sweetening agent such as sucrose, lactose and saccharin, etc.; a flavoring agent such as peppermint, akamono oil, cherry, etc.; and the like. In the case where the unit dosage is in the form of capsules, liquid carriers such as oils and fats may further be used together with the additives described above. A sterile composition for injection may be formulated by a conventional procedure used to produce pharmaceutical compositions, e.g., by dissolving or suspending the active ingredients in a vehicle such as water for injection or a naturally occurring vegetable oil such as sesame oil, coconut oil, etc. to prepare the pharmaceutical composition.

Examples of an aqueous medium for injection include physiological saline, an isotonic solution containing glucose and other auxiliary agents (e.g., D-sorbitol, D-mannitol, sodium chloride, etc.), and the like. Such an aqueous medium for injection may be used in combination with an appropriate dissolution aid such as an alcohol (e.g., ethanol, etc.), a polyalcohol (e.g., propyleneglycol, polyethyleneglycol. etc.), a nonionic surfactant (e.g., polysorbate 80™, HCO-50, etc.) or the like. Examples of an oily medium for injection include sesame oil, soybean oil, and the like. Such an oily medium may be used in combination with a dissolution aid such as benzyl benzoate, benzyl alcohol, or the like. Any of the above-described compounds or a salt thereof may be combined with a buffering agent (e.g., phosphate buffer, sodium acetate buffer, etc.), a soothing agent (e.g., benzalkonium chloride, procaine hydrochloride, etc.), a stabilizer (e.g., human serum albumin, polyethyleneglycol, etc.), a preservative (e.g., benzylalcohol, phenol, etc.), an antioxidant, or the like. The prepared injection liquid is usually put into an appropriate ampule or the like.

The pharmaceutical preparations thus obtained are safe and low in toxicity, and therefore can be administered to, for example, human or warm blooded animals (e.g., mouse, rat, rabbit, sheep, swine, bovine, horse, chicken, cat, dog, monkey, chimpanzee, etc.).

The dose of the compound or a salt thereof varies depending on the action thereof, target disease, administration target, symptom, administration route or the like.

For example, a daily dose of the compound for a patient with breast cancer (body weight: 60 kg) is about 0.1 to about 100 mg, preferably about 1.0 to about 50 mg, and more preferably about 1.0 to about 20 mg by oral administration. In the case of parenteral administration, for example, in the form of injection, it is advantageous to administer the compound to a patient with breast cancer (body weight: 60 kg) by intravenous injection in a daily dose of about 0.01 to about 30 mg, preferably about 0.1 to about 20 mg, and more preferably about 0.1 to about 10 mg. For other animal species, a corresponding dose as converted based on 60 kg of the body weight can be administered.

The above-listed pharmaceutical agents may be co-used with other drugs, for example, an alkylating agent (e.g., cyclophosphamide, busulfan, merphalan, etc.), an antimetabolism agent (e.g., cytarabine, 6-mercaptopurine, methotrexate, 5-fluorouracil, etc.), an anticancer antibiotic (e.g., daunorubicin, doxorubicin, pirarubicin, mitoxantron, idarubicin, mitomycin, adriamycin, etc.), a plant derived anticancer agent (e.g., vincristine, vindesine, taxol, etoposide, etc.), an enzyme preparation (e.g., L-asparaginase, etc.), an adrenocortical hormone agent (e.g., prednisolone, prednisone, dexamethasone, cortisone acetate, etc.), an estrogen drug (e.g., estradiol, ethinyl estradiol, fosfestrol, chlorotrianisene, etc.), an anti-estrogen drug (e.g., epithiostanol, mepitiostane, tamoxifen, clomifene, etc.), a progesterone drug (e.g., hydroxyprogesterone caproate, dydrogesterone, medroxyprogesterone, norethisterone, norethindrone, etc.), an LHRH derivative (e.g., leuprorelin acetate, etc.), cisplatin, carboplatin, transretinoic acid, interferon α, imatinib, or the like. Owing to the co-use, the dose of such a pharmaceutical agent and (or) drug can be reduced without reducing the anticancer effect required for the prevention and (or) therapy. Therefore, the side effects (e.g., disorder of normal cells, etc.) of the pharmaceutical agent and (or) drug can be alleviated without reducing the preventive and (or) therapeutic effect. There is no limitation on the administration period, and these pharmaceutical agents or drugs can be administrated to the target at the same time or some time apart. The dose of administration may be appropriately selected based on the clinically used dose. The ratio of the above-described compound and the co-used drug may be appropriately selected in accordance with the administration target, administration route, disease, symptom, compound/drug combination, or the like.

In the specification and the sequence listing, the codes of bases, amino acids, etc. are denoted in accordance with the IUPAC-IUB Commission on Biochemical Nomenclature or by the common codes used in the art, examples of which are shown below. For amino acids that may have an optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |
| Sec | selenocysteine |

Substituents, protecting groups and reagents frequently used in this specification are presented as the codes below.

| | |
|---|---|
| Me | methyl group |
| Et | ethyl group |
| Bu | butyl group |
| Ph | phenyl group |
| TC | thiazolidine-4(R)-carboxamido group |
| Tos | p-toluenesulfonyl |
| CHO | formyl |
| Bzl | benzyl |
| $Cl_2$-Bzl | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenyl |
| Trt | trityl |
| Bum | t-butoxymethyl |
| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dicyclohexylcarbodiimide |

The sequence identification numbers in the sequence listing in this specification show the following sequences.

[SEQ ID NO: 1]
This shows the amino acid sequence of the human GPR30.
[SEQ ID NO: 2]
This shows the amino acid sequence of the rat GPR30.
[SEQ ID NO: 3]
This shows the amino acid sequence of the mouse GPR30.
[SEQ ID NO: 4]
This shows the amino acid sequence of the human GPR30.
[SEQ ID NO: 5]
This shows the nucleotide sequence of cDNA encoding the human GPR30 containing the amino acid sequence represented by SEQ ID NO: 1.
[SEQ ID NO: 6]
This shows the nucleotide sequence of cDNA encoding the rat GPR30.
[SEQ ID NO: 7]
This shows the nucleotide sequence of cDNA encoding the mouse GPR30.
[SEQ ID NO: 8]
This shows the nucleotide sequence of cDNA encoding the human GPR30 containing the amino acid sequence represented by SEQ ID NO: 4.

EXAMPLES

Hereinafter, the present invention will be described more specifically by way of reference examples and examples, which do not limit the present invention in any way.

Reference Example 1

Production of Human GPR30 Expression CHO Cells

First, cDNA of human GPR30 (SEQ ID NO: 5) was cloned by a known PCR method and inserted into pAKKO1.11H expression vector (Biochemica et Biophysica Acta, 1219 (1994) 251-259). Structures of plasmids were checked with restriction enzyme treatment and sequence analysis, and a plasmid having a correct structure was used as plasmid pAK-hGPR30 for CHO cell expression.

The plasmid pAK-hGPR30 was transduced by electroporation into CHO/dhfr cells (American Type Culture Collection) as follows. First, the plasmid pAK-hGPR30 was treated with restriction enzyme AhdI. To a cuvette for electroporation, $5 \times 10^6$ CHO/dhfr$^-$ cells suspended in 500 μl of PBS and 5 μg of plasmid DNA lysed in 10 μl of TE buffer were added. The resultant substance was kept still on ice for 5 minutes, and then subjected to electroporation under the conditions of 0.25 V and 960 μF. The resultant substance was kept still on ice for 5 minutes. Then, the entire amount of the CHO/dhfr$^-$ cells was planted in a T75 flask, and cultured in a nucleic acid-containing MEMalpha medium (Invitrogen) containing 10% fetal bovine serum (BIO WHITTAKER) at 37° C. in 5% carbon dioxide for 1 day. The cells were dispersed by trypsin treatment and recovered from the flask. 200 or 500 cells were planted on each 96-well plate, and started to be cultured in dialyzed 10% fetal bovine serum (JRH BIOSCIENCE) in a nucleic acid-free MEMalpha medium (Invitrogen) containing 50 μg/ml of gentamicin at 37° C. in 5% carbon dioxide. Transformed CHO cells having plasmid transfected thereto grew in the medium, but transformed CHO cells with no plasmid gradually died. In 8 to 10 days after the start of culturing, wells in the 96-well plates having one well in which one colony had grown were selected, and about 48 colonies of the transformed CHO cells were selected. RNA was recovered from the selected cells using a commercially available RNA isolation kit. Then, transformed CHO cells expressing human GPR30 (hereinafter, referred to simply as "human GPR30 cells") at a high ratio were selected by a known TaqMan RT-PCR method.

Reference Example 2

Production of Rat GPR30 Expression CHO Cells

Rat GPR30 has been reported as GPR41 in Biochemical Biophysical Research Communications, 234, 190-193, 1997).

Rat GPR30 receptor cDNA (SEQ ID NO: 6) was cloned by a known PCR method and inserted into pAKKO1.11H expression vector (Biochemica et Biophysica Acta, 1219, 251-259, 1994). Structures of plasmids were checked with restriction enzyme treatment and sequence analysis, and a plasmid having a correct structure was used as plasmid pAK-rGPR30 for CHO cell expression.

The plasmid pAK-rGPR30 was transduced by electroporation into CHO/dhfr⁻ cells (American Type Culture Collection) in the method described in REFERENCE EXAMPLE 1, and transformed CHO cells expressing rat GPR30 (hereinafter, referred to simply as "rat GPR30 cells") at a high ratio were selected.

Example 1

(1) Measurement of Agonist Activities of Human GPR30 and Rat GPR30 by FLIPR

The human GPR30 cells and the rat GPR30 cells obtained in the above reference examples were separately suspended in a medium (10% d FBS-DMEM) so as to have a concentration of $15 \times 10^4$ cells/ml. 200 µl of each type of cells was planted in each well of a 96-well plate for FLIPR (Black plate clear bottom, Coster) using an 8-channel pipette ($3.0 \times 10^4$ cells/200 µl/well) and cultured in a 5% $CO_2$ incubator at 37° C. overnight (hereinafter, referred to as the "cell plate") before use. 20 ml of H/HBSS, 200 µl of 250 mM Probenecid, and 200 µl of fetal bovine serum (FBS) were mixed. 2 vials (50 µg) of Fluo 3-AM (Dojindo Laboratories) were lysed in 40l of dimethylsulfoxide and 40 µl of 20% Pluronic acid (Molecular Probes), and the resultant substance was added to H/HBSS-Probenecid-FBS and mixed. Then, the resultant mixture was divided into units of 100 µl and put to each well of the cell plate deprived of the culture fluid using an 8-channel pipette, and incubated in a 5% $CO_2$ incubator at 37° C. for 1 hour (colorant loading). 8 µl of a tacrine solution (Aldrich Chemical Company) of various concentrations was added to 259 µl of H/HBSS containing 2.5 mM Probenecid, 0.1% CHAPS and 0.1% BSA, and diluted. The resultant substance was transferred to a 96-well plate for FLIPR (V-Bottom plate, Coster) (hereinafter, this plate will be referred to as the "sample plate"). After the colorant loading to the cell plate was finished, the cell plate was washed 5 times with a wash buffer containing H/HBSS and 2.5 mM Probenecid using a plate washer (Molecular Devices) to leave 100 µl of wash buffer. The cell plate and the sample plate were set in an FLIPR (501 of sample was transferred from the sample plate to the cell plate by the FLIPR), and a change of the fluorescent intensity was measured over-time. Thus, the intracellular calcium ion concentration increase activity was measured.

The results are shown in FIG. 1 through FIG. 4.

This has revealed that the intracellular calcium ion concentration in the human GPR30 cells and the rat GPR30 cells is increased in a concentration-depending manner by tacrine stimulation.

(2) Method for Examining the Activities of a Test Compound Using FLIPR

The human GPR30 cells obtained in the above reference examples are suspended in a medium (10% d FBS-DMEM) so as to have a concentration of $15 \times 10^4$ cells/ml. 200 µl of the cells is planted in each well of a 96-well plate for FLIPR (Black plate clear bottom, Coster) using an 8-channel pipette ($3.0 \times 10^4$ cells/200 µl/well) and cultured in a 5% $CO_2$ incubator at 37° C. overnight (hereinafter, referred to as the "cell plate") before use for assay 20 ml of H/HBSS, 200 µl of 250 mM Probenecid, and 200 µl of fetal bovine serum (FBS) are mixed. 2 vials (50 µg) of Fluo 3-AM (Dojindo Laboratories) are lysed in 40 µl of dimethylsulfoxide and 401 of 20% Pluronic acid (Molecular Probes), and the resultant substance is added to H/HBSS-Probenecid-FBS and mixed. Then, the resultant mixture is divided into units of 100 µl and put to each well of the cell plate deprived of the culture fluid using an 8-channel pipette, and incubated in a 5% $CO_2$ incubator at 37° C. for 1 hour (colorant loading).

A solution containing a test compound is added to H/HBSS containing 2.5 mM Probenecid and 0.1% CHAPS, and diluted. The resultant substance is transferred to a 96-well plate for FLIPR (V-Bottom plate, Coster) (hereinafter, this plate will be referred to as the "sample plate"). After the colorant loading to the cell plate is finished, the cell plate is washed 5 times with a wash buffer containing H/HBSS and 2.5 mM Probenecid using a plate washer (Molecular Devices) to leave 100 µl of wash buffer. The cell plate and the sample plate are set in an FLIPR (50 µl of sample is transferred from the sample plate to the cell plate by the FLIPR), and a change of the fluorescent intensity is measured over-time. Thus, the intracellular calcium ion concentration increase activity is measured. An experiment substantially the same as above may be performed using CHO cell lines which do not express GPR30 to search for a compound specifically increasing the intracellular calcium ion concentration of the GPR30 expression CHO cells.

Example 2

Transient Expression of G Protein-Coupled Receptor Protein Expression Plasmid and Reporter Plasmid in Host Cell (HeLa)

*E. coli* JM109 was transformed using plasmid pAK-hGPR30 described in REFERENCE EXAMPLE 1, and the resultant colonies were isolated and cultured. Thereafter, large scale plasmid preparation was carried out using QIAGEN Plasmid Maxi Kit (Qiagen). Separately, a reporter plasmid of pSRE-Luc (Invitrogen) ligated with a luciferase gene as a reporter at a downstream position of a serum response element (SRE), and expression vector plasmids for human GαoA, human Gβ1 and human Gγ2, which are each a kind of G proteins, were prepared in substantially the same manner.

HeLa cells were used as host cells for transfecting the G protein-coupled receptor protein expression plasmid pAK-hGPR30 and the reporter plasmids. The cells were planted on a 384-well assay plate (COSTAR 3704) at a ratio of 4000 cells/well in a culture volume of 25 µl, and incubated overnight. As the medium, DMEM (Invitrogen) supplemented with 10% fetal bovine serum and 1% MEM non-essential amino acids solution (DMEM/NEAA) was used.

Each plasmid was diluted to a concentration of 240 ng/µl. Plasmids were added to 250 µl of Opti-MEM-I (Invitrogen) at a ratio of 1 µl of pAK-hGPR30, 9 µl of the reporter plasmid, and 1 µl of each of the G protein expression plasmids for GαoA, Gβ1 and Gγ2. For an experiment control, 1 µl of the plasmid of expression vector pAKKO-1.11H containing no DNA encoding the receptor protein was used instead of the receptor expression plasmid. Each resultant substance was mixed with 250 µl of Opti-MEM-I supplemented with 10 µl of Lipofectamine™ 2000 Reagent (Invitrogen) in an equal volume to form a liposome-plasmid composite in accordance with the procedure described in the attached manual. Each of these composites was added to the culture medium of HeLa cells at a ratio of 5 μl/well to introduce the plasmid, and then the resultant substance was cultured overnight at 37° C. under 5% $CO_2$.

(2) Detection of Ligand Activities by Reporter Assay

The Hela cells prepared in section (1) above were washed twice with fetal bovine serum-free DMEM/NEAA (assay medium) and cultured at 37° C. under 5% $CO_2$ for 2 hours. Tacrine (Aldrich Chemical Company) washed once in an assay medium and dissolved in an assay medium containing 0.05% CHAPS was added to the cells in each well. A sample was added thereto and incubated at 37° C. under 5% $CO_2$ for 4 hours to induce the promotion of transcription/translation of the reporter gene, which was derived from intracellular signal transduction caused by the agonist activity of the ligand mediated by the receptor. After the incubation was completed, the medium in each well was removed and 8 μl of PicaGene LT 2.0 (Toyo Ink Mfg. Co., Ltd.) as a substrate for measuring luciferase activity was added to each well. After the cells were lysed and thoroughly mixed with the substrate, the chemiluminescence level corresponding to the expression induction level of the reporter gene in each well was measured on a plate reader (EnVision™, Perkin Elmer).

Figure 5:
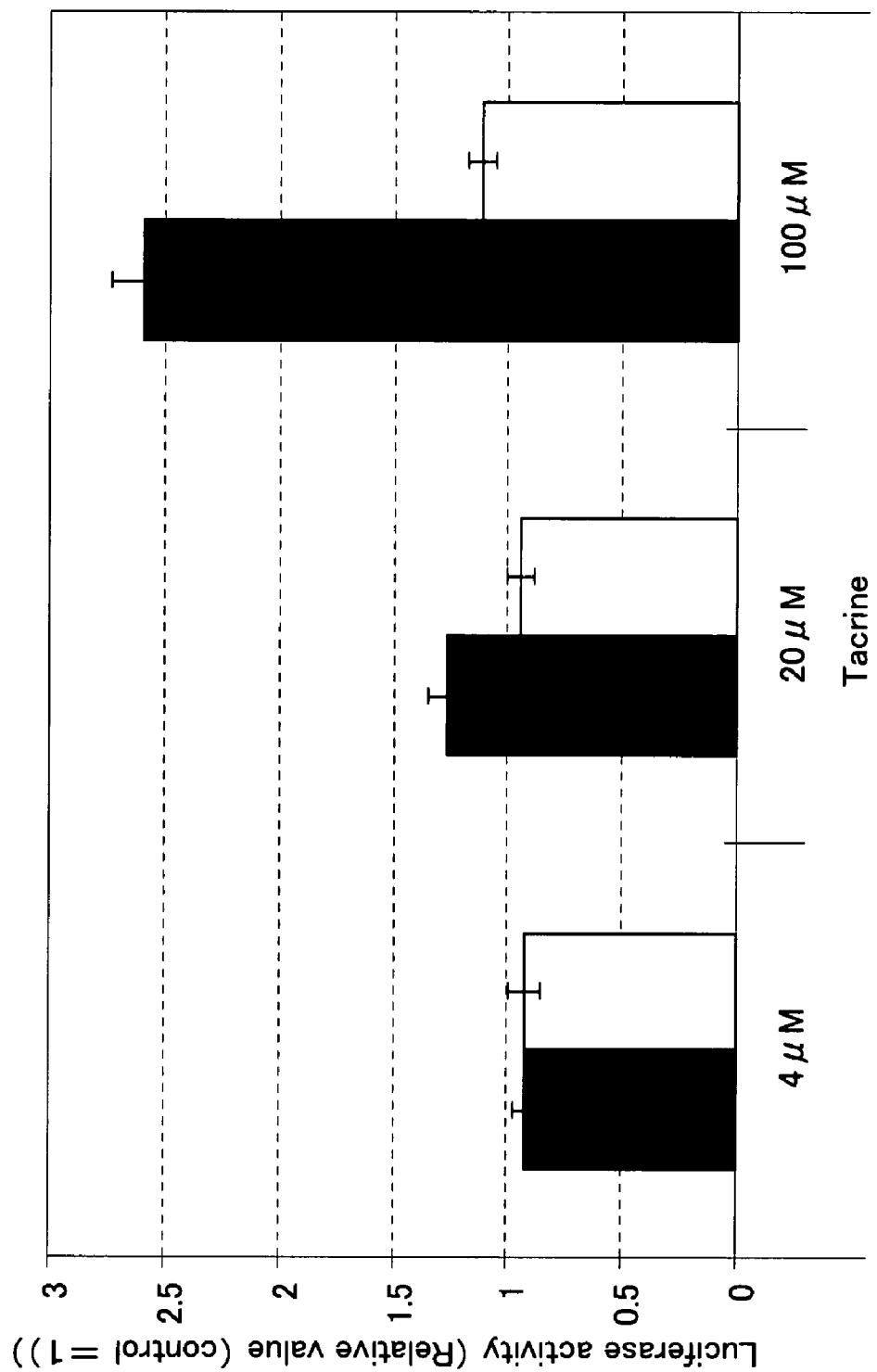
FIG. 5 shows the luciferase activity of HeLa cells expressing human GPR30 and HeLa cells not expressing human GPR30 with respect to tacrine of various concentrations. In the figure, ■ represents the result with the HeLa cells expressing human GPR30, and □ represents the result with the HeLa cells not expressing human GPR30.

As a result, as shown in FIG. 5, a significant increase of luciferase activity was detected in the GPR30 expression cells by the addition of tacrine (100 μM). By contrast, no significant activity increase was detected with the pAKKO-1.11H-transfected cells used as the control, even though tacrine (100 μM) was added.

This has revealed that the gene transcription, controlled by serum responsive factor, is specifically promoted in the human GPR30 expression cells by tacrine stimulation.

An experiment substantially the same as above may be performed by adding a test compound instead of tacrine to search for a compound activating GPR30 to promote the luciferase gene transcription activity controlled by serum responsive factor.

INDUSTRIAL APPLICABILITY

A tacrine compound (e.g., Compound (I)), a compound promoting the activities of a tacrine compound or a salt thereof, a compound promoting the binding between the receptor of the present invention (e.g., GPR30, etc.) and a tacrine compound, and the like are useful as, for example, preventive/therapeutic agents, metastasization inhibitors, cell apoptosis promoters, cell proliferation inhibitors or the like for cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.).

A compound inhibiting the activities of a tacrine compound or a salt thereof, and the like is useful as, for example, a preventive/therapeutic agents for cardiac diseases (e.g., cardiomyopathy, cardiac infarction, heart failure, angina pectoris, etc.), a preventive/therapeutic agents for myocardial cell apoptosis, or the like.

The receptor according to the present invention (e.g., GPR30, etc.) and a tacrine compound are useful for screening a compound or a salt thereof having a cancer preventive/therapeutic action, a cancel cell apoptosis promoting action, or a cancer cell proliferation inhibiting action on cancers (e.g., brain tumor, pituitary tumor, glioma, acoustic neuroma, pharyngeal cancer, laryngeal cancer, tongue cancer, thymoma, mesothelioma, breast cancer, lung cancer, non-small cell lung cancer, small cell lung cancer, gastric cancer, esophageal cancer, colorectal cancer, colon cancer, rectal cancer, liver cancer, hepatocellular carcinoma, pancreatic cancer, pancreatic endocrine tumor, bile duct cancer, gallbladder cancer, penile cancer, renal cancer, renal pelvic cancer, urethral cancer, renal cell cancer, testicular tumor, prostate cancer, bladder cancer, vulvar cancer, uterine cancer, cervical cancer, uterine body cancer, uterine sarcoma, trophoblastic disease, vaginal cancer, ovary cancer, ovarian germ cell tumor, skin cancer, malignant melanoma, mycosis fungoides, basalioma, soft part sarcoma, malignant lymphoma, Hodgkin's disease, myelodysplastic syndrome, multiple myeloma, leukemia, acute myeloid leukemia, chronic myeloid leukemia, acute lymphocytic leukemia, chronic lymphocytic leukemia, adult T-cell leukemia, chronic myeloproliferative disease, pancreatic endocrine tumor, unknown primary cancer, etc.), a preventive/therapeutic action on cardiac diseases (e.g., cardiomyopathy, cardiac infarction, heart failure, angina pectoris, etc.), a preventive/therapeutic action on myocardial cell apoptosis, or the like.

The invention claimed is:

1. A method for screening a compound or a salt thereof that alters a cell stimulating activity, comprising:
measuring an intracellular calcium concentration increase activity of a GPR30 protein, (i) when a tacrine compound is brought in contact with the protein in a cell in the absence of a test compound, and (ii) when a tacrine compound is brought in contact with the protein in a cell in the presence of the test compound, wherein
said GPR30 protein comprises the amino acid sequence represented by SEQ ID NO: 1 or an amino acid sequence having at least 80% homology to the amino acid sequence represented by SEQ ID NO: 1;
comparing the intracellular calcium concentration increase activity between (i) and (ii); and
selecting the compound that alters the intracellular calcium concentration increase activity;
wherein the tacrine compound is a compound represented by formula:

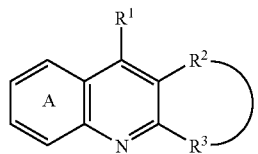

(in the formula, ring A represents an optionally substituted benzene;

$R^1$ represents an optionally substituted amino; and
each of $R^2$ and $R^3$ independently represents an optionally substituted hydrocarbon group, an optionally substituted heterocyclic group, or acyl; or
$R^2$ and $R^3$ may form an optionally substituted 3- to 10-membered homo- or heterocyclic group with a carbon atom mutually bound and adjacent thereto)
or a salt thereof.

2. The screening method according to claim 1, wherein the protein comprises the amino acid sequence represented by SEQ ID NO: 1 and the tacrine compound is tacrine.

3. The screening method according to claim 1, wherein the amino acid sequence having at least 80% homology to the amino acid sequence represented by SEQ ID NO: 1 is the amino acid sequence represented by SEQ ID NO: 2, SEQ ID NO: 3 or SEQ ID NO: 4.

4. The screening method according to claim 1, wherein said measuring and comparing the intracellular calcium concentration increase activity of the tacrine compound is performed on a cell, or a membrane fraction of the cell, containing the protein.

5. The screening method according to claim 4, wherein the protein is expressed on a cell membrane by culturing a transformant containing a DNA encoding the protein.

6. The screening method according to claim 4 or 5, wherein the tacrine compound is a labeled tacrine compound.

7. The screening method according to claim 1, wherein the tacrine compound is tacrine.

* * * * *

SEQUENCE LISTING

```
<160> NUMBER OF SEQ ID NOS: 8

<210> SEQ ID NO 1
<211> LENGTH: 375
<212> TYPE: PRT
<213> ORGANISM: Homo sapiens

<400> SEQUENCE: 1

Met Asp Val Thr Ser Gln Ala Arg Gly Val Gly Leu Glu Met Tyr Pro
                5                   10                  15

Gly Thr Ala His Ala Ala Ala Pro Asn Thr Thr Ser Pro Glu Leu Asn
            20                  25                  30
```

Leu Ser His Pro Leu Leu Gly Thr Ala Leu Ala Asn Gly Thr Gly Glu
             35                  40                  45

Leu Ser Glu His Gln Gln Tyr Val Ile Gly Leu Phe Leu Ser Cys Leu
 50                  55                  60

Tyr Thr Ile Phe Leu Phe Pro Ile Gly Phe Val Gly Asn Ile Leu Ile
 65                  70                  75                  80

Leu Val Val Asn Ile Ser Phe Arg Glu Lys Met Thr Ile Pro Asp Leu
                 85                  90                  95

Tyr Phe Ile Asn Leu Ala Val Ala Asp Leu Ile Leu Val Ala Asp Ser
                100                 105                 110

Leu Ile Glu Val Phe Asn Leu His Glu Arg Tyr Tyr Asp Ile Ala Val
             115                 120                 125

Leu Cys Thr Phe Met Ser Leu Phe Leu Gln Val Asn Met Tyr Ser Ser
         130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375

<210> SEQ ID NO 2
<211> LENGTH: 375
<212> TYPE: PRT
<213> ORGANISM: Rattus norvegicus

<400> SEQUENCE: 2

Met Ala Ala Thr Thr Pro Ala Gln Asp Val Gly Val Glu Ile Tyr Leu
                 5                  10                  15

Gly Pro Val Trp Pro Ala Pro Ser Asn Ser Thr Pro Leu Ala Leu Asn
             20                  25                  30

```
Leu Ser Leu Ala Leu Arg Glu Asp Ala Pro Gly Asn Leu Thr Gly Asp
        35                  40                  45

Leu Ser Glu His Gln Gln Tyr Val Ile Ala Leu Phe Leu Ser Cys Leu
 50                  55                  60

Tyr Thr Ile Phe Leu Phe Pro Ile Gly Phe Val Gly Asn Ile Leu Ile
 65                  70                  75                  80

Leu Val Val Asn Ile Ser Phe Arg Glu Lys Met Thr Ile Pro Asp Leu
                 85                  90                  95

Tyr Phe Ile Asn Leu Ala Ala Ala Asp Leu Ile Leu Val Ala Asp Ser
                100                 105                 110

Leu Ile Glu Val Phe Asn Leu Asp Glu Gln Tyr Tyr Asp Ile Ala Val
            115                 120                 125

Leu Cys Thr Phe Met Ser Leu Phe Leu Gln Ile Asn Met Tyr Ser Ser
        130                 135                 140

Val Phe Phe Leu Thr Trp Met Ser Phe Asp Arg Tyr Leu Ala Leu Ala
145                 150                 155                 160

Lys Ala Met Arg Cys Gly Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Arg His Thr Glu Glu Ala Cys Phe Cys Phe
        195                 200                 205

Ala Asp Val Arg Glu Val Gln Trp Leu Glu Val Thr Leu Gly Phe Ile
210                 215                 220

Val Pro Phe Ala Ile Ile Gly Leu Cys Tyr Ser Leu Ile Val Arg Ala
225                 230                 235                 240

Leu Ile Arg Ala His Arg His Arg Gly Leu Arg Pro Arg Arg Gln Lys
                245                 250                 255

Ala Leu Arg Met Ile Phe Ala Val Val Leu Val Phe Phe Ile Cys Trp
            260                 265                 270

Leu Pro Glu Asn Val Phe Ile Ser Val His Leu Leu Gln Trp Ala Gln
        275                 280                 285

Pro Gly Asp Thr Pro Cys Lys Gln Ser Phe Arg His Ala Tyr Pro Leu
290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Val Ala Gln Lys Thr Ser Leu Pro Ala Leu Asn Arg Phe Cys
            340                 345                 350

His Ala Thr Leu Lys Ala Val Ile Pro Asp Ser Thr Glu Gln Ser Asp
        355                 360                 365

Val Lys Phe Ser Ser Ala Val
        370                 375

<210> SEQ ID NO 3
<211> LENGTH: 375
<212> TYPE: PRT
<213> ORGANISM: Mus musculus

<400> SEQUENCE: 3

Met Asp Ala Thr Thr Pro Ala Gln Thr Val Gly Val Glu Ile Tyr Leu
              5                  10                  15

Gly Pro Val Trp Pro Ala Pro Ser Asn Ser Thr Pro Leu Ala Leu Asn
             20                  25                  30
```

Leu Ser Leu Ala Leu Arg Glu Asp Ala Pro Gly Asn Leu Thr Gly Asp
            35                  40                  45

Leu Ser Glu His Gln Gln Tyr Val Ile Ala Leu Phe Leu Ser Cys Leu
        50                  55                  60

Tyr Thr Ile Phe Leu Phe Pro Ile Gly Phe Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Ala Ala Asp Leu Ile Leu Val Ala Asp Ser
                100                 105                 110

Leu Ile Glu Val Phe Asn Leu Asp Glu Gln Tyr Tyr Asp Ile Ala Val
            115                 120                 125

Leu Cys Thr Phe Met Ser Leu Phe Leu Gln Ile Asn Met Tyr Ser Ser
        130                 135                 140

Val Phe Phe Leu Thr Trp Met Ser Phe Asp Arg Tyr Leu Ala Leu Ala
145                 150                 155                 160

Lys Ala Met Arg Cys Gly Leu Phe Arg Thr Lys His His Ala Arg Leu
                165                 170                 175

Ser Cys Gly Leu Ile Trp Met Ala Ser Val Ser Ala Thr Leu Val Pro
                180                 185                 190

Phe Thr Ala Val His Leu Arg His Thr Glu Glu Ala Cys Phe Cys Phe
            195                 200                 205

Ala Asp Val Arg Glu Val Gln Trp Leu Glu Val Thr Leu Gly Phe Ile
        210                 215                 220

Met Pro Phe Ala Ile Ile Gly Leu Cys Tyr Ser Leu Ile Val Arg Ala
225                 230                 235                 240

Leu Ile Arg Ala His Arg His Arg Gly Leu Arg Pro Arg Arg Gln Lys
                245                 250                 255

Ala Leu Arg Met Ile Phe Ala Val Val Leu Val Phe Phe Ile Cys Trp
                260                 265                 270

Leu Pro Glu Asn Val Phe Ile Ser Val His Leu Leu Gln Trp Thr Gln
            275                 280                 285

Pro Gly Asp Thr Pro Cys Lys Gln Ser Phe Arg His Ala Tyr Pro Leu
        290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Val Glu Gln Lys Thr Ser Leu Pro Ala Leu Asn Arg Phe Cys
            340                 345                 350

His Ala Thr Leu Lys Ala Val Ile Pro Asp Ser Thr Glu Gln Ser Glu
        355                 360                 365

Ile Arg Phe Ser Ser Ala Val
370                 375

<210> SEQ ID NO 4
<211> LENGTH: 375
<212> TYPE: PRT
<213> ORGANISM: Homo sapiens

<400> SEQUENCE: 4

Met Asp Val Thr Ser Gln Ala Arg Gly Val Gly Leu Glu Met Tyr Pro
                5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
 50                  55                  60

Tyr Thr Ile Phe Leu Phe Pro Ile Gly Phe Val Gly Asn Ile Leu Ile
 65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
                100                 105                 110

Leu Ile Glu Val Phe Asn Leu His Glu Arg Tyr Tyr Asp Ile Ala Val
            115                 120                 125

Leu Cys Thr Phe Met Ser Leu Phe Leu Gln Val Asn Met Tyr Ser Ser
        130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His Ala Arg Leu
                165                 170                 175

Ser Cys Gly Leu Ile Trp Met Ala Ser Val Ser Ala Thr Leu Val Pro
                180                 185                 190

Phe Thr Ala Val His Leu Gln His Thr Asp Glu Ala Cys Phe Cys Phe
            195                 200                 205

Ala Asp Val Arg Glu Val Gln Trp Leu Glu Val Thr Leu Gly Phe Ile
        210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
                260                 265                 270

Leu Pro Glu Asn Val Phe Ile Ser Val His Leu Leu Gln Arg Thr Gln
            275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
370                 375

<210> SEQ ID NO 5
<211> LENGTH: 1125
<212> TYPE: DNA
<213> ORGANISM: Homo sapiens

<400> SEQUENCE: 5
atggatgtga cttcccaagc ccggggcgtg ggcctggaga tgtacccagg caccgcgcac     60
gctgcggccc ccaacaccac ctcccccgag ctcaacctgt cccacccgct cctgggcacc    120
gccctggcca atgggacagg tgagctctcg gagcaccagc agtacgtgat cggcctgttc    180

```
ctctcgtgcc tctacaccat cttcctcttc cccatcggct tgtgggcaa  catcctgatc     240 ctggtggtga acatcagctt ccgcgagaag atgaccatcc ccgacctgta cttcatcaac     300
ctggcggtgg cggacctcat cctggtggcc gactccctca ttgaggtgtt caacctgcac     360
gagcggtact acgacatcgc cgtcctgtgc accttcatgt cgctcttcct gcaggtcaac     420
atgtacagca gcgtcttctt cctcacctgg atgagcttcg accgctacat cgccctggcc     480
agggccatgc gctgcagcct gttccgcacc aagcaccacg cccggctgag ctgtggcctc     540
atctggatgg catccgtgtc agccacgctg gtgcccttca ccgccgtgca cctgcagcac     600
accgacgagg cctgcttctg tttcgcggat gtccgggagg tgcagtggct cgaggtcacg     660
ctgggcttca tcgtgccctt cgccatcatc ggcctgtgct actccctcat tgtccgggtg     720
ctggtcaggg cgcaccggca ccgtgggctg cggcccggc  ggcagaaggc gctccgcatg     780
atcctcgcgg tggtgctggt cttcttcgtc tgctggctgc cggagaacgt cttcatcagc     840
gtgcacctcc tgcagcggac gcagcctggg gccgctccct gcaagcagtc tttccgccat     900
gcccaccccc tcacgggcca cattgtcaac ctcgccgcct tctccaacag ctgcctaaac     960
cccctcatct acagctttct cggggagacc ttcaggaca  agctgaggct gtacattgag    1020
cagaaaacaa atttgccggc cctgaaccgc ttctgtcacg ctgccctgaa ggccgtcatt    1080
ccagacagca ccgagcagtc ggatgtgagg ttcagcagtg ccgtg                    1125

<210> SEQ ID NO 6
<211> LENGTH: 1125
<212> TYPE: DNA
<213> ORGANISM: Rattus norvegicus

<400> SEQUENCE: 6
atggctgcaa ctactccagc acaagatgtt ggcgtagaga tctacctagg tcccgtgtgg      60
ccagcccctt ccaacagcac ccctctggcc ctcaacctgt ccctggcgct gcgggaagat     120
gccccgggga acctcactgg ggacctctct gaacatcagc aatatgtgat cgctctcttc     180
ctctcctgcc tctacaccat cttcctcttc cccatcggct tgtgggcaa  catcctcatc     240 ttggtggtga acatcagctt ccgggagaag atgactatcc cagacctgta cttcatcaac     300
ctggcagcgg ccgacctcat cctggtggcc gactccctga tcgaggtgtt caacctggac     360
gagcagtact acgatatcgc cgtgctctgc accttcatgt ccctcttcct gcagatcaac     420
atgtacagca gcgtcttctt cctcacctgg atgagcttcg acaggtacct ggcgctggcc     480
aaagccatgc gctgtggcct cttccgcacc aagcaccacg cgcggctcag ctgtggcctc     540
atctggatgg cctcagtgtc cgccacgctg gtgcccttca cggccgtgca tctgcggcac     600
accgaggagg cctgcttctg ctttgccgat gtcagggagg tgcagtggct ggaggtcacg     660
ctgggcttca ttgtgccctt cgccatcatc ggcctgtgct attccctcat cgtgcgggcc     720
ctcatccggg cccacaggca tcgtggcctg cgcccacgca ggcagaaagc cctgaggatg     780
atcttcgcag tggtccttgt cttcttcatc tgctggctgc cggagaacgt cttcatcagc     840
gtccacctac tgcagtgggc gcagccaggg gacactccct gcaagcagtc tttccgtcat     900
gcctacccct tgacaggcca catagtcaac ctggcagcct tctccaacag ctgcctgaat     960
cccctcatct atagcttcct gggagagacc ttcaggaca  agctcaggct gtatgtggcg    1020
cagaagacga gcctgccagc tctcaaccgc ttctgccatg ccacgctcaa ggcagtcata    1080
ccagacagca cggagcagtc agatgtcaag ttcagcagtg ctgta                    1125
```

```
<210> SEQ ID NO 7
<211> LENGTH: 1125
<212> TYPE: DNA
<213> ORGANISM: Mus musculus

<400> SEQUENCE: 7
atggatgcga ctactccagc ccaaactgtt ggggtggaga tctacctagg tcccgtgtgg      60
ccagcccctt ccaacagcac ccctctggcc ctcaacttgt ccctggcact gcgggaagat     120
gccccgggga acctcactgg ggacctctct gagcatcagc agtacgtgat tgccctcttc     180
ctctcctgcc tctacaccat cttcctcttt cctattggct tgtgggcaa catcctcatc      240 ctggtggtga acatcagctt ccgggagaag atgaccatcc agacctgta cttcatcaac      300 ctggcggcgg ccgacctcat cctggtggct gactccctga ttgaggtgtt caacctggac     360
gagcagtact acgacatcgc agtgctctgc accttcatgt ccctcttcct gcagatcaac     420
atgtacagca gcgtcttctt cctcacctgg atgagcttcg acaggtacct agcgctggcc     480
aaggccatgc gctgtggcct cttccgcacc aagcaccacg cacggctcag ctgtggcctc     540
atctggatgg cctcagtgtc cgccacgctg gtgcccttca cagcggtgca cctgcggcac     600
acggaggagg cctgcttctg ctttgctgat gtcaggagg tgcagtggct ggaggtcaca       660
ctgggcttca tcatgcccct cgccatcatt ggcctctgct actccctcat cgtgcgagcc     720
ctcatccggg cccacaggca ccgcggcctg cgcccacgca ggcagaaagc cctgaggatg     780
atcttcgcag tggtccttgt tttcttcatc tgctggctgc cggagaacgt cttcatcagt     840
gtccacctac tgcagtggac gcagccaggg acactccct gcaagcagtc tttccgtcac      900
gcctacccct tgacaggcca catagtcaac cttgcagcct ctccaacag ctgcctgaat       960 cccctcatct acagcttcct gggagagacc ttcaggaca agctcaggct ctatgtggag     1020
cagaagacga gcctgccggc tctgaaccgc ttctgccatg ccacgctcaa ggccgtcatt     1080
ccagacagca cagagcagtc agagatcagg ttcagcagtg ctgtg                    1125

<210> SEQ ID NO 8
<211> LENGTH: 1125
<212> TYPE: DNA
<213> ORGANISM: Homo sapiens

<400> SEQUENCE: 8
atggatgtga cttcccaagc ccggggcgtg ggcctggaga tgtacccagg caccgcgcag      60
cctgcggccc ccaacaccac ctcccccgag ctcaacctgt ccacccgct cctgggcacc      120 gccctggcca atgggacagg tgagctctcg gagcaccagc agtacgtgat cggcctgttc     180
ctctcgtgcc tctacaccat cttcctcttc cccatcggct tgtgggcaa catcctgatc      240 ctggtggtga acatcagctt ccgcgagaag atgaccatcc cgacctgta cttcatcaac      300 ctggcggtgg cggacctcat cctggtggcc gactccctca ttgaggtgtt caacctgcac     360
gagcggtact acgacatcgc cgtcctgtgc accttcatgt cgctcttcct gcaggtcaac     420
atgtacagca gcgtcttctt cctcacctgg atgagcttcg accgctacat cgccctggcc     480
agggccatgc gctgcagcct gttccgcacc aagcaccacg cccggctgag ctgtggcctc     540
atctggatgg catccgtgtc agccacgctg gtgcccttca ccgccgtgca cctgcagcac     600
accgacgagg cctgcttctg tttcgcggat gtccgggagg tgcagtggct cgaggtcacg     660
ctgggcttca tcgtgccctt cgccatcatc ggcctgtgct actccctcat tgtccgggtg     720
ctggtcaggg cgcaccggca ccgtgggctg cggcccggc ggcagaaggc gctccgcatg      780
atcctcgcgg tggtgctggt cttcttcgtc tgctggctgc cggagaacgt cttcatcagc     840
```

```
gtgcacctcc tgcagcggac gcagcctggg gccgctccct gcaagcagtc tttccgccat    900 gcccacccc  tcacgggcca cattgtcaac ctcgccgcct tctccaacag ctgcctaaac    960
cccctcatct acagctttct cggggagacc ttcagggaca agctgaggct gtacattgag   1020
cagaaaacaa atttgccggc cctgaaccgc ttctgtcacg ctgccctgaa ggccgtcatt   1080
ccagacagca ccgagcagtc ggatgtgagg ttcagcagtg ccgtg                   1125
```